(12) United States Patent
Savoy et al.

(10) Patent No.: US 11,988,662 B2
(45) Date of Patent: May 21, 2024

(54) METHODS FOR DETECTING AND QUANTIFYING GAS SPECIES ANALYTES USING DIFFERENTIAL GAS SPECIES DIFFUSION

(71) Applicant: Nanohmics, Inc., Austin, TX (US)

(72) Inventors: Steve M. Savoy, Austin, TX (US);
Kyle W. Hoover, Austin, TX (US);
Daniel R. Mitchell, Austin, TX (US);
Jeremy J. John, Austin, TX (US);
Chris W. Mann, Austin, TX (US);
Alexander P. Greis, Austin, TX (US)

(73) Assignee: Nanohmics, Inc., Austin, TX (US)

( * ) Notice: Subject to any disclaimer, the term of this patent is extended or adjusted under 35 U.S.C. 154(b) by 1016 days.

(21) Appl. No.: 15/372,075

(22) Filed: Dec. 7, 2016

(65) Prior Publication Data

US 2017/0160221 A1  Jun. 8, 2017
US 2017/0343538 A9  Nov. 30, 2017

Related U.S. Application Data

(60) Provisional application No. 62/263,768, filed on Dec. 7, 2015.

(51) Int. Cl.
*G01N 33/53* (2006.01)
*G01N 33/00* (2006.01)
*G01N 33/497* (2006.01)

(52) U.S. Cl.
CPC ..... *G01N 33/5308* (2013.01); *G01N 33/0008* (2013.01); *G01N 33/0031* (2013.01);
(Continued)

(58) Field of Classification Search
CPC ........... G01N 33/5308; G01N 33/0008; G01N 33/0031; G01N 33/0047; G01N 33/497; G01N 2033/4975
See application file for complete search history.

(56) References Cited

U.S. PATENT DOCUMENTS 3,695,848 A  10/1972  Taguchi
3,971,065 A  7/1976  Bayer
(Continued)

FOREIGN PATENT DOCUMENTS

EP  0652436 B1  3/2002
WO  0032044 A1  6/2000
(Continued)

OTHER PUBLICATIONS

Wan, Jing, et al. "Silicon nanowire sensor for gas detection fabricated by nanoimprint on SU8/SiO2/PMMA trilayer." Microelectronic Engineering 86.4-6 (2009): 1238-1242.*
(Continued)

*Primary Examiner* — Robert J Eom
(74) *Attorney, Agent, or Firm* — Murphy Strategic IP; George L. Murphy

(57) ABSTRACT

Methods and sensors for the detection, identification, and quantification of one or more gas species, including volatile organic compounds, in a test sample are described. Methods employ gas sensors comprising a diffusion matrix present on the sensor surface. A gas analyte in a test sample diffuses through the matrix and is detected upon interaction of the analyte with the sensor. A response profile of a gas sensor to a gas analyte in the test sample is compared to a control gas sensor response profile determined in a similar manner for a known gas species. Comparisons of test sample and control sample sensor response profiles enable detection, identification, and quantification of a gas species analyte in a test sample.

21 Claims, 28 Drawing Sheets

(52) U.S. Cl.
CPC ....... *G01N 33/0047* (2013.01); *G01N 33/497* (2013.01); *G01N 2033/4975* (2013.01)

(56) References Cited

U.S. PATENT DOCUMENTS

| | | | |
|---|---|---|---|
| 4,542,640 A | | 9/1985 | Clifford |
| 5,045,285 A | * | 9/1991 | Kolesar, Jr. ........ G01N 27/4141 |
| | | | 204/400 |
| 5,077,210 A | | 12/1991 | Eigler et al. |
| 5,106,756 A | | 4/1992 | Zaromb |
| 5,284,570 A | | 2/1994 | Savage et al. |
| 5,411,709 A | | 5/1995 | Furuki et al. |
| 5,694,932 A | | 12/1997 | Michel |
| 5,807,701 A | | 9/1998 | Payne et al. |
| 5,837,832 A | | 11/1998 | Chee et al. |
| 5,889,196 A | | 3/1999 | Ueno et al. |
| 5,936,730 A | | 8/1999 | Foley et al. |
| 6,010,616 A | | 1/2000 | Lewis et al. |
| 6,028,331 A | | 2/2000 | Mastromatteo et al. |
| 6,238,869 B1 | | 5/2001 | Kris et al. |
| 6,268,222 B1 | | 7/2001 | Chandler et al. |
| 6,277,489 B1 | | 8/2001 | Abbott |
| 6,287,452 B1 | | 9/2001 | Allen et al. |
| 6,327,410 B1 | | 12/2001 | Walt et al. |
| 6,391,562 B2 | | 5/2002 | Kambara et al. |
| 6,426,184 B1 | | 7/2002 | Gao et al. |
| 6,432,360 B1 | | 8/2002 | Church |
| 6,468,657 B1 | | 10/2002 | Hou et al. |
| 6,479,297 B1 | | 11/2002 | Sandhu |
| 6,567,163 B1 | | 5/2003 | Sandstrom |
| 6,638,416 B2 | | 10/2003 | Wang et al. |
| 6,649,403 B1 | | 11/2003 | McDevitt et al. |
| 6,677,606 B1 | | 1/2004 | Rajh et al. |
| 6,689,321 B2 | | 2/2004 | Sandhu |
| 6,787,308 B2 | | 9/2004 | Balasubramanian et al. |
| 6,833,601 B2 | | 12/2004 | Murakami |
| 6,849,166 B2 | | 2/2005 | Kita |
| 6,849,239 B2 | | 2/2005 | Morris |
| 6,872,645 B2 | | 3/2005 | Duan et al. |
| 7,057,168 B2 | | 6/2006 | Miller et al. |
| 7,118,900 B2 | | 10/2006 | Seul et al. |
| 7,129,554 B2 | | 10/2006 | Lieber et al. |
| 7,182,916 B2 | | 2/2007 | Noda et al. |
| 7,211,654 B2 | | 5/2007 | Gao et al. |
| 7,297,497 B2 | | 11/2007 | Montagu et al. |
| 7,301,199 B2 | | 11/2007 | Lieber et al. |
| 7,312,095 B1 | | 12/2007 | Gabriel et al. |
| 7,321,143 B2 | | 1/2008 | Kunath et al. |
| 7,335,153 B2 | | 2/2008 | Seul et al. |
| 7,335,942 B2 | | 2/2008 | Edinger et al. |
| 7,348,184 B2 | | 3/2008 | Rich et al. |
| 7,385,267 B2 | | 6/2008 | Lieber et al. |
| 7,449,757 B2 | | 11/2008 | Bradley et al. |
| 7,460,958 B2 | | 12/2008 | Walsh et al. |
| 7,489,017 B2 | | 2/2009 | Patel et al. |
| 7,491,680 B2 | | 2/2009 | Gao et al. |
| 7,544,638 B2 | | 6/2009 | Gao et al. |
| 7,553,958 B2 | | 6/2009 | Gao et al. |
| 7,575,933 B2 | | 8/2009 | Gabriel et al. |
| 7,786,530 B2 | | 8/2010 | Kakoschke et al. |
| 7,838,466 B2 | | 11/2010 | Gao et al. |
| 7,859,029 B2 | | 12/2010 | Lee et al. |
| 7,948,041 B2 | | 5/2011 | Bryant et al. |
| 8,443,647 B1 | | 5/2013 | Kolmakov |
| 8,450,131 B2 | | 5/2013 | Savoy et al. |
| 8,754,454 B2 | | 6/2014 | Bryant et al. |
| 8,900,517 B2 | | 12/2014 | Gabriel et al. |
| 9,063,053 B2 | | 6/2015 | Patolsky et al. |
| 9,603,560 B2 | | 3/2017 | Monty et al. |
| 9,768,162 B2 | | 9/2017 | Savoy et al. |
| 9,828,696 B2 | | 11/2017 | Savoy et al. |
| 10,386,351 B2 | | 8/2019 | Savoy et al. |
| 10,386,365 B2 | | 8/2019 | Savoy et al. |
| 2001/0029049 A1 | | 10/2001 | Walt et al. |
| 2002/0018199 A1 | | 2/2002 | Blumenfeld et al. |
| 2002/0028455 A1 | | 3/2002 | Laibinis et al. |
| 2002/0146745 A1 | | 10/2002 | Natan et al. |
| 2003/0040129 A1 | | 2/2003 | Shah |
| 2003/0065452 A1 | | 4/2003 | Hickman |
| 2003/0118595 A1 | | 6/2003 | Niemeyer et al. |
| 2004/0121339 A1 | | 6/2004 | Zhou et al. |
| 2004/0132070 A1 | | 7/2004 | Star et al. |
| 2004/0136866 A1 | | 7/2004 | Pontis et al. |
| 2004/0161370 A1 | * | 8/2004 | Sunshine ........... G01N 33/0006 |
| | | | 422/83 |
| 2004/0248144 A1 | | 12/2004 | Mir |
| 2005/0032060 A1 | | 2/2005 | Shah et al. |
| 2005/0053949 A1 | | 3/2005 | Silin |
| 2005/0065446 A1 | | 3/2005 | Talton |
| 2005/0095649 A1 | | 5/2005 | Aebersold et al. |
| 2005/0130174 A1 | | 6/2005 | Yijia et al. |
| 2005/0142567 A1 | | 6/2005 | Su et al. |
| 2006/0035229 A1 | | 2/2006 | Schwarnweber et al. |
| 2006/0068504 A1 | | 3/2006 | Kogi |
| 2006/0137669 A1 | | 6/2006 | Lindner |
| 2006/0263763 A1 | | 11/2006 | Simpson et al. |
| 2007/0015213 A1 | | 1/2007 | Mutz et al. |
| 2007/0048180 A1 | | 3/2007 | Gabriel et al. |
| 2007/0138007 A1 | | 6/2007 | Yemini et al. |
| 2007/0158547 A1 | | 7/2007 | Rich et al. |
| 2007/0224616 A1 | | 9/2007 | Gulari et al. |
| 2008/0044925 A1 | | 2/2008 | Isojima et al. |
| 2008/0146459 A1 | | 6/2008 | Iwakura et al. |
| 2008/0221806 A1 | | 9/2008 | Bryant et al. |
| 2008/0293591 A1 | | 11/2008 | Taussig et al. |
| 2008/0312105 A1 | | 12/2008 | Bacher et al. |
| 2009/0018027 A1 | | 1/2009 | Ronald et al. |
| 2009/0036324 A1 | | 2/2009 | Fan et al. |
| 2009/0117571 A1 | | 5/2009 | Solanki et al. |
| 2009/0153864 A1 | | 6/2009 | Kim et al. |
| 2009/0156427 A1 | | 6/2009 | Zhang et al. |
| 2009/0211437 A1 | | 8/2009 | Fleischer et al. |
| 2011/0071037 A1 | | 3/2011 | Muller et al. |
| 2011/0179852 A1 | | 7/2011 | Polonsky et al. |
| 2012/0178199 A1 | | 7/2012 | Savoy et al. |
| 2012/0245055 A1 | | 9/2012 | Savoy et al. |
| 2012/0263922 A1 | | 10/2012 | Advincula |
| 2014/0212979 A1 | | 7/2014 | Burgi et al. |
| 2014/0249052 A1 | | 9/2014 | Mehmet et al. |
| 2014/0332407 A1 | | 11/2014 | Mai et al. |
| 2017/0160227 A1 | | 6/2017 | Savoy et al. |
| 2017/0160250 A1 | | 6/2017 | Savoy et al. |
| 2017/0363600 A9 | | 12/2017 | Savoy et al. |

FOREIGN PATENT DOCUMENTS

| | | |
|---|---|---|
| WO | 0079243 A1 | 12/2000 |
| WO | 0100876 A1 | 1/2001 |
| WO | 2001000876 A1 | 1/2001 |
| WO | 2002103371 A2 | 12/2002 |
| WO | 2003079401 A2 | 9/2003 |
| WO | 2003095469 A1 | 11/2003 |
| WO | 2003102546 A2 | 12/2003 |
| WO | 2004011672 A1 | 5/2004 |
| WO | 2005030978 A2 | 4/2005 |
| WO | 2005103718 A1 | 11/2005 |
| WO | 20050103718 A1 | 11/2005 |
| WO | 2006113618 A1 | 10/2006 |
| WO | 2006124089 A1 | 11/2006 |
| WO | 2007082955 A1 | 7/2007 |
| WO | 2007139849 A2 | 12/2007 |
| WO | 2008027571 A2 | 3/2008 |
| WO | 2008033848 A2 | 3/2008 |
| WO | 2008082713 A2 | 7/2008 |
| WO | 2010135834 A1 | 12/2010 |
| WO | 2012078908 A1 | 6/2012 |
| WO | 2012151306 A2 | 11/2012 |
| WO | 2013008170 A2 | 1/2013 |

OTHER PUBLICATIONS

Yang, Yoon Seok, Seung-Chul Ha, and Yong Shin Kim. "A matched-profile method for simple and robust vapor recognition in electronic

(56) References Cited

OTHER PUBLICATIONS nose (E-nose) system." Sensors and Actuators B: Chemical 106.1 (2005): 263-270. (Year: 2005).*
Office Action issued in U.S. Appl. No. 13/070,077, dated Jun. 5, 2012.
Office Action issued in U.S. Appl. No. 13/070,077, dated Aug. 7, 2012.
Office Action issued in U.S. Appl. No. 13/070,077, dated Dec. 26, 2012.
Office Action issued in U.S. Appl. No. 13/070,077, dated Feb. 7, 2013.
Office Action issued in U.S. Appl. No. 13/070,077, dated Apr. 4, 2013.
Office Action issued in U.S. Appl. No. 13/070,077, dated Apr. 23, 2014.
Office Action issued in U.S. Appl. No. 13/070,077, dated Nov. 6, 2014.
Office Action issued in U.S. Appl. No. 13/070,077, dated Mar. 19, 2015.
Office Action issued in U.S. Appl. No. 13/070,077, dated Oct. 20, 2015.
Office Action issued in U.S. Appl. No. 13/070,077, dated May 12, 2017.
Office Action issued in U.S. Appl. No. 13/070,077, dated Jul. 24, 2017.
Samain et al, "Differentiating a Diverse Range of Volatile Organic Compounds with Polyfluorophore Sensors Built on a DNA Scaffold", Chem. Eur. J., vol. 17, pp. 174-183, (Dec. 10, 2010).
Thewes et al, "A CMOS Medium Density DNA Microarray with Electronic Readout", Mater. Res. Soc. Symp. Proc., vol. 869, pp. D3.4.1-D3.4.11, (2005).
Stadler et al, "Multifunctional CMOS Microchip Coatings for Protein and Peptide Arrays", J. Proteome Res., vol. 6, pp. 3197-3202, (Jul. 12, 2007).
Rodrigues et al, "Coating of Solid-Phase Microextraction Fibers with Chemically Bonded Silica Particles: Selective Extraction of Polycyclic Aromatic Hydrocarbons from Drinking Water Samples", J. Chromat. Sci., vol. 40, pp. 489-494, (2002).
Schroder et al, "Addressable Microfluidic Polymer Chip for DNA-Directed Immobilization of Oligonucleotide-Tagged Compounds", Small Jour., vol. 5(13), pp. 1547-1552, (Mar. 26, 2009).
Platt et al, "Aptamer evolution for array-based diagnostics", Anal. Biochem., vol. 390, pp. 203-205, (Apr. 15, 2009).
Pizzoni et al, "Selection ofpeptide ligands for piezoelectric peptide based gas sensors arrays using a virtual screening approach", Biosensors Bioelectronics, vol. 52, pp. 247-254, (Sep. 4, 2013).
Niemeyer et al, "Combination of DNA-directed immobilization and immuno-PCR: very sensitive antigen detection by means of self-assembled DNA±protein conjugates", Nucl. Acids Res., vol. 31(16), pp. e90, (2003).
McNally et al, Self-assembly of micro- and nano-scale particles using bio-inspired events, Appl. Surf. Sci., vol. 214, pp. 109-119, (2003).
McCauley et al, "Aptamer-based biosensor arrays for detection and quantification of biological macromolecules" Anal. Biochem., vol. 319, pp. 244-250, (2003).
Kozak et al, "Improving the Signal-to-Noise Performance of Molecular Diagnostics with PEG-Lysine Copolymer Dendrons", Biomacromolecules, vol. 10, pp. 360-365, (Jan. 21, 2009).
Li et al, "In2O3 nanowires as chemical sensors", Applied Phys. Letters, vol. 82(10), pp. 1613-1615, (Mar. 10, 2003).
Kong et al, "Nanotube Molecular Wires as Chemical Sensors", Science, vol. 287, pp. 622-625, (Jan. 28, 2000).
Ivanov et al, "Antibodies Immobilized as Arrays to Profile Protein Post-translational Modifications in Mammalian Cells", Molec. Cell. Proteomics, vol. 3.8, pp. 788-795, (May 3, 2004).
Hui, "Guided molecular self-assembly: a review of recent efforts", Smart Mater. Struct., vol. 12, pp. 264-271, (Mar. 27, 2003).

Hatchett et al, "Composites of Intrinsically Conducting Polymers as Sensing Nanomaterials", B Chem. Rev., pp. A-U, (Jan. 3, 2008).
Dandy et al, "Array feature size influences nucleic acid surface capture in DNA microarrays", Proc. Natl. Acad. Sci., vol. 104(20), pp. 8223-8228, (May 15, 2007).
Compagnone et al, "Gold nanoparticles-peptide based gas sensor arrays for the detection of food aromas", Biosensors Bioelectronics, vol. 42, pp. 618-625, (Nov. 22, 2012).
Chhabra et al,"Spatially Addressable Multiprotein Nanoarrays Templated by Aptamer-Tagged DNA Nanoarchitectures", J. Am. Chem. Soc., vol. 129, pp. 10304-10305, (2007).
Bashir, "DNA Nanobiostructures", Materials Today, vol. Nov.-Dec. 2001, pp. 30-39, (2001).
Cao et al, "Silicon Nanowire-Based Devices for Gas-Phase Sensing", Sensors, vol. 14, pp. 245-271, (Dec. 24, 2013).
De Smet et al, "Organic Surface Modification of Silicon Nanowire-Based Sensor Devices", in Nanowires—Implementations and Applications, Dr. Abbass Hashim (Ed.), InTech, Rijeka, Croatia, Ch. 13, pp. 267-288, (Jul. 18, 2011).
Edelstein et al, "The BARC biosensor applied to the detection of biological warfare agents", Biosensors & Bioelectronics, vol. 14, pp. 805-813, (2000).
Galoppini, "Linkers for anchoring sensitizers to semiconductor nanoparticles", Coordination Chemistry Reviews, vol. 248, pp. 1283-1297, (May 28, 2004).
Georgiev et al, "Fully CMOS-compatible top-down fabrication of sub-50 nm silicon nanowire sensing devices", Microelectronic Engineering, vol. 118, pp. 47-53, (Jan. 7, 2014).
Huang et al, "Gas Sensors Based on Semiconducting Metal Oxide One-Dimensional Nanostructures", Sensors, vol. 9, pp. 9903-9924, (Dec. 4, 2009).
Kanan et al, "Semiconducting Metal Oxide Based Sensors for Selective Gas Pollutant Detection", Sensors, vol. 9, pp. 8158-8196, (Oct. 16, 2009).
Kim et al, "Advances and new directions in gas-sensing devices", Acta Materialia, vol. 61, pp. 974-1000, (2013).
Kim et al, "Direct label-free electrical immunodetection in human serum using a flow-through-apparatus approach with integrated field-effect transistors", Biosensors and Bioelectronics, vol. 25, pp. 1767-1773, (Dec. 29, 2009).
Korotcenkov et al, "Engineering approaches for the improvement of conductometric gas sensor parameters Part 1. Improvement of sensor sensitivity and selectivity (short survey)", Sensors and Actuators B:Chemical, vol. 188, pp. 709-728, (Aug. 7, 2013).
Lund et al, "Label-Free Direct Electronic Detection of Biomolecules with Amorphous Silicon Nanostructures", Nanomedicine, vol. 2(4), pp. 230-238, (Dec. 2006).
McAlpine et al, "Peptide-Nanowire Hybrid Materials for Selective Sensing of Small Molecules", J Am Chem Soc, vol. 130(29), pp. 9583-9589, (Jul. 23, 2008).
Oleinikov et al, "Self-Assembling Protein Arrays Using Electronic Semiconductor Microchips and in Vitro Translation", J Proteome Res, vol. 2, pp. 313-319, (Apr. 5, 2003).
Park et al, "Array-Based Electrical Detection of DNA with Nanoparticle Probes", Science, vol. 295, pp. 1503-1506, (Feb. 22, 2002).
Sakai, "Theory of gas-diffusion controlled sensitivity for thin film semiconductor gas sensor", Sensors and Actuators B:Chemical, vol. 80, pp. 125-131, (2001).
Samain et al, "Polyfluorophores on a DNA Backbone: Sensors of Small Molecules in the Vapor Phase", Angew Chem Int Ed Engl, vol. 49(39), pp. 7025-7029, (Sep. 17, 2010).
Stern et al, "Label-free biomarker detection from whole blood", Nature Nanotechnology, Advance Online Publication, pp. 1-5, (Dec. 13, 2009).
Timmer et al, "Ammonia sensors and their applications—a review", Sensors and Actuators B, vol. 107, pp. 666-677, (Mar. 16, 2005).
Tomchenko et al, "Detection of chemical warfare agents using nanostructured metal oxide sensors", Sensors and Actuators B, vol. 108, pp. 41-55, (2005).
Wang et al, "Metal Oxide Gas Sensors: Sensitivity and Influencing Factors", Sensors, vol. 10, pp. 2088-2106, (Mar. 15, 2010).

(56) References Cited

OTHER PUBLICATIONS

White et al, "Solid-State, Dye-Labeled DNA Detects Volatile Compounds in the Vapor Phase", PLoS Biology, vol. 6(1), pp. 0030-0036, (Jan. 2008).
Zhang et al, "An integrated chip for rapid, sensitive, and multiplexed detection of cardiac biomarkers from fingerprick blood", Biosensors and Bioelectronics, vol. 28, pp. 459-463, (Jul. 18, 2011).
Mascini et al, "Piezoelectric sensors for dioxins: a biomimetic approach", Biosensors and Bioelectronics, vol. 20, pp. 1203-1210, (Aug. 20, 2004).
Wu et al, "Exploring the recognized bio-mimicry materials for gas sensing", Biosensors & Bioelectronics, vol. 16, pp. 945-953, (2001).
Wu et al, "Synthetic peptide mimicking of binding sites on olfactory receptor protein for use in 'electronic nose'", J Biotechnol, vol. 80, pp. 63-73, (2000).
Pevzner et al., "Knocking down highly-ordered large-scale nanowire arrays", Nano Lett. vol. 10, pp. 1202-1208, (2010).
Stern et al., "Semiconductin nanowire field-effect transistor biomolecular sensors", IEEE Trans. Electron Devices, vol. 55, No. 11, pp. 3119-3130, (2008).
Comini et al., "Metal oxide nanowires as chemical sensors", Materials Today, vol. 13, No. 7-8, pp. 36-44 (2010).
Liu et al, "A Survey on Gas Sensing Technology", Sensors, vol. 12, pp. 9635-9665, (Jul. 16, 2012).
Fine et al, "Metal Oxide Semi-Conductor Gas Sensors in Environmental Monitoring", Sensors, vol. 10, pp. 5469-5502, (Jun. 1, 2010).
Gao et al, "Light directed massively parallel on-chip synthesis of peptide arrays with t-Boc chemistry", Proteomics, vol. 3, pp. 2135-2141, (2003).
Yoon, "Current Trends in Sensors Based on Conducting Polymer Nanomaterials", Nanomaterials, vol. 2013 (3), pp. 524-529.
Ju et al, "Single-carbon discrimination by selected peptides for individual detection of volatile organic compounds", Scientific Reports, vol. 5, Article No. 9196, pp. 1-6, (Mar. 17, 2015).
Arrieta A et al, "Voltammetric sensor array based on conducting polymer-modified electrodes for the discrimination of liquids" vol. 49, No. 26, pp. 4543-4551, Oct. 15, 2004.
Ghanashyam Acharya et al, "Rapid Detection of S-Adenosyl Homocysteine Using Self-Assembled Optical Diffraction Gratings" vol. 47, No. 6, pp. 1051-1053, Jan. 25, 2008.
Pouthas F et al, "DNA detection on transistor arrays following mutation-specific enzymatic amplification", vol. 84, No. 9, pp. 1594-1596, Mar. 1, 2004.
Arjang Hassibi et al, "A Programmable 0.18-CMOS Electrochemical Sensor Microarray for Biomolecular Detection", vol. 6, No. 6, pp. 1380-1388, Dec. 1, 2006.
Kodoyianni, "Label-free analysis of biomolecular interactions using SPR imaging", Biotechniques vol. 50:(1), pp. 32-40, 2011.
Mohd Azmi et al., "Highly sensitive covalently functionalised integrated silicon nanowire biosensor devices for detection of cancer risk biomarker", Biosensors and Bioelectronics, vol. 52, pp. 216-224, (Sep. 3, 2013).
Lichtenstein et al, "Supersensitive fingerprinting of explosives by chemically modified nanosensors arrays", Nature Communications., vol. 5, pp. 4195-4207, (Jun. 24, 2014).
Xiao et al, "Label-Free Electronic Detection of Thrombin in Blood Serum by Using an Aptamer-Based Sensor", Angew. Chem. Int. Ed., vol. 44, pp. 5456-5459, (2005).
PCT International Searching Authority; International Search Report and Written Opinion of the International Searching Authority issued in PCT Application PCT/US2012/030133, dated Jul. 18, 2012, pp. 1-14.
Office Action issued in U.S. Appl. No. 15/372,343, dated Feb. 1, 2018.
Response to Office Action filed in U.S. Appl. No. 15/372,343, filed May 27, 2018.
Office Action issued in U.S. Appl. No. 15/372,248, dated Feb. 1, 2018.
Response to Office Action filed in U.S. Appl. No. 15/372,248, filed May 27, 2018.
Office Action issued in U.S. Appl. No. 15/372,343, dated Aug. 27, 2018.
Office Action issued in U.S. Appl. No. 15/372,248, dated Aug. 27, 2018.
Office Action issued in U.S. Appl. No. 15/372,248, dated Apr. 1, 2018.
Office Action issued in U.S. Appl. No. 15/372,343, dated Apr. 8, 2018.
Xie, et al., "Gas sensor arrays based on polymer-carbon black to detect organic vapors at low concentration", Sensors and Actuators B, vol. 113, pp. 887-891, (Aug. 24, 2005).
Ryan et al., "Polymer-carbon black composite sensors in an electronic nose for air-quality monitoring", MRS Bulletin, Oct. 2004 vol. 29(10): pp. 714-719, (Oct. 2004).

* cited by examiner

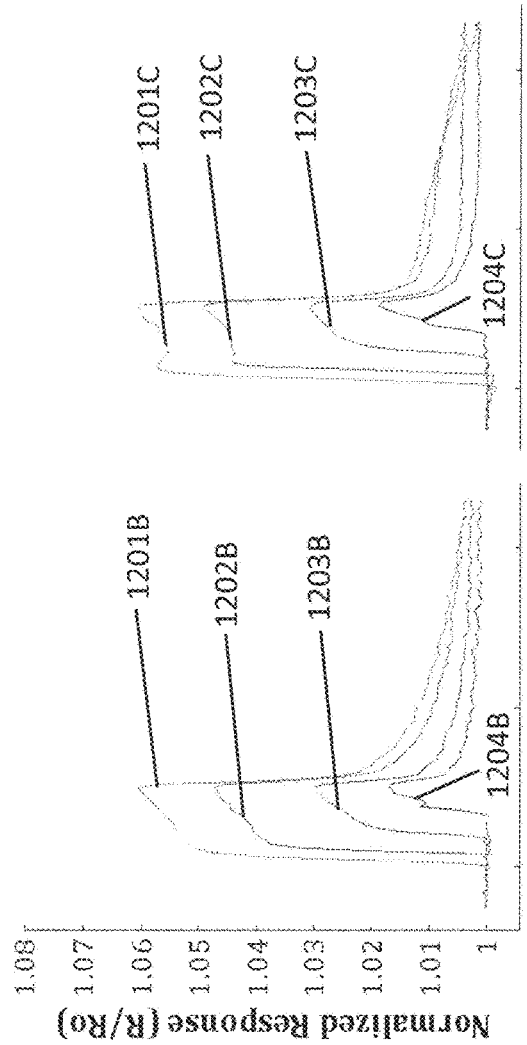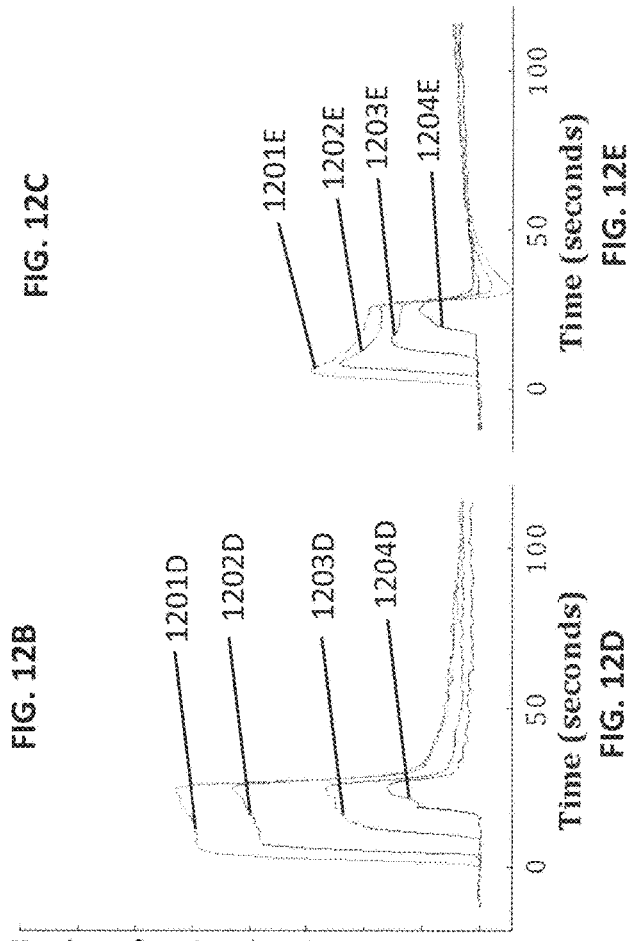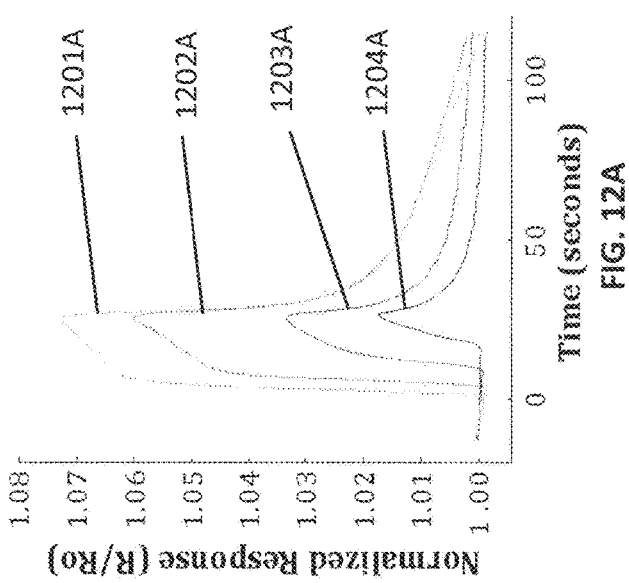
FIG. 12A  FIG. 12B  FIG. 12C  FIG. 12D  FIG. 12E

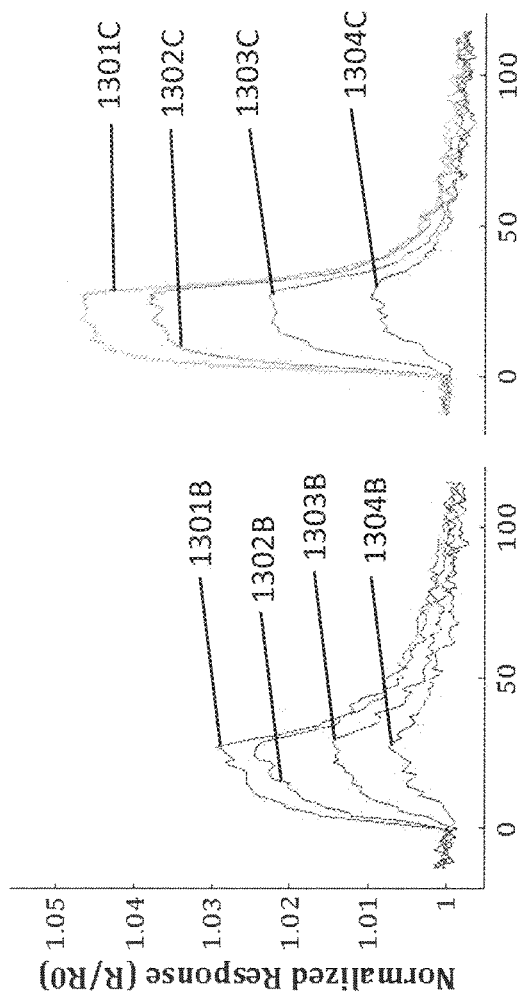
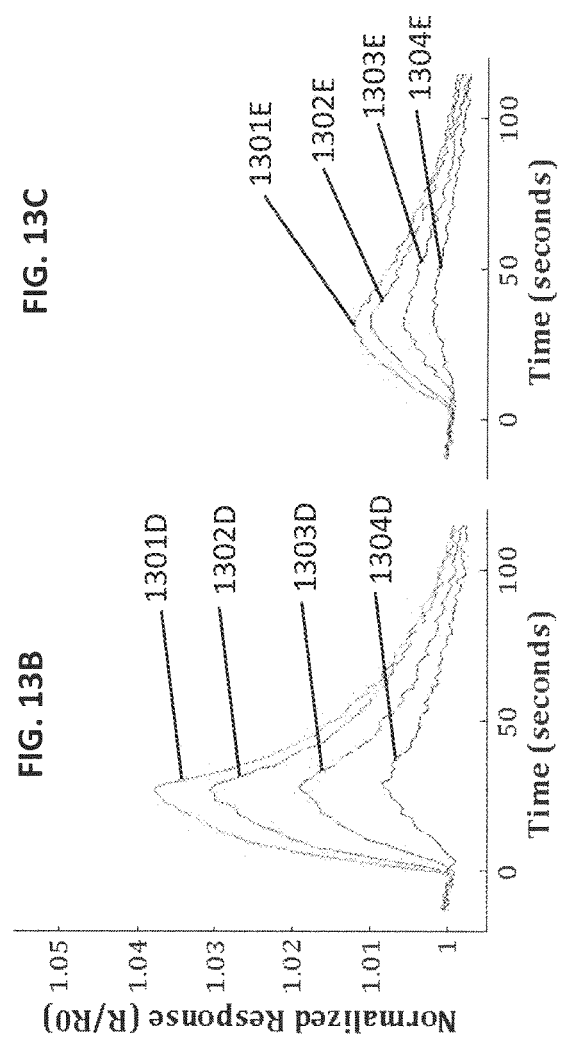
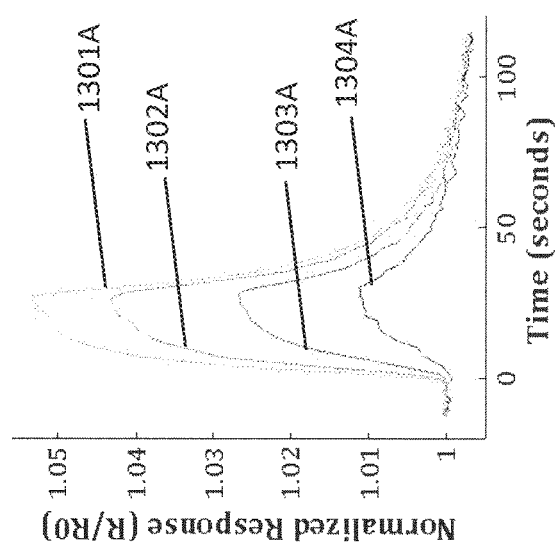
FIG. 13A, FIG. 13B, FIG. 13C, FIG. 13D, FIG. 13E

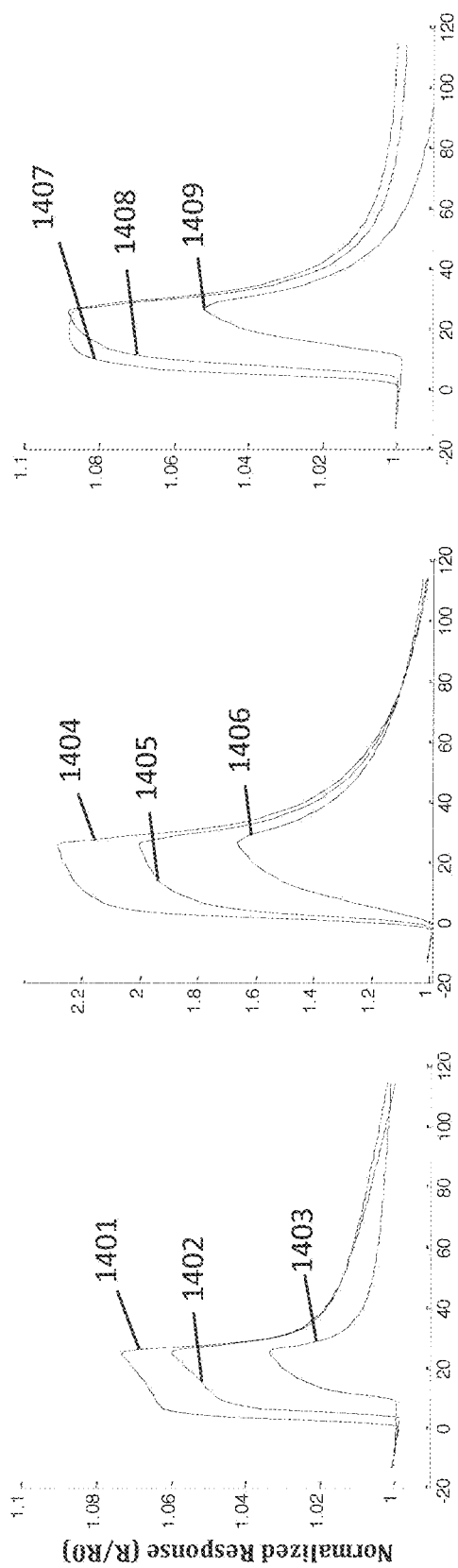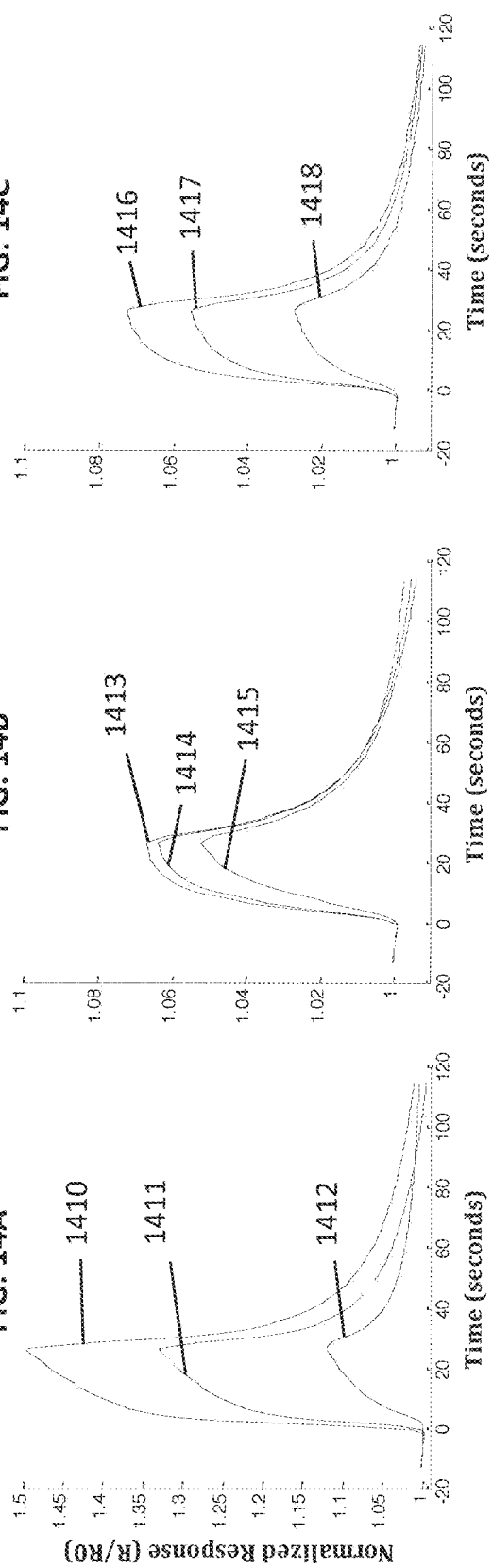

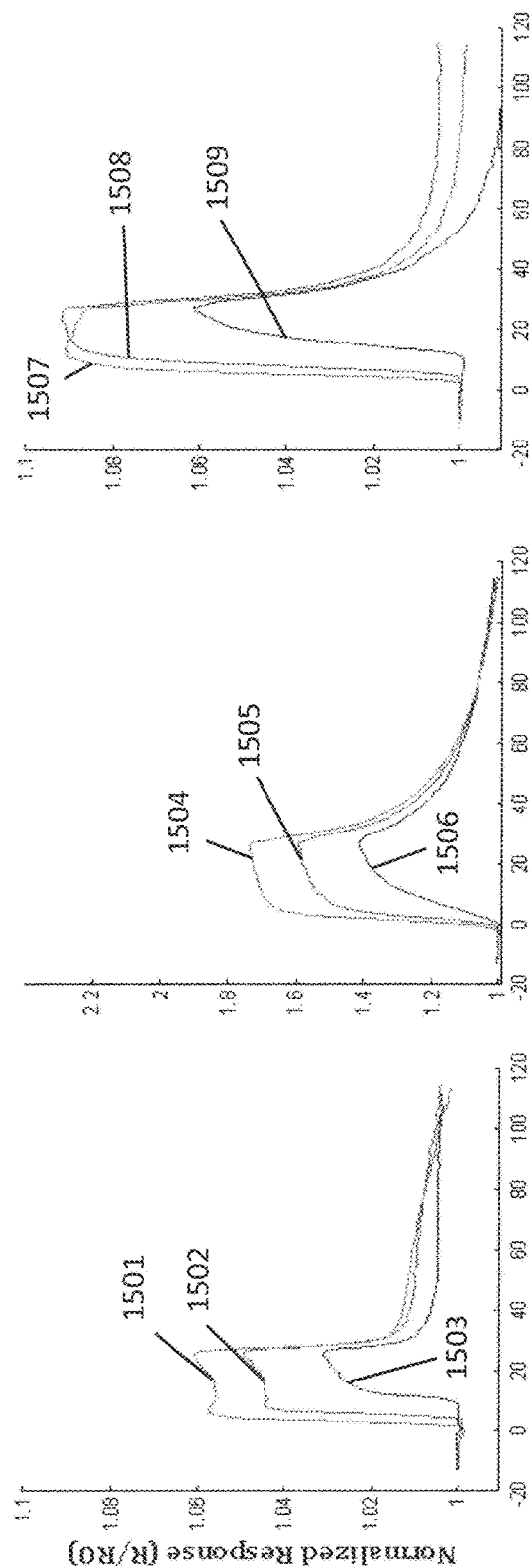

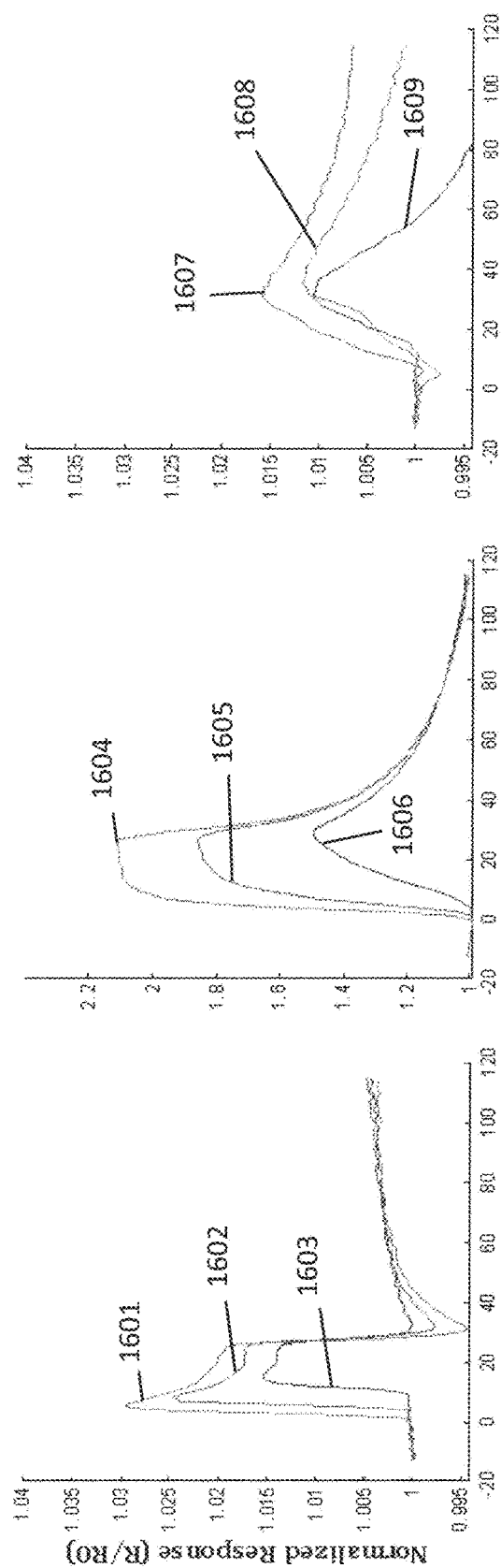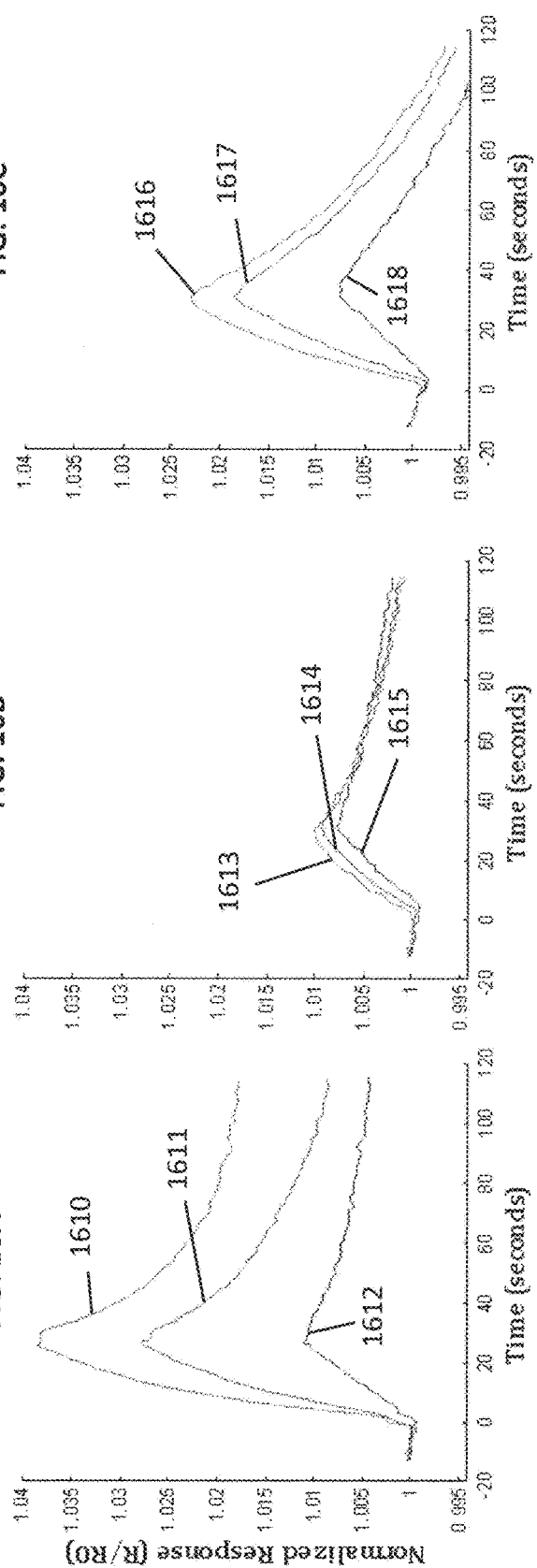

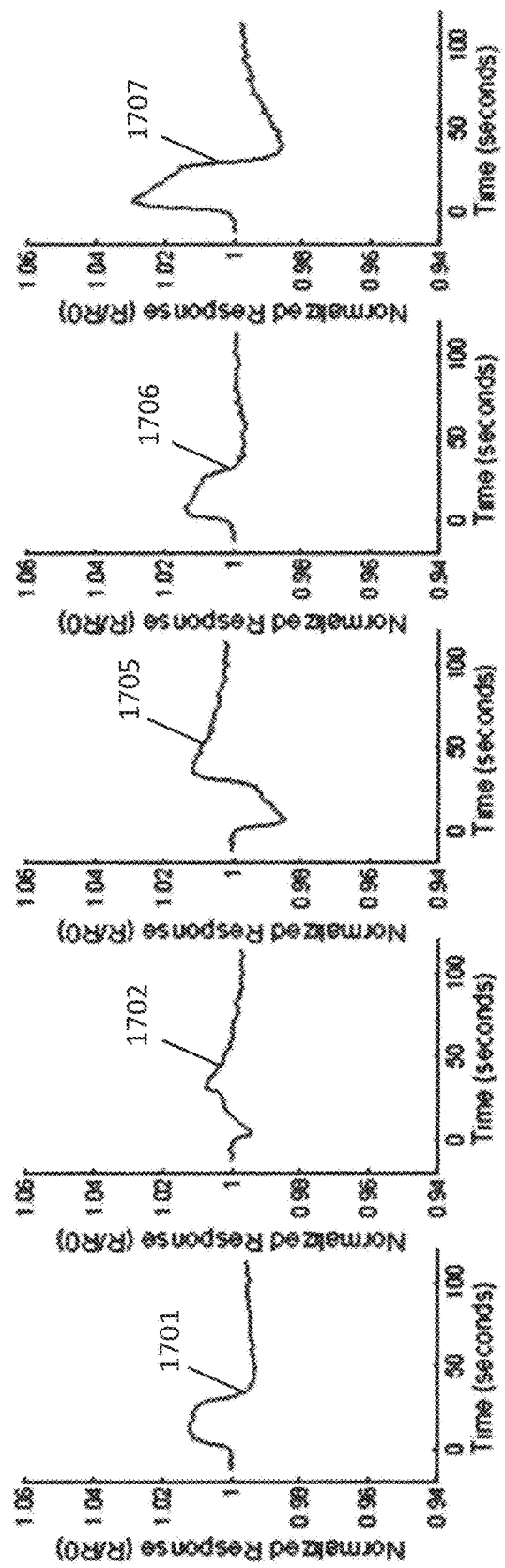

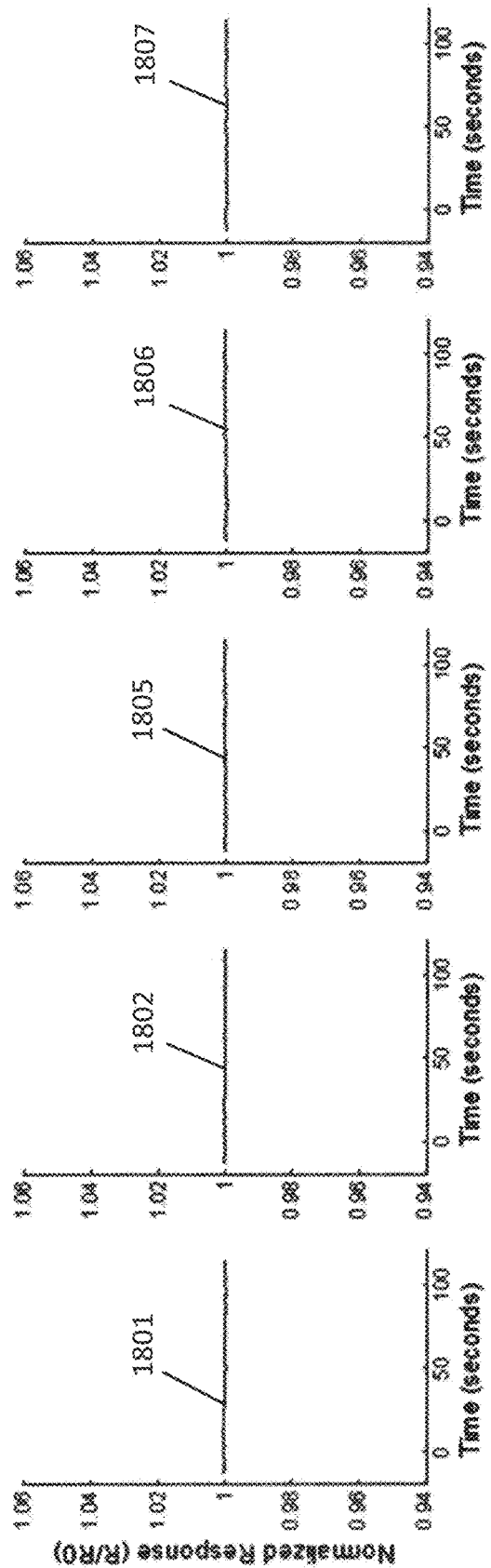
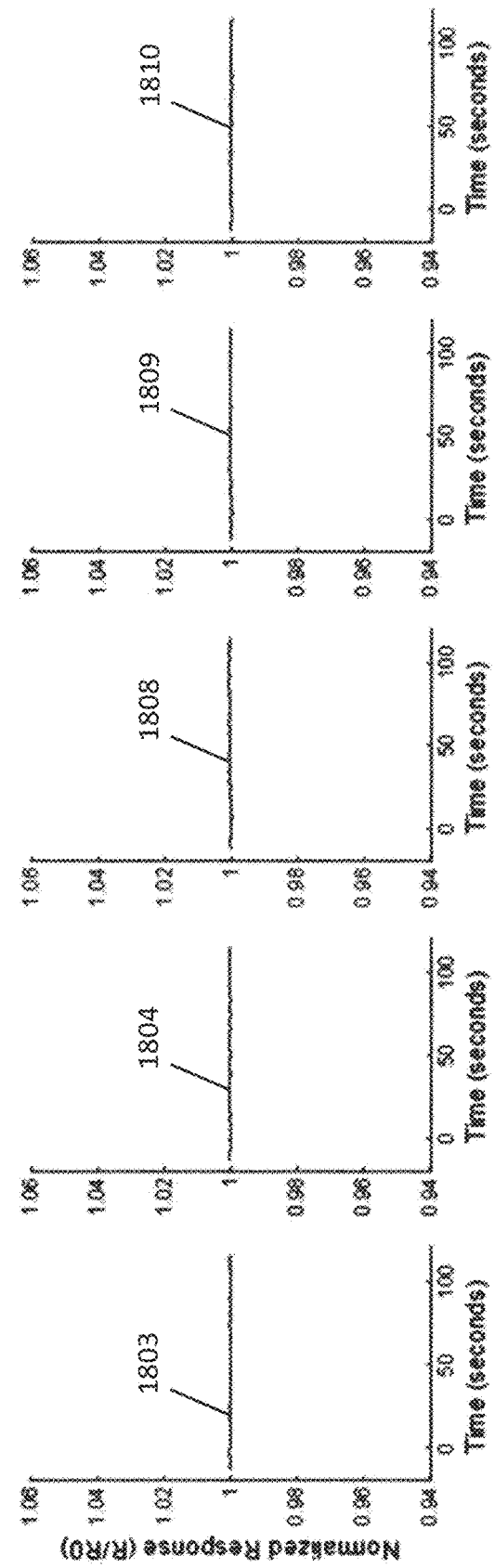
FIG. 18A — 1801
FIG. 18B — 1802
FIG. 18C — 1803
FIG. 18D — 1804
FIG. 18E — 1805
FIG. 18F — 1806
FIG. 18G — 1807
FIG. 18H — 1808
FIG. 18I — 1809
FIG. 18J — 1810

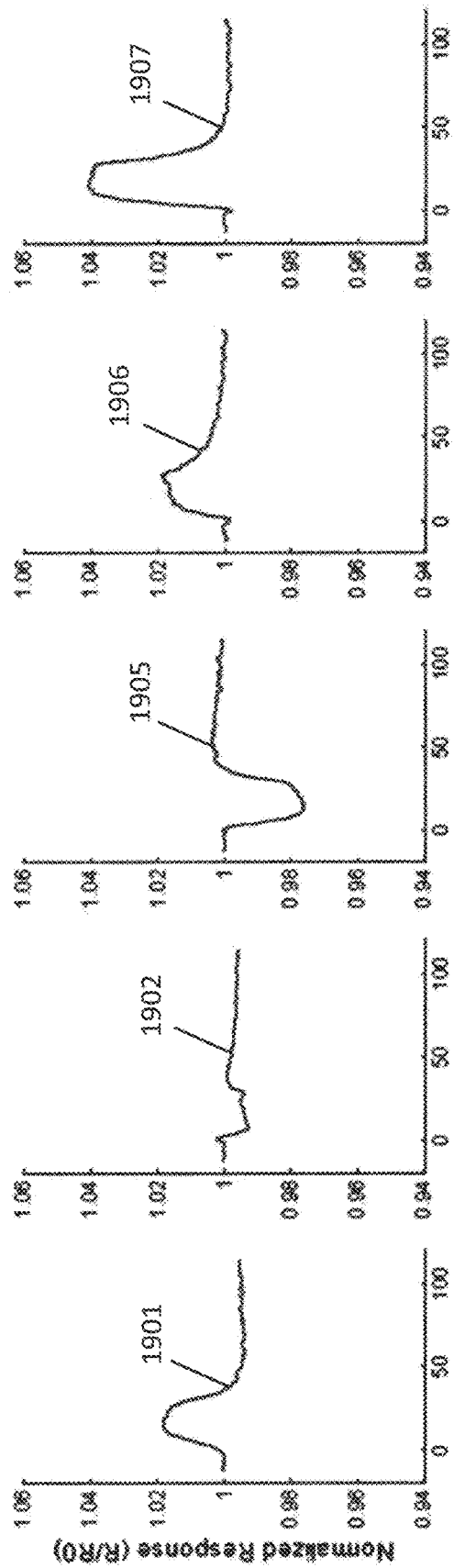
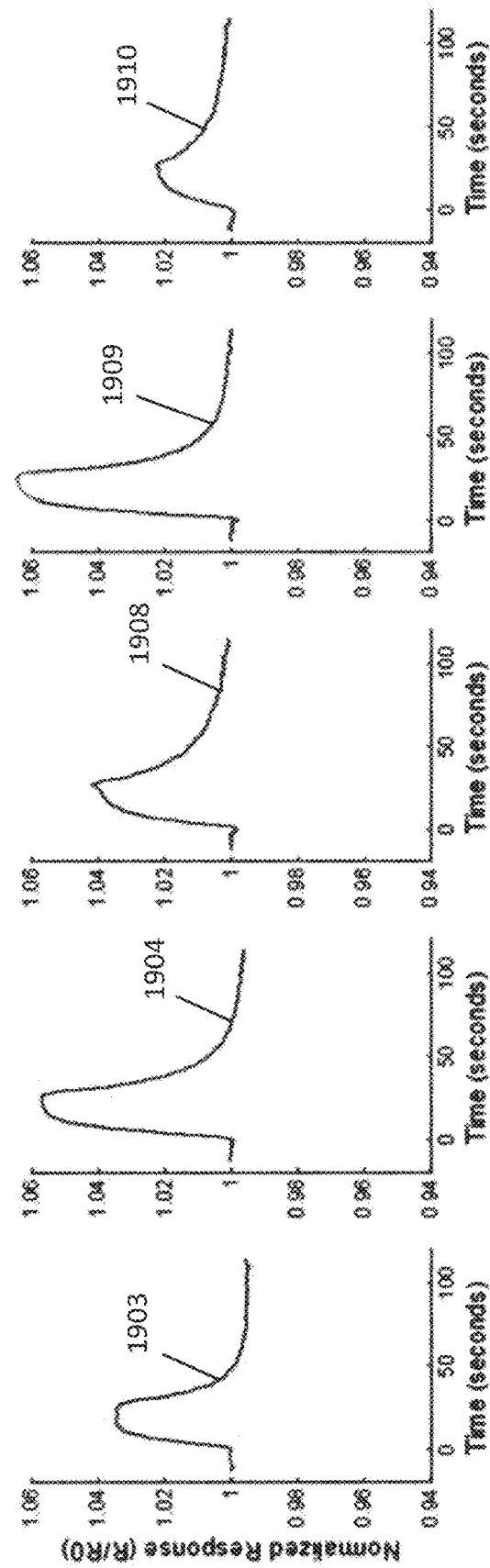

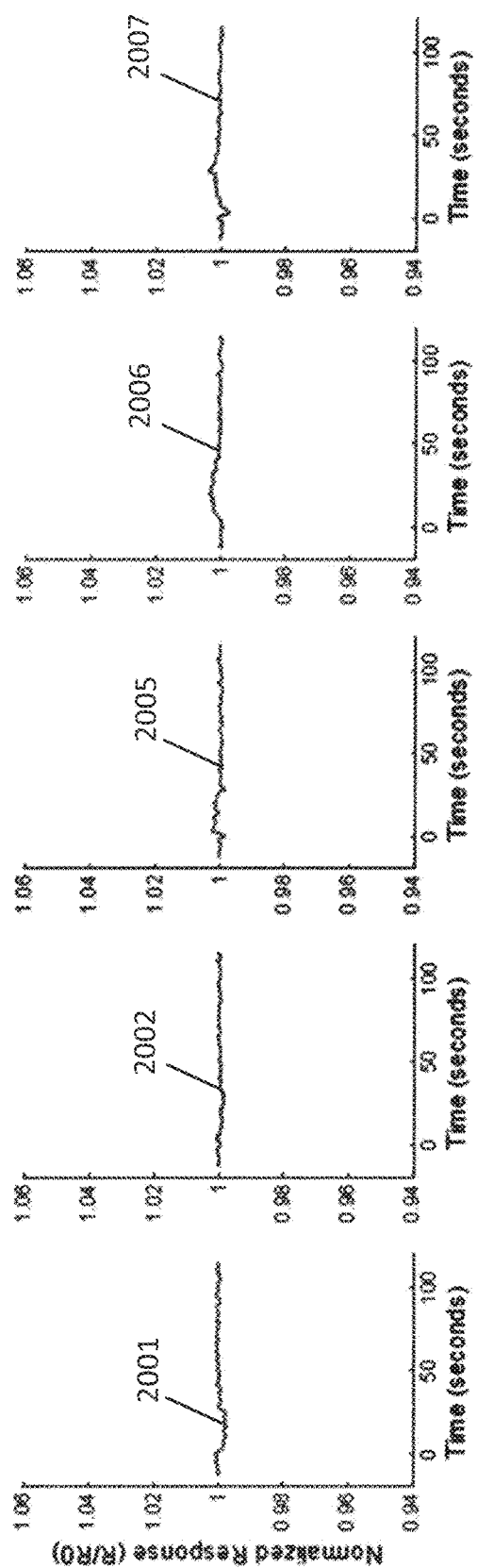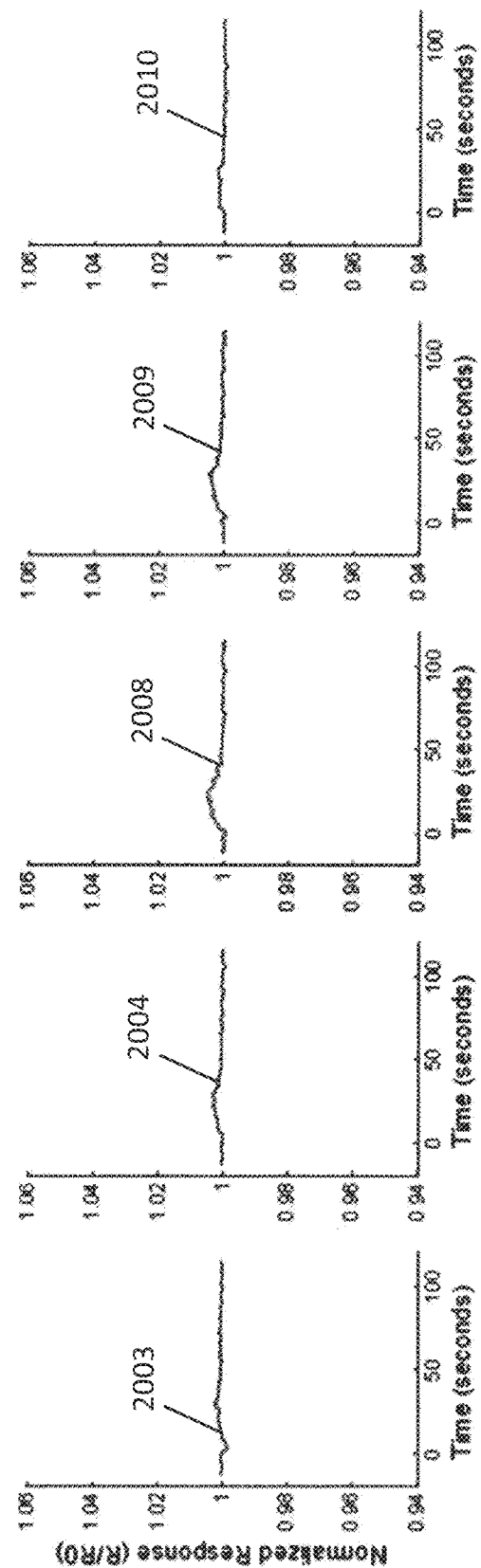

METHODS FOR DETECTING AND QUANTIFYING GAS SPECIES ANALYTES USING DIFFERENTIAL GAS SPECIES DIFFUSION

This application claims priority under 35 U.S.C. §119 to U.S. Provisional Application No. 62/263,768 filed Dec. 7, 2015, which is incorporated by reference herein in its entirety.

STATEMENT REGARDING FEDERALLY SPONSORED RESEARCH

The invention was made, in part, with government support under Contract FA8650-10-C-6126 awarded by the U.S. Air Force. The government has certain rights in the invention.

FIELD OF THE INVENTION

The invention is related to the detection and quantification of gases including volatile organic compounds. Some applications of the invention include the use of methods and sensors of the invention for detection and quantification of gas species in a test sample.

GENERAL DESCRIPTION

Detection and quantification of gases are useful in numerous applications including for example, evaluating air samples for the presence of hazardous gases, determining safety of air samples for human respiration, and monitoring gas production, solvent evaporation, reaction progress, and end-product yield during industrial chemical production and petrochemical refining. Other exemplary uses include characterizing human-specific volatile organic compounds (e.g., in breath samples) for evaluating various health factors, diagnosing conditions or diseases, determining identity, and examining performance factors such as stress or fatigue.

Methods and instrumentation for detection of gases have been previously described and include mass spectrometry, optical absorption, infrared spectroscopy and assaying with semiconducting metal oxide sensors, to name a few. Many methods currently in use require bulky instrumentation and vacuum chambers and may consume large amounts of power.

Gas nanosensors that have been previously described often lack selectivity and detect most or all gas species that bind to the surface of the sensor. Methods for increasing specificity in gas detection include the use of filter layers for excluding certain gas species while permitting other gas species to interact with a detector, the use of detectors that are specific for certain gases, and the use of surface-attached molecules that bind specific gas targets, wherein binding of a target gas species to the surface-attached molecule causes a nanosensor response.

Metal oxide semiconductor type sensors, also known as Taguchi type sensors (U.S. Pat. No. 3,695,848), are capable of providing rapid and real time detection of gases. Fine et al., (2010 Sensors 10:5469-5502), Liu et al., (2012 Sensors 12(7):9635-9665), and Huang et al., (2009 Sensors 9:9903-9924) describe fabrication and operation of Taguchi type sensors and are incorporated by reference herein in their entirety. Absorption or desorption of a gas on the surface of a metal oxide (e.g., $SnO_2$, $ZnO$, $TiO_2$, $In_2O_3$, and $CuO$) changes the conductivity of the metal oxide material allowing for detection and quantification of gas species. Metal oxide semiconductor nanosensors and monolithic arrays of semiconducting nanosensors fabricated on the same substrate, such as the imprinted nanotrace nanosensors and arrays described in Savoy et al., (U.S. Patent App. Pub. No. 2012/0178199A1 and U.S. Pat. No. 8,450,131, both of which are incorporated by reference herein in their entirety), are useful in embodiments of the invention and demonstrate rapid, high sensitivity detection times for gas analytes.

Embodiments of the invention include sensors, detectors, methods, and reagents that enable the detection, identification, and/or quantification of different gas analyte species that are present in a test sample. In some embodiments of the invention, methods include determining a response profile of a gas sensor to interaction of a gas with the sensor. A gas sensor response profile determined with one or more known (control) gas species, is a "control gas sensor response profile", and a gas sensor response profile determined with a test gas sample is a "test sample sensor response profile". A response profile of a gas sensor, or an array of sensors, is determined for selected time periods, ranging from a selected time before exposure of a sensor to a gas sample to a selected time after stopping exposure of a gas sample.

In some embodiments of the invention, a gas sensor response profile is determined with a gas sensor that is derivatized with a diffusion matrix (i.e., the sensor is a "derivatized sensor"). In some aspects of the invention, a diffusion matrix comprises a molecule, a molecular compound (covalent compound), a biomolecule, or an ionic compound that is coupled to a gas sensor surface and that interacts non-specifically with a gas molecule during diffusion of the gas molecule to the gas sensor. A diffusion matrix may be coupled to a porous matrix that is on a gas sensor. In some embodiments of the invention, a derivatized gas sensor exhibits a response to a gas, upon interaction of the gas with the sensor, that is different when compared with a sensor response to the gas exhibited upon interaction of the gas with a sensor lacking a diffusion matrix (underivatized sensor) or when compared with a sensor response to the gas exhibited upon interaction of the gas with a sensor derivatized with a different diffusion matrix. Without being bound by theory, in some aspects of the invention, molecules or compounds that are present on a sensor surface may alter the diffusion rate of gas molecules to the sensor surface when the sensor is exposed to a gas sample. Furthermore, these alterations of the gas diffusion rate occur in a predictable manner. A gas sensor response profile is affected by the diffusion rate by Fick's law, the absorption rate of gas molecules onto the surface of the sensor, the desorption rate of the gas molecules from the surface of the sensor travelling through the diffusion matrix, and the overall effect of the surface-adsorbed gas molecules on the charge carrier concentration and mobility (i.e., electric current) in the gas sensor.

In embodiments of the invention, comparison of one or more control gas sensor response profiles with one or more test sample sensor response profiles is used to detect, identify, and/or quantify one or more selected gas species analyte present in a test sample. Methods of detecting a gas species analyte in a test sample typically comprise exposing a gas sensor, derivatized with a diffusion matrix, to a control sample comprising a known, selected gas species analyte and determining a control sensor response profile; exposing the gas sensor to a test sample and determining a test sample sensor response profile; and determining the presence or absence of the gas species analyte in the test sample by comparing the test sample sensor response profile and the control sample sensor response profile.

In some aspects of the invention, test sample and control gas sensor response profiles for comparison are determined under a variety of different conditions, such as for example, with sensors that are derivatized with different types of diffusion matrices, with different concentrations of gases in a gas phase or in a vapor phase of a liquid or solid and/or with multiple different gas species separately or combined in a single sample. In further embodiments of the invention, detecting, identifying, and/or quantifying a selected gas species analyte in a test sample comprises comparing a test sample sensor response profile, determined using a sensor having a specific selected type of diffusion matrix, with a control sample sensor response profile determined using the same type of sensor and diffusion matrix. In further aspects of the invention, identification of a plurality of selected gas species in a test sample comprises comparing a test sample sensor response profile determined using a sensor derivatized with a specific type of diffusion matrix with one or more control gas sensor response profiles determined with the same type of sensor and diffusion matrix and with the selected gas species of interest. In additional embodiments of the invention, a control gas sensor response profile may be determined using the same sensor as that used for a test sample sensor response, but prior to determining the sensor response profile with the test gas sample. Comparisons of control sample and test sample gas sensor response profiles determined under a variety of conditions enable, contribute to, and enhance detection, identification, and quantification of a gas analyte in a test sample. In additional aspects of the invention, multiple gas sensor profiles are determined with a test sample or with a control gas sample comprising one or more control gas species. In further embodiments of the invention a test sample sensor response profile or a control sample sensor response profile is determined with an underivatized sensor, and the response profile of the underivatized sensor is stored in a database.

In certain embodiments of the invention multiple sensor response profiles are determined with a single test sample or a portion of the same test sample. As used herein, the term "test sample" also refers to a portion of a test sample that is analyzed. In some embodiments of the invention a test sample may comprise a gas or a liquid, a solid, a biological sample, or an environmental sample with a corresponding vapor component or gas phase. In additional embodiments of the invention a test sample may be a vapor phase or gas phase of a solid or liquid.

In some aspects of the invention, one or more control gas sensor response profiles and test sample sensor response profiles are stored in a database, and comparing sensor response profiles comprises comparing one or more test sample response profiles to one or more control gas response profiles stored in the database. In additional aspects of the invention, deconvolution of gas sensor response data enables the identification and quantification of gases in a test sample.

Other embodiments of the invention are discussed throughout this application. Embodiments described herein are understood to be applicable to all aspects of the invention. It is contemplated that any embodiment discussed herein can be implemented with respect to any method or composition of the invention, and vice versa. Furthermore, compositions of the invention can be used to achieve methods of the invention.

The specification is most thoroughly understood in light of the teachings and references cited within the specification. It should be understood that the drawings, detailed description, and specific examples, while indicating specific embodiments of the invention, are given by way of illustration only, since various changes and modifications within the spirit and scope of the invention will become apparent from this detailed description to those skilled in the art.

Any section headings used herein are for organizational purposes only and are not to be construed as limiting the subject matter described. All documents, or portions of documents, cited in this application, including but not limited to patents, patent applications, articles, books, and treatises, are hereby expressly incorporated by reference herein in their entirety for any purpose. To the extent documents, publications, patents, or patent application publications incorporated by reference contradict the invention contained in the specification, the specification will supersede any contradictory material.

BRIEF DESCRIPTION OF THE FIGURES

The following drawings form part of the present specification and are included to further demonstrate certain aspects of the invention. The invention may be better understood by reference to one or more of these drawings in combination with the detailed description of the specification embodiments presented herein.

FIG. 7A shows multiple gas sensor response profiles, determined using a sensor derivatized with linker structures, for each of seven different volatile organic gas analytes from common industrial solvents. FIG. 7B shows the averaged gas sensor response profile from all sensors for each gas. FIG. 7C and FIG. 7D show principal component analysis plots using data from the gas sensor response profiles.

FIG. 8A and FIG. 8B illustrate concentration profile curves representing the concentration distribution of a gas analyte between a gas source and a sensor derivatized with an exemplary biomolecular diffusion matrix, during gas exposure and diffusion of gas analytes to the sensor (FIG. 8A) and after stopping gas exposure and during diffusion of gas analytes from the sensor (FIG. 8B). FIG. 8C shows the corresponding gas sensor response profile and the position in time corresponding to each concentration profile curve. In FIG. 8A and FIG. 8B, for ease of viewing, diffusion matrices are shown as shaded rectangles and the gas analyte is represented as horizontal arrows. Concentration (arb.) (y-axis), refers to concentration represented as arbitrary units. Distances from gas source (x-axis) are in arbitrary units.

FIG. 10A and FIG. 10B illustrate concentration profile curve simulations representing the concentration distribution of a gas analyte between a gas source and a sensor derivatized with one type of exemplary biomolecular diffusion matrix. FIG. 10A shows concentration profile curves during gas exposure and diffusion of gas analytes to the sensor. FIG. 10B shows concentration profiles curves after stopping gas exposure and during diffusion of gas analytes from the sensor. FIG. 10C and FIG. 10D illustrate concentration profile curves representing the concentration distribution of the same gas analyte between a gas source and a sensor derivatized with a different type of exemplary biomolecular diffusion matrix. FIG. 10C shows concentration profile curves during gas exposure and diffusion of gas analytes to the sensor, and FIG. 10D shows concentration profiles curves after stopping gas exposure and during diffusion of gas analytes from the sensor. For ease of viewing, the biomolecular diffusion matrices are shown as shaded rectangles and the gas analyte is represented as horizontal arrows. Concentration (arb.) refers to concentration represented as arbitrary units. Distances from gas source (x-axis) are in arbitrary units.

FIG. 12A-FIG. 12E show five series of gas sensor response profiles in response to the gas analyte acetone, each series determined with a gas sensor derivatized with a different type of diffusion matrix. All y-axes represent normalized response (R/R$_0$), and all x-axes represent time (seconds).

FIG. 13A-FIG. 13E show five series of gas sensor response profiles in response to the gas analyte xylene, each series determined with a gas sensor derivatized with a different type of diffusion matrix. All y-axes represent normalized response (R/R$_0$), and all x-axes represent time (seconds).

FIG. 14A-FIG. 14F show six series of gas sensor response profiles, determined using silane-derivatized sensors in response to six different gas analytes, each analyte at three different concentrations of saturated gas vapor pressure. FIG. 14A, acetone; FIG. 14B, ammonia; FIG. 14C, dimethylacetophenone; FIG. 14D, N-methyl-2-pyrrolidone; FIG. 14E, toluene; FIG. 14F, xylene. Sensor response profiles plotted in each of FIG. 14A-FIG. 14F represent the average of multiple sensor response profiles determined for each gas concentration. All y-axes represent normalized response (R/R$_0$), and all x-axes represent time (seconds).

FIG. 15A-FIG. 15F show six series of gas sensor response profiles, determined using sensors derivatized with the 8-mer peptide RVNEWVID as a diffusion matrix, in response to six different gas analytes, each analyte at three different concentrations of saturated gas vapor pressure. FIG. 15A, acetone; FIG. 15B, ammonia; FIG. 15C, dimethylacetophenone; FIG. 15D, N-methyl-2-pyrrolidone; FIG. 15E, toluene; FIG. 15F, xylene. Sensor response profiles plotted in each of FIG. 15A-FIG. 15F represent the average of multiple sensor response profiles determined for each gas concentration. All y-axes represent normalized response (R/R$_0$), and all x-axes represent time (seconds).

FIG. 16A-FIG. 16F show six series of gas sensor response profiles, determined using sensors derivatized with the relatively large protein anti-biotin antibody as a diffusion matrix, in response to six different gas analytes, each analyte at three different concentrations of saturated gas vapor pressure. FIG. 16A, acetone; FIG. 16B, ammonia; FIG. 16C, dimethylacetophenone; FIG. 16D, N-methyl-2-pyrrolidone; FIG. 16E, toluene; FIG. 16F, xylene. Sensor response profiles plotted in each of FIG. 16A-FIG. 16F represent the average of multiple sensor response profiles determined for each gas concentration. All y-axes represent normalized response (R/R$_0$), and all x-axes represent time (seconds).

FIG. 17A-FIG. 17J show ten ratiometric comparison plots of sensor response profiles determined after exposure of sensors to the gas analyte xylene. Sensor response profile ratios include FIG. 17A, linker-derivatized sensor to sensor derivatized with peptide DLESFLD (1701); FIG. 17B, linker-derivatized sensor to sensor derivatized with peptide RVNEWVID (1702); FIG. 17C, linker-derivatized sensor to sensor derivatized with BSA (1703); FIG. 17D, linker-derivatized sensor to sensor derivatized with anti-biotin (1704); FIG. 17E, sensor derivatized with peptide DLESFLD to sensor derivatized with peptide RVNEWVID (1705); FIG. 17F, sensor derivatized with peptide DLESFLD to sensor derivatized with BSA (1706); FIG. 17G, sensor derivatized with peptide DLESFLD to sensor derivatized with anti-biotin (1707); FIG. 17H, sensor derivatized with peptide RVNEWVID to sensor derivatized with BSA (1708); FIG. 17I, sensor derivatized with peptide RVNEWVID to sensor derivatized with anti-biotin (1709); FIG. 17J, sensor derivatized with BSA to sensor derivatized with anti-biotin (1710). All y-axes represent normalized response (R/R$_0$), and all x-axes represent time (seconds).

FIG. 18A-FIG. 18J show ten ratiometric comparison plots of sensor response profiles determined after exposure of sensors to the gas analyte xylene. All sensors used in these examples were underivatized bare sensors (i.e., no silane linker treatment). The same sensors as were described in the description for FIG. 17A-FIG. 17J were exposed to xylene, but here, gas exposure to the underivatized bare sensors occurred prior to the coupling of the biomolecular diffusion matrices to the sensors or prior to any silane treatment of sensors. All y-axes represent normalized response (R/R$_0$), and all x-axes represent time (seconds).

FIG. 19A-FIG. 19J show ten ratiometric comparison plots of sensor response profiles determined after exposure of sensors to the gas analyte toluene. Sensor response profile ratios include FIG. 19A, linker-derivatized sensor to sensor derivatized with peptide DLESFLD (1901); FIG. 19B, linker-derivatized sensor to sensor derivatized with peptide RVNEWVID (1902); FIG. 19C, linker-derivatized sensor to sensor derivatized with BSA (1903); FIG. 19D, linker-derivatized sensor to sensor derivatized with anti-biotin (1904); FIG. 19E, sensor derivatized with peptide DLESFLD to sensor derivatized with peptide RVNEWVID (1905); FIG. 19F, sensor derivatized with peptide DLESFLD to sensor derivatized with BSA (1906); FIG. 19G, sensor derivatized with peptide DLESFLD to sensor derivatized with anti-biotin (1907); FIG. 19H, sensor derivatized with peptide RVNEWVID to sensor derivatized with BSA (1908); FIG. 19I, sensor derivatized with peptide RVNEWVID to sensor derivatized with anti-biotin (1909); FIG. 19J, sensor derivatized with BSA to sensor derivatized with anti-biotin (1910). All y-axes represent normalized response ($R/R_0$), and all x-axes represent time (seconds).

FIG. 20A-FIG. 20J show ten ratiometric comparison plots of sensor response profiles determined after exposure of sensors to the gas analyte toluene. All sensors used in these examples were underivatized bare sensors (i.e., no silane linker treatment). The same sensors as were described in the description for FIG. 19A-FIG. 19J were exposed to toluene, but here, gas exposure to the underivatized bare sensors occurred prior to the coupling of the biomolecular diffusion matrices to the sensors or prior to any silane treatment of sensors. All y-axes represent normalized response ($R/R_0$), and all x-axes represent time (seconds).

FIG. 23A shows an exemplary embodiment of a region of a gas analyte nanosensor fabricated using the method of nanoimprint lithography. FIG. 23B shows an enlargement of a section of the nanosensor having semiconducting metal oxide nanotraces with a schematic illustration of a diffusion matrix on one nanotrace of the sensor. Scale bar in FIG. 23A=400 nm.

DESCRIPTION OF CERTAIN EXEMPLARY EMBODIMENTS

Figure 1A:
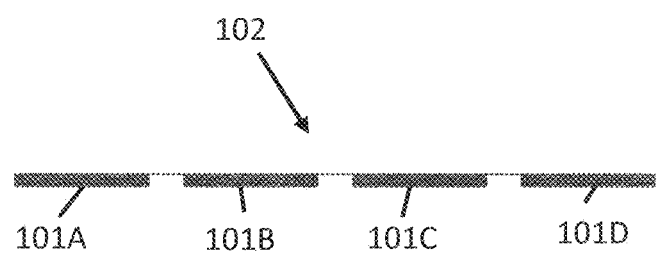
FIG. 1A-FIG. 1D is a schematic depiction of an exemplary embodiment of the invention for detecting a gas species analyte using different diffusion matrices coupled to gas sensors present as an array of sensors.

Reference will now be made in detail to certain exemplary embodiments of the invention, some of which are illustrated in the accompanying drawings. To assist in understanding the present invention, certain terms are first defined. Additional definitions are provided throughout the application.

The use of the word "a" or "an" when used in conjunction with the term "comprising" in the claims or the specification may mean "one," but it is also consistent with the meaning of "one or more," "at least one," and "one or more than one." The use of the term "at least one" in the specification and claims is meant to include "one or more than one", and the use of the term "one or more than one" is meant to include "at least one".

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Disclosed herein are methods, compositions, and sensors for the detection and quantification of a gas analyte in a test sample. As used herein, the terms "gas analyte", "gas species", and "gas species analyte", are used interchangeably and encompass different "types" or "species" of gases that are present in a control sample or a test sample. By way of example, gaseous oxygen and gaseous nitrogen are different gas species, gas types, or gas species analytes. The presence of one or more gas species in a test sample may be determined, and the amounts of one or more gas species may be quantified using methods and compositions of the invention. In embodiments of the invention, determining the presence of a gas analyte may include identifying the type or species of the gas analyte. As used herein, "gas sample" may be used to refer to a gas "test sample" or a gas "control sample". Generally, "test sample" refers to a sample that is analyzed to determine the presence of, identity of, and/or quantity of one or more selected gas species analytes in the sample, and "control sample" refers to a sample having one or more known, selected gas species analytes. In some embodiments of the invention, the concentration of a gas analyte in a control sample is also known. In additional embodiments of the invention, known gas species may be added to a test gas sample. When referring to gases in a control sample, the term "a plurality of known gas species analytes" means that the gas sample has at least two different types or species of known gases in the sample. Similarly, the term "one or more known gas species analytes" means that the sample has at least one known species or type of gas, and the sample may have at least two different types or species of known gases. In some embodiments of the invention, known gas species in a control sample are selected based on the gas species to be detected on analysis of a test sample.

The terms "sensor", "gas sensor", "nanosensor", "gas detector", "detector" and combinations of these are used interchangeably and refer to a gas sensor, or a gas sensor surface that interacts with a gas molecule for detection.

As used herein, the terms "biomolecule" and "biomolecular" refer to a molecule that is produced or capable of being produced in or produced by a living organism. In some embodiments of the invention, a biomolecule is an organic molecule. Exemplary organic biomolecules include proteins, peptides; polypeptides, oligopeptides, amino acids, polysaccharides, nucleic acids, DNA, and RNA. Additional exemplary biomolecules include small molecule metabolites, cytokines, hormones, lipids, antibodies, sugars, acids, bases, and other chemical compounds. In some aspects of the invention, biomolecules may be primary or secondary metabolites, aptamers, or receptors. In additional aspects of the invention, a biomolecule refers to an organic or inorganic degradation product of a biomolecule.

Biomolecules useful in some embodiments of the invention may be isolated from an organism or may be synthetically prepared in vitro. In some aspects of the invention, a biomolecule is a fragment of a cell or a cell structure, such as for example only a region of a cell membrane, a fragment of a cell membrane, a liposome, or a cellular organelle such as a mitochondrion, a nucleus, a Golgi apparatus, or another subcellular structure. Biomolecules may be purified or partially purified during or following isolation from an organism. Numerous methods for isolating and purifying biomolecules are known to those of skill in the art. It is also contemplated that novel purification methods not yet known in the art could be used for purifying biomolecules for use in embodiments of the invention. In addition, methods for in vitro synthesis of biological small molecules, antibodies, peptides, nucleic acids, cell membranes, membrane mimics, liposomes, and other biological structures are known in the art.

The terms "diffusion matrix" and "molecular diffusion matrix", are used interchangeably and refer to a molecule, a molecular compound, an ionic compound, and pluralities thereof that are coupled to a gas sensor and that interact non-specifically with a gas molecule during diffusion of the gas molecule to the sensor surface. In embodiments of the invention, a diffusion matrix may modify the response profile of a gas sensor to a gas analyte as compared to a response profile of a sensor having no diffusion matrix or as compared to a response profile of a sensor derivatized with a different type of diffusion matrix. The "derivatization state" of a sensor refers to the presence or absence of a diffusion matrix or the type of diffusion matrix on a sensor. Exemplary types of diffusion matrices for use in some embodiments of the invention include matrices that comprise small molecules, polymers, or biomolecules. Different types of diffusion matrices may comprise different molecules, different combinations of molecules, or even different amounts of molecules.

In some embodiments of the invention, the terms "biomolecular diffusion matrix" and "biomolecular diffusion matrices" refer to a diffusion matrix that comprises biomolecules. Like other types of diffusion matrices, a biomolecular diffusion matrix present on a gas sensor surface may modify the response profile of a gas sensor to a gas analyte as compared to a response profile of a sensor having no biomolecular diffusion matrix or as compared to a response profile of a sensor derivatized with a different type of biomolecular diffusion matrix. In some embodiments of the invention, biomolecules present in biomolecular diffusion matrices are capable of non-specific chemical or electrostatic interaction with at least one gas species analyte in a gas sample. In additional embodiments of the invention, a gas sensor may be derivatized with a biomolecular diffusion matrix selected to have different non-specific chemical and/or electrostatic interactions with different gas species in a gas sample. In some aspects of the invention, a single gas sensor is derivatized with a single selected "type" of biomolecular diffusion matrix. The type of biomolecular diffusion matrix is determined by the biomolecule or biomolecules that make up the diffusion matrix. Different types of biomolecular diffusion matrices may comprise different biomolecules, different combinations of biomolecules, or even different amounts of biomolecules.

A diffusion matrix may be present on, bound to, or coupled to a gas sensor. In some aspects of the invention, a diffusion matrix is synthesized on a sensor surface. In some embodiments of the invention, a porous support matrix that is present on, bound to, or coupled to a sensor may be a diffusion matrix or may be modified further to form a different type of diffusion matrix.

In some embodiments of the invention, the presence of a diffusion matrix on a gas sensor surface alters the rate at which a gas analyte moves from a gas source to the gas sensor surface for detection, as compared to a sensor not having a diffusion matrix. In additional embodiments of the invention, a diffusion matrix on a gas sensor surface alters the rate at which a gas analyte diffuses away from a gas sensor after interaction of the analyte with the sensor, as compared to a sensor not having a diffusion matrix. In some aspects of the invention, different types of diffusion matrices may alter these rates of movement or diffusion differently. The terms "diffusion matrix-analyte complex" and "matrix-analyte complex" refer to any structure in which a gas analyte and a diffusion matrix are interacting prior to adsorption of the gas analyte to the sensor surface, or during desorption of the gas analyte from the sensor surface after exposure of the gas sensor to a gas sample is stopped.

Underivatized gas sensors are used in some embodiments of the invention. When referring to gas sensors, the terms "underivatized", "underivatized sensor", and "bare sensor" mean that the sensor lacks a diffusion matrix.

Typically, gas detectors or gas sensors useful in embodiments of the invention comprise structures having nanoscale dimensions. Exemplary structures known to a person of skill in the art include nanotubes, nanowires, nanorods, nanofibers, and nanotraces and are referred to herein generally as "nanostructures". Gas detectors that have nanostructures as gas sensors are referred to herein as "nanosensors", "gas nanosensors", or "nanodetectors". A nanostructure has at least one cross sectional dimension, at some point along its length that is less than about 1,000 nm (1 micron). In some embodiments of the invention gas sensors comprise nanostructures having cross-sectional dimensions less than about 500 nm, less than about 250 nm, less than about 100 nm, less than about 50 nm, less than about 10 nm, or less than about 5 nm. In some aspects of the invention, the cross-sectional dimension is from about 0.5 nm to about 1 nm or from about 1 nm to about 5 nm. In some embodiments of the invention, nanostructure lengths range from about 1 nm to about 100 microns, including any selected size range therebetween. Cross sectional dimensions of nanostructures may be any size in the ranges listed above, including the higher and lower limits listed. All size ranges described are inclusive of the lower and upper limit values. Size ranges within the larger ranges listed above are also contemplated to be useful in some embodiments of the invention. Specific size ranges may be useful in specific aspects of the invention.

In embodiments of the invention, materials useful for gas sensors should be amenable to the attachment of or coupling of a diffusion matrix to the sensor surface in a manner that preserves functionality of the matrix for transient, non-specific chemical or electrostatic interaction with a gas species analyte in a sample. Chemical interaction is defined as attraction or repulsion between chemical functional groups present on the molecules in a diffusion matrix and chemical functional groups present on a gas analyte. Similarly, electrostatic interaction is defined as attraction or repulsion between electrically charged groups present on the molecules in a diffusion matrix and electrically charged groups on the gas analyte.

Desirable materials for use in gas sensors include those that exhibit changes in parameters such as resistance, current, capacitance, or electrochemical potential upon interaction with a gas. By way of example only, nanostructure gas sensors comprising one or more of conductometric semiconductors, conducting polymers, non-conducting polymers, carbon composites, carbon nanotubes, and gold particles may be useful in embodiments of the invention (Savoy et al., U.S. Pat. No. 8,450,131; Hatchett and Josowicz, Chem Rev (2008) 108:746-769; Yoon, Nanomaterials (2013) 3:524-549.)

In some embodiments of the invention, a gas sensor may be a conductometric semiconducting metal oxide ($MO_x$) sensor. Mechanisms of gas detection by semiconducting $MO_x$ gas sensors useful in embodiments of the invention are known in the art and have recently been reviewed (Wang et al., Sensors (2010) 10:2088-2106; Liu et al., Sensors (2012) 12:9635-9665; Huang and Wan, Sensors (2009) 9:9903-9924; Fine et al., Sensors (2010) 10:5469-5502). Gas detection by these types of sensors is based on the detection of a change in electrical resistance or conductance caused by interaction of a gas molecule with the gas sensor surface. Methods for making conductometric semiconducting $MO_x$ gas sensors from various types of nanostructures are available to those with skill in the art. Methods and materials for making conductometric semiconducting $MO_x$ nanotrace sensors, using nanoimprint lithography techniques, including materials useful as sensor surfaces and substrates and nanosensor dimensions, are described in Savoy et al., U.S. Pat. No. 8,450,131, which is incorporated by reference herein in its entirety. $MO_x$ nanotrace sensors have greater surface area-to-volume ratios compared to thin films of thin film sensors, permitting rapid interfacial gas exchange compared to diffusion between bulk grain boundaries, thereby enabling the rapid collection of gas sensor response profiles. Furthermore, high surface area-to-volume dimensions can eliminate the need for repeated heat cycling of a gas sensor, which can degrade calibration over time as the grain structure changes. Temperature cycling above ~100° C. can also degrade biomolecules. In other embodiments of the invention, gas sensors may comprise materials other than, or in addition to, semiconducting metal oxides. Although $MO_x$ nanotrace sensors patterned by nanoimprint lithography have advantages in some aspects of the invention, in other aspects of the invention, nanostructure grain dimensions of thin film materials may also be useful as a gas detector. In some embodiments of the invention, methods of the invention may be implemented with sensors that are not nanoscale-dimensioned.

In some embodiments of the invention, gas nanosensors may be assembled into an array on a substrate. The number of nanosensors in an array can range from one to hundreds, to thousands, to millions, depending on the application and device parameters, such as the number of read-out circuits and the spatial dimension of the diffusion matrix footprint. The number of nanosensors in an array may include any number in the range from one to millions, including one and millions. Further embodiments may involve deposition of sensors on the surface of CMOS read-out integrated circuits which may comprise by way of example only, arrays of 3×3, 10×20, 40×60, 320×540, 640×480 VGA, 2056×1560 full size, 2592×3872 10 megapixel, and 3456×5184 18 megapixel. Gas sensors may be configured with aspect ratios of 1×2, 1×3, 1×4, 1×8, 1×32, 1×100, 1×500, 1×1000, 1×10,000, 2×3, 3×4, and 9×16. Nanosensors may be grouped together in any of a variety of numbers and array sizes and shapes. In some embodiments of the invention, selected nanosensors in an array can be employed as references and controls.

In embodiments of the invention, each sensor in an array may be derivatized with a selected type of diffusion matrix, or a sensor may be underivatized. In certain aspects of the invention, an array of sensors comprises a plurality of nanosensors, some of which may be derivatized with the same selected type of diffusion matrix. In additional aspects of the invention, multiple nanosensors derivatized with the same type of diffusion matrix may be grouped together on a selected region of an array. In still other aspects of the invention, an array of nanosensors may comprise multiple groups of nanosensors, each group derivatized with a different, selected type of diffusion matrix. In certain aspects of the invention, one or more gas sensors may not have a diffusion matrix, i.e., they are underivatized sensors. Exemplary methods for arranging nanosensors and groups of nanosensors on an array are described in Savoy et al., U.S. Pat. No. 8,450,131.

As used herein, in some embodiments of the invention, the terms "exposing" and "exposure" and variations thereof refer to exposing a gas sensor to a gas analyte species or to a gas sample. Exposing a gas sensor to a gas sample comprises bringing the gas sample in proximity to the gas sensor to allow for gas molecules to adsorb to and desorb from the sensor, such as for example by introducing a gas sample to a chamber in a manner that allows for diffusion of gas molecules to a sensor surface and for interaction of gas molecules with a diffusion matrix and with the sensor surface. The term "exposing" encompasses "contacting". Exposing a sensor to a gas sample encompasses contacting the sample with the sensor and contacting the sensor with the sample.

Figure 1B:
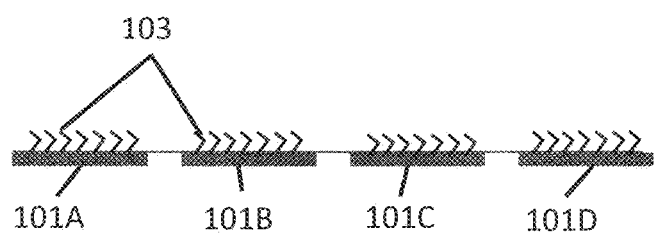
Figure 1C:
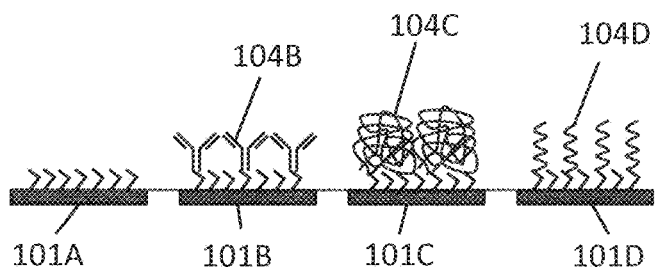

FIG. 1A-FIG. 1D is a schematic depiction of an exemplary embodiment of the invention for detecting a gas species analyte using different diffusion matrices coupled to gas sensors present as an array of sensors. In this exemplary embodiment, gas sensors 101A, 101B, 101C, 101D, present on gas sensor array 102 (FIG. 1A) are derivatized with linker structures 103 (FIG. 1B). In this exemplary embodiment, diffusion matrices 104B, 104C, 104D comprise biomolecules (biomolecular diffusion matrices). Linker structures 103 facilitate attachment of the biomolecular diffusion matrices, 104B, 104C, 104D to sensors 101B, 101C, 101D respectively (FIG. 1C). In some aspects of the invention, coupling of biomolecular diffusion matrices to linkers is mediated by chemisorption, and in additional aspects of the invention coupling is mediated by physisorption. In some aspects of the invention, linker structures 103 may be used to facilitate the synthesis of biomolecular diffusion matrices directly on the nanosensor surface. Heterobifunctional linker structures useful for covalent attachment of chemical and biological structures to surfaces are known and commercially available (e.g., from Sigma-Aldrich Co. LLC, St. Louis, Mo., USA). Exemplary linker structures 103 include silanes, glutaraldehydes, succinimides, carboxylates, epoxies and phosphonates to name only a few. In other aspects of the invention, no biomolecular diffusion matrix is present on a sensor surface, as illustrated by gas sensor 101A having only linker structures 103. In these aspects of the invention, linker structures 103, lacking biomolecules, may also function as a diffusion matrix.

In some embodiments of the invention, biomolecular diffusion matrix 104 is synthesized in situ on the nanosensor.

In some aspects of the invention, biomolecular diffusion matrices may be peptides 104C or nucleic acids 104D that are synthesized in situ on the nanosensor. In certain aspects of the invention, peptides synthesized on a nanosensor may comprise, at least 2, 3, 4, 5, 6, 7, 8, 9, 10, 15, 20, 25, 30, 35, 40, 45, 50, 60, 70, 80, 90, or 100 amino acids or any number therebetween and inclusive of the smaller and larger sizes listed. In other aspects of the invention, peptide length is not limited and may be any length that retains functionality as a biomolecular diffusion matrix and that can be synthesized on, or attached to, a nanosensor. Similarly, in certain aspects of the invention, nucleic acids synthesized on a nanosensor may comprise, at least 2, 3, 4, 5, 6, 7, 8, 9, 10, 15, 20, 25, 30, 35, 40, 45, 50, 60, 70, 80, 90, or 100 nucleotides or any number therebetween and inclusive of the smaller and larger sizes listed. In other aspects of the invention, nucleic acid length is not limited and may be any length that retains functionality as a biomolecular diffusion matrix and that can be synthesized on, or attached to, the surface of a nanosensor. Representative methods for synthesizing peptides and nucleic acids on surfaces can be found in Gao et al., (Proteomics, (2003) 3:2135-2141), and Gao et al., (U.S. Pat. No. 6,426,184), both of which are incorporated by reference herein in their entirety. Other synthesis methods are known to those with skill in the art.

In other embodiments of the invention, biomolecular diffusion matrices comprise biomolecules that are spotted or printed onto a gas sensor. For example, peptides, proteins, nucleic acids, or other biomolecules may be spotted or printed. Such diffusion matrix biomolecules are typically not limited by size, length, shape, or sequence as long as they can be spotted onto the sensor and have some level of chemical or electrostatic interaction with a gas analyte.

Figure 1D:
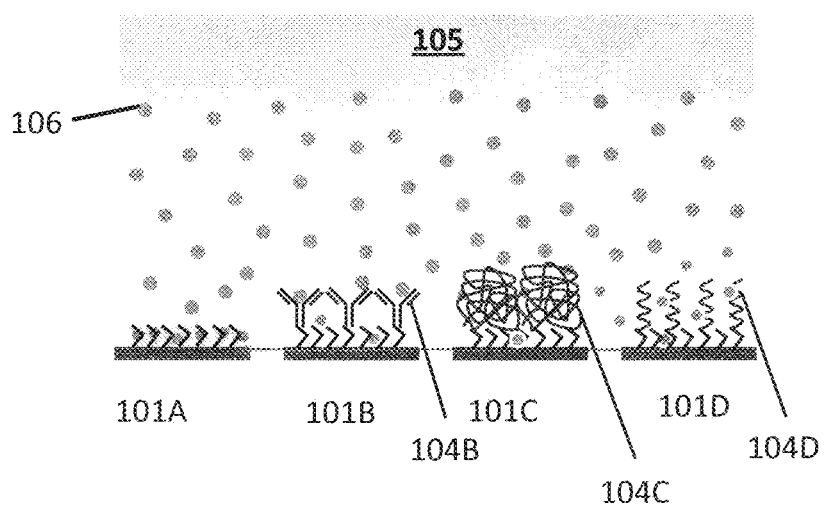

Diffusion of gas analyte 106 from gas source 105 to gas sensor 101 is depicted in FIG. 1D. Gas flow from gas source 105 is used to expose a sensor in a sample chamber to a gas sample having gas species analyte 106. Gas analyte molecules diffuse directly (in the case of linker-derivatized sensor 101A lacking a biomolecular diffusion matrix) or through biomolecular diffusion matrices 104B, 104C, 104D to the sensors where the adsorption of gas molecules on a sensor elicits a response by the sensor due to a change in electrical conductance of the gas sensor (i.e., a "gas sensor response").

Figure 2A:
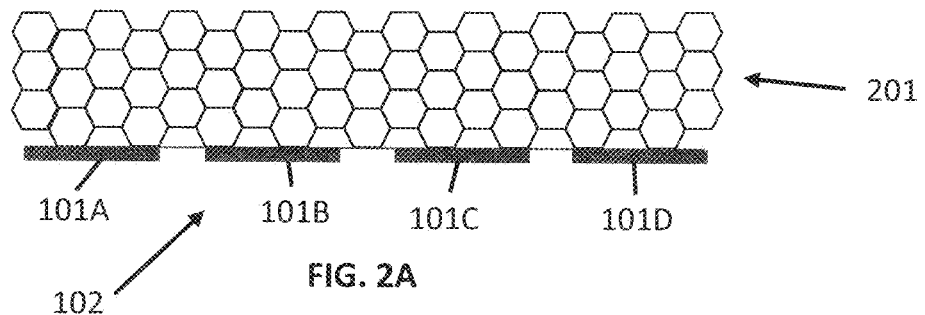
FIG. 2A-FIG. 2C is a schematic depiction of an exemplary embodiment of the invention for detection of a gas species analyte that employs different diffusion matrices (biomolecular diffusion matrices) coupled to a porous support matrix present on gas sensors in a sensor array.
Figure 2B:
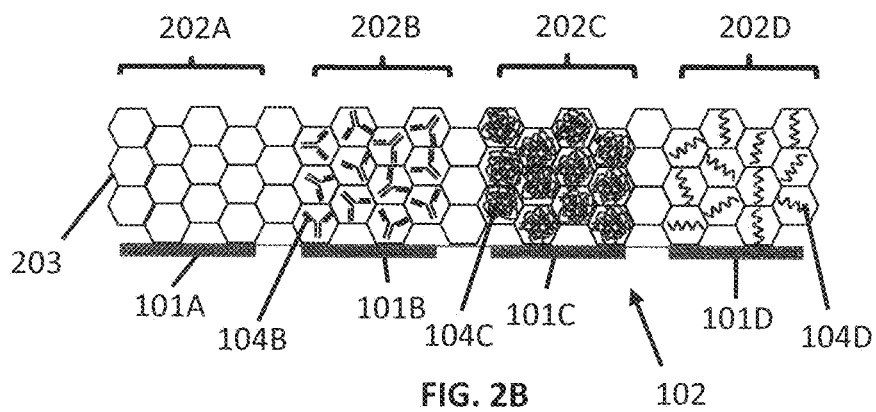
Figure 2C:
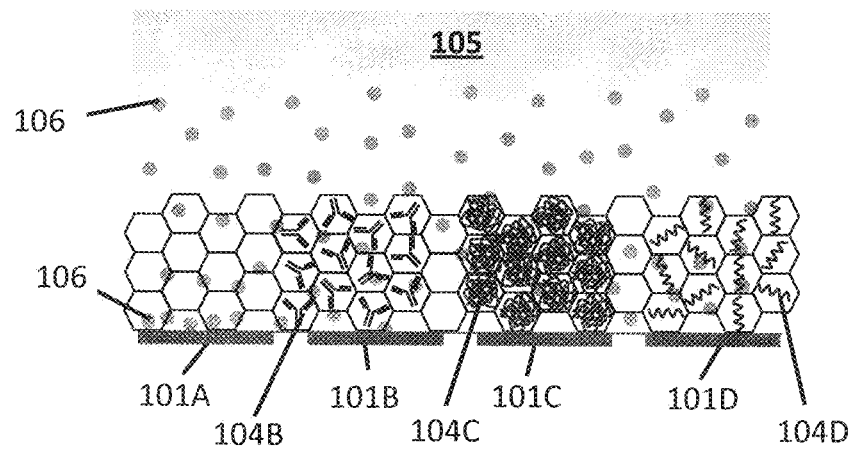

FIG. 2A-FIG. 2C is a schematic depiction of an exemplary embodiment of the invention for detection of a gas species analyte that employs different diffusion matrices (biomolecular diffusion matrices) coupled to a porous support matrix present on gas sensors in a sensor array. FIG. 2A shows an exemplary embodiment of the invention in which a porous support matrix 201, also referred to herein as "porous matrix", is first deposited on sensor array 102. Biomolecules are dispensed onto and/or dispersed into select regions 202B, 202C, 202D of deposited porous support matrix 201 and subsequently coupled to the porous matrix to form biomolecular diffusion matrices 104B, 104C, 104D (FIG. 2B). In some embodiments of the invention, biomolecules are dispensed to deposited porous support matrix 201 that is present on selected sensors so that selected types of biomolecular diffusion matrices are in registration with selected sensors of sensor array 102. Numerous methods may be used for dispensing, dispersing, and coupling biomolecules to, or for directly synthesizing biomolecules on, deposited porous support matrix 201. Some exemplary methods include spotting, inkjet printing, drop-casting, silkscreen printing, gravure printing, and flexographic printing. In some aspects of the invention, biomolecules are dispensed to deposited porous support matrix 201 using a bio-ink. In additional aspects of the invention, a porous matrix is coupled to a sensor by absorption, for example by chemisorption or physisorption. In some embodiments of the invention, covalent coupling of biomolecules to porous support matrix 201 may be employed to couple the biomolecules to structural segments 203 of porous support matrix 201. By way of example only, covalent coupling to structural segments 203 may be mediated by one or more of numerous anchoring chemistries well known in the art, such as silane heterobifunctional crosslinkers, succinimides, glutaraldehyde, and epoxies. Other types of structures for coupling biomolecules to structural segments 203 of deposited porous matrix 201 include silanes, peptides, nucleotides, carbohydrates, and phosphonates to name only a few. Covalent coupling yields a biomolecular diffusion matrix 104 comprising biomolecules permanently attached to deposited porous support matrix 201. In some aspects of the invention, coupling of biomolecules to a porous support matrix may be mediated by chemisorption, such as for example by covalent coupling, and in other aspects of the invention coupling is mediated by physisorption.

In certain aspects of the invention, materials used for porous support matrix 201 have a high surface area for coupling biomolecules. In some embodiments of the invention, deposited porous matrix 201 can be made thicker so as to increase the thickness of biomolecular diffusion matrix 104, thereby enhancing chemical and/or electrostatic interaction of gas analyte 106 with the biomolecular diffusion matrix during diffusion to gas sensor 101.

In some embodiments of the invention, no biomolecules are dispensed to deposited porous support matrix 201 over select sensor surfaces, as in region 202A of porous support matrix 201. In the exemplary aspect shown in FIG. 2A-C, sensor 101A is derivatized with porous support matrix 201 in region 202A, and porous support matrix region 202A, lacking biomolecules, may also function as a diffusion matrix. Porous support matrix 201 may be non-biological material, or mixtures of non-biological materials that contain an interconnected network of volumetric space. In some aspects of the invention, the porosity and thickness of deposited porous support matrix 201 alter the traversal of the biomolecular diffusion matrix by gas analyte 106 in a gas sample from source 105 prior to the interaction of a gas analyte with sensor 101A, 101B, 101C, and 101D (FIG. 2C) thereby affecting the gas sensor response profile.

In some aspects of the invention, structural segments 203 of deposited porous matrix 201 comprise glass, polymer, or composite fibers and may form a mat or sheet. Fibers may be woven or may form a random matrix. In additional aspects of the invention, deposited porous support matrix 201, may comprise beads.

FIG. 3A-FIG. 3C is a schematic depiction of an exemplary embodiment of the invention for detection of gas analytes in which different biomolecular diffusion matrices are coupled to a freestanding porous support matrix that is then registered to specific sensors in a sensor array. In this exemplary embodiment of the invention, biomolecules are dispensed to freestanding porous support matrix 301 that is not initially deposited on sensor array 102 (FIG. 3A). Dispensation of biomolecules to selected regions 302B, 302C, 302D of freestanding porous matrix 301 results in the formation of biomolecular diffusion matrices 104B-104D (FIG. 3A). Methods and materials described above in the discussion of FIG. 2 for dispensing, dispersing, and coupling biomolecules to deposited porous matrix 201 are also useful with freestanding porous support matrix 301. In some aspects of the invention, no biomolecules are dispensed to freestanding porous support matrix 301 over select sensor surfaces, as in region 302A of freestanding porous matrix 301.

Figure 3A:
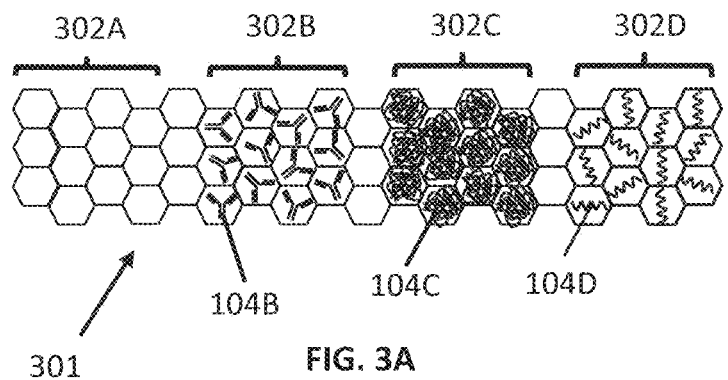
FIG. 3A-FIG. 3C is a schematic depiction of an exemplary embodiment of the invention for detection of gas analytes in which different biomolecular diffusion matrices are coupled to a freestanding porous support matrix that is then registered to specific sensors in a sensor array.
Figure 3B:
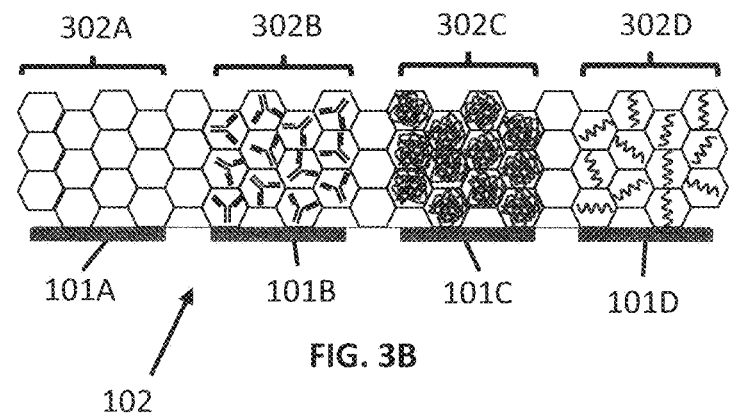
Figure 3C:
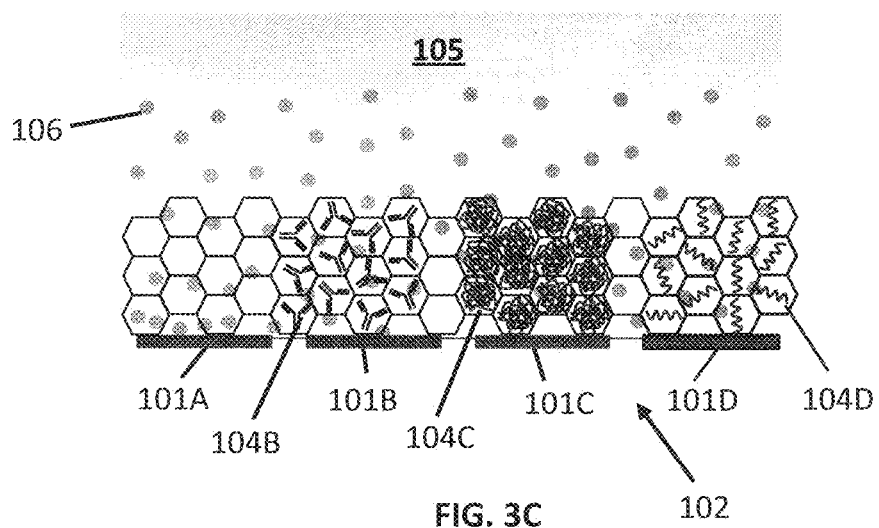

Freestanding porous support matrix 301 comprising biomolecules can be transferred to sensors 101 on sensor array 102 (FIG. 3B). In some embodiments, freestanding porous support matrix 301 is registered to sensor array 102 such that specific sensors 101 are derivatized with selected specific biomolecular diffusion matrices. For example, region 302B of freestanding porous matrix 301 may receive antibody biomolecules forming biomolecular diffusion matrix 104B, which is registered to sensor 101B. Similarly, biomolecular diffusion matrix 104C may comprise peptides or protein molecules with a specific conformation. Further, biomolecular diffusion matrix 104D may comprise nucleic acid biomolecules. Sensor array 102 can then be exposed to a gas sample (FIG. 3C) from gas source 105 which can lead to detection of gas species analyte 106 by sensors 101 in an analogous fashion to that described for FIG. 1 and FIG. 2. Similarly, in this exemplary aspect of the invention, sensor 101A is derivatized with porous support matrix 301 in region 302A, and porous support matrix region 302A, lacking biomolecules, may also function as a diffusion matrix.

In additional exemplary embodiments of the invention, biomolecular diffusion matrices comprising peptides 104C or nucleic acids 104D may be synthesized in situ on deposited porous support matrix 201 or on freestanding porous support matrix 301. In certain aspects of the invention, synthesized peptides may comprise, at least 2, 3, 4, 5, 6, 7, 8, 9, 10, 15, 20, 25, 30, 35, 40, 45, 50, 60, 70, 80, 90, or 100 amino acids or any number therebetween and inclusive of the smaller and larger sizes listed. In other aspects of the invention, peptide length is not limited and may be any length that can be synthesized on a porous support matrix 201 or 301 and that retains functionality as a biomolecular diffusion matrix. Similarly, in certain aspects of the invention, synthesized nucleic acids may comprise, at least 2, 3, 4, 5, 6, 7, 8, 9, 10, 15, 20, 25, 30, 35, 40, 45, 50, 60, 70, 80, 90, or 100 nucleotides or any number therebetween and inclusive of the smaller and larger sizes listed. In other aspects of the invention, nucleic acid length is not limited and may be any length that can be synthesized on a porous matrix 201 or 301, and that retains functionality as a biomolecular diffusion matrix. Representative methods for synthesizing peptides and nucleic acids on matrix surfaces can be found in Gao et al., (Proteomics, (2003) 3:2135-2141), and Gao et al., (U.S. Pat. No. 6,426,184).

In embodiments of the invention, a gas sensor response profile is determined for a selected time period, ranging from a selected time before exposure of a sensor to a gas sample to a selected time after stopping gas sample flow. Gas sensor response profiles are determined by measuring a sensor parameter, such as for example resistance, current, capacitance, or electrochemical potential from the selected time before exposure of a sensor to a gas sample to the selected time after stopping gas sample flow. In embodiments of the invention, response of a gas sensor to a gas analyte molecule requires interaction of the gas analyte molecule with the sensor. In certain aspects of the invention, multiple gas sensor response profiles may be determined in succession, such as for example when recording sensor responses to multiple gas sample exposures. In embodiments of the invention, sensor response profile data may be represented as a plot of sensor response data, e.g., current or resistance vs. time. As used herein, "gas sensor response profile" means the gas sensor response data and associated data determined as described above. "Gas sensor response profile" may also mean a graphical representation or other representation of the determined gas sensor response data and associated data.

In embodiments of the invention, a gas sensor response profile determined with a known gas species analyte (control gas species) in a control sample is compared with a sensor profile determined for an unknown gas species analyte in a test sample for identifying and quantifying a gas species analyte present in a test sample. In additional embodiments of the invention, multiple gas sensor response profiles determined under a variety of conditions with control and test samples are compared. Multiple unknown gas species analytes in a test sample may be detected, identified, or quantified. A gas sensor response profile determined with one or more control gas species may be referred to interchangeably as a "control gas sensor response profile", a "control sensor response profile", or a "control sample sensor response profile". Similarly, a gas sensor response profile determined with a test gas sample may be referred to interchangeably as a "test sample gas sensor response profile", a "test sample response profile", or a "test sample sensor response profile".

Figure 4A:
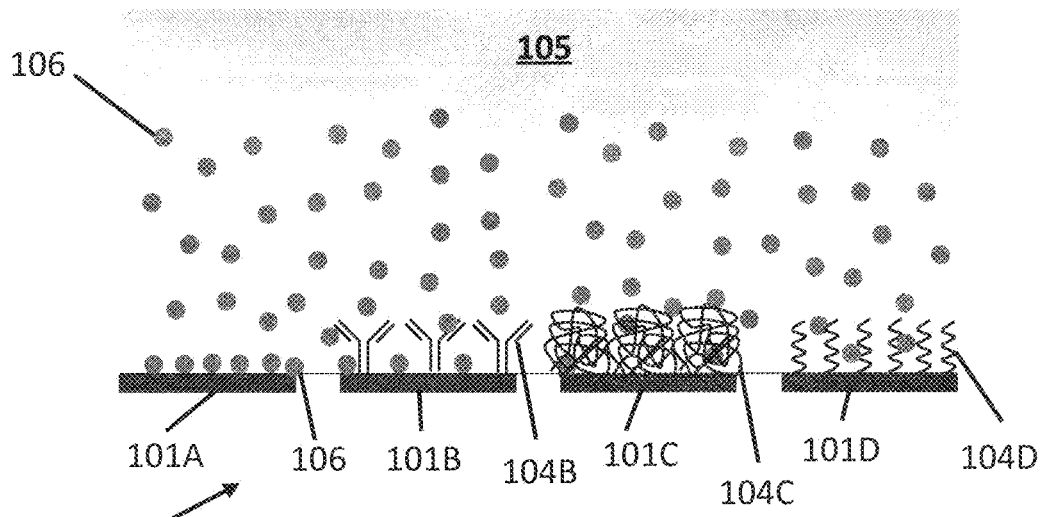
FIG. 4A-FIG. 4D schematically illustrate the diffusion of gas species analytes 106 (FIG. 4A) and 402 (FIG. 4C) through different types of biomolecular diffusion matrices attached to sensors and the resulting plotted gas sensor response profiles (FIG. 4B, FIG. 4D) that are unique for each type of diffusion matrix and for each gas.
Figure 4B:
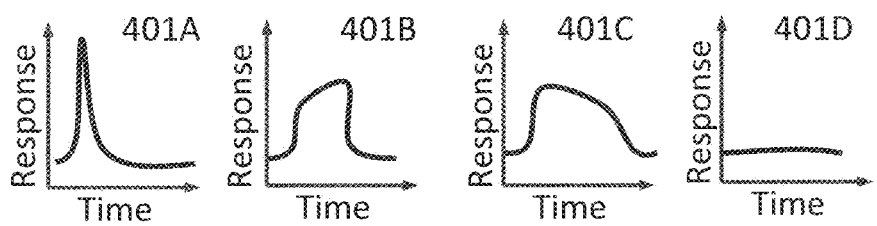

FIG. 4A-FIG. 4D schematically illustrate the diffusion of gas species analytes 106 (FIG. 4A) and 402 (FIG. 4C) through different types of biomolecular diffusion matrices attached to sensors and the resulting plotted gas sensor response profiles (FIG. 4B, FIG. 4D) that are unique for each type of diffusion matrix and for each gas. FIG. 4A-FIG. 4D demonstrate schematically that gas sensor response profiles differ depending on the gas species interacting with a sensor and the type of diffusion matrix present on a sensor. FIG. 4A shows a representation of gas sensor array 102 having a sensor 101A that is underivatized (a bare sensor with no linkers or other molecules) and sensors 101B-101D that are derivatized with different types of biomolecular diffusion matrices 104B-104D, respectively. Sensors are exposed to gas analyte 106 from gas source 105. Each gas sensor 101A, 101B, 101C, and 101D produces a sensor response profile (401A, 401B, 401C, 401D) that is the electrical response of the sensor vs. time from a selected time before exposure of sensors to a gas sample to a selected time after stopping gas flow from gas source 105 (FIG. 4B). The response profiles 401B-401D determined for gas analyte 106 interacting with sensors 101B-101D having different types of biomolecular diffusion matrices 104 are different from one another and different from response profile 401A determined for gas analyte 106 interacting with underivatized bare sensor 101A.

Figure 4C:
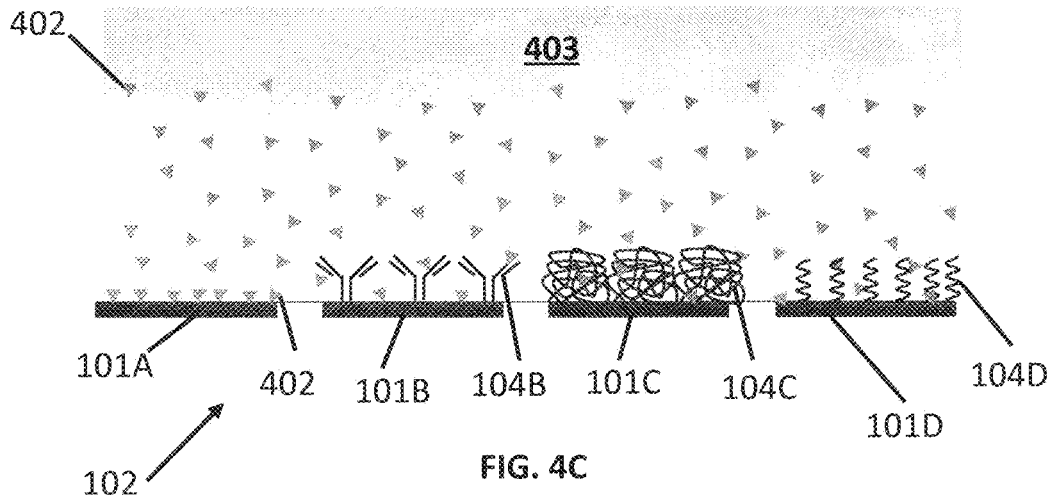
Figure 4D:
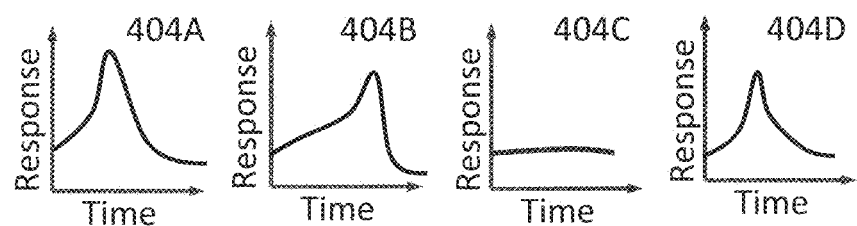

FIG. 4C shows a representation of gas sensor array 102, having the same respective sensors 101A, 101B, 101C, and 101D as shown in FIG. 4A. Sensors are exposed to a different gas species 402 from gas source 403. FIG. 4D shows that the sensor response profiles (404B, 404C, 404D) determined for gas analyte 402 interacting with sensors 101B-101D having different types of biomolecular diffusion matrices 104 are also different from one another and from response profile 404A determined for gas analyte 106 interacting with underivatized bare sensor 101A. Furthermore, the sensor response profiles 401B-401D and 404B-404D determined with the same biomolecular diffusion matrices 104B-104D but different gas analytes (106, 402) are also different from one another. The response of underivatized bare sensor 101A, lacking any diffusion matrix, also differs depending on the gas species being analyzed (401A vs. 404A). In embodiments of the invention, such differences enable the identification and quantification of unknown gas species analytes in a test gas sample.

Gas sensor response profiles exhibit a baseline response prior to exposure of a sensor to a gas, followed by a response of the sensor during gas exposure. After stopping gas analyte flow from a gas source, gas analyte molecules may desorb and diffuse from the surface of a sensor 101, causing the gas sensor response profile to return to baseline. Desorption and diffusion from the sensor surface may occur unaided as a result of a concentration gradient or may be enhanced by introduction of a purge gas such as clean, dry air, or conversely by evacuation. Purging may be unassisted or may be accelerated by heating a sensor or a sensor array 102.

The inventors found that sensor response profiles differ depending on sensor characteristics, gas properties, or other experimental conditions, including by way of example only, the derivatization state of the sensor, the gas species analyte of interest, and the type of diffusion matrix through which the analyte diffuses on its path to a sensor. Diffusion differences can be utilized to increase the accuracy of gas analyte detection and identification and to aid in the quantification of one or more gas species analytes in a test sample containing individual gas species or gas mixtures. In some embodiments of the invention, gas sensor response profiles 401 are determined using control (known) gas species. In additional embodiments of the invention, gas sensor response profiles 401 are determined using known concentrations of control gas species. In still further embodiments of the invention, gas sensor response profiles 401 are determined with underivatized sensors or with sensors derivatized with selected types and configurations of diffusion matrices. One or more gas sensor profiles determined under different experimental conditions, with control gas species, may be stored in a database. Comparisons of these stored gas sensor response profiles with gas sensor response profiles determined for a test sample can be used to detect, identify, and/or quantify one or more gas species analyte in a test sample. In some aspects of the invention, a test sample or control sample or a portion of a test or control sample may be diluted prior to determining a gas sensor response profile.

Figure 5:
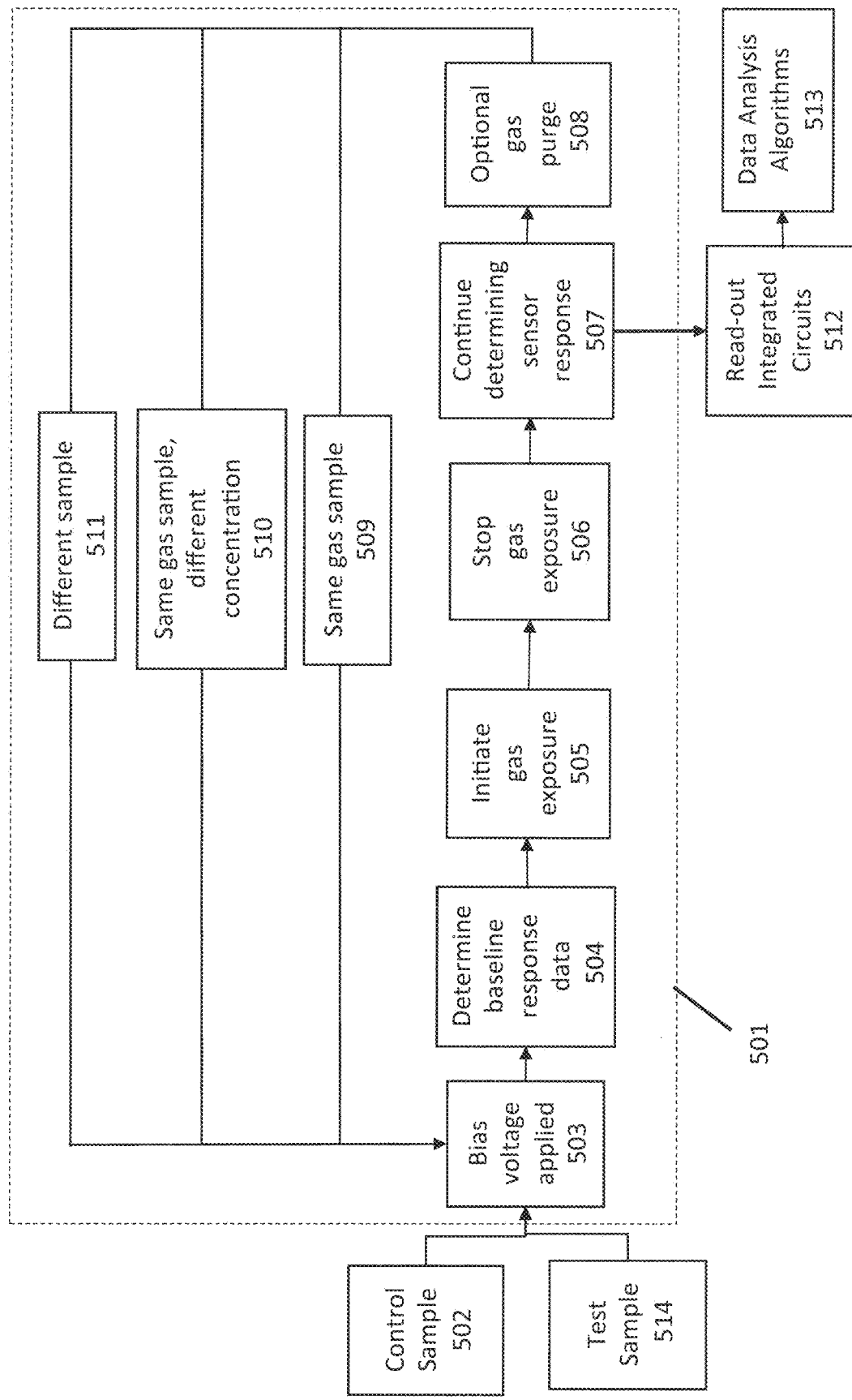
FIG. 5 is a flow chart of an exemplary workflow useful in some invention embodiments for detecting, identifying, and/or quantifying a gas analyte in a test sample.

FIG. 5 is a flow chart of an exemplary workflow useful in some embodiments of the invention for detecting, identifying, and/or quantifying a gas analyte in a test sample. In some embodiments of the invention, evaluating a test sample for the presence of a gas analyte comprises following a series of test and analysis protocols, testing regimen 501, as illustrated in FIG. 5. In these embodiments, gas detection and analysis begins by determining a gas sensor response profile for a control sample 502 comprising one or more known gas species at a known concentration. Determining a gas sensor response profile comprises steps 503 through 507 in FIG. 5 and begins by applying a bias voltage 503 across all sensors 101 in array 102. The bias voltage is applied for a sufficient duration to allow the sensors to stabilize to the environmental conditions (i.e., the sensors exhibit a relatively unchanging current value). After stabilization, determination of baseline response data 504 is initiated. After a selected period of time (typically a few seconds) of determining baseline data, gas exposure 505 is initiated and continues for a selected period of time prior to stopping the gas exposure 506. Exposure times may range from a few milliseconds to hundreds or even thousands of seconds. It is specifically contemplated that gas sample exposure times may be for any selected length of time in that range. Sensor response profile data are determined from the selected baseline time point, throughout gas exposure, and after the gas exposure period 507 to the selected end time point. Data determination periods can range from seconds to hours. In some embodiments of the invention, it is specifically contemplated that there is no limit on the time period for data determination. An optional gas sample purge step 508, such as for example pulsing clean dry air over the sensors with or without heating, may be employed to clear gas from the sensors. In some aspects of the invention, determining baseline and sensor response data (i.e., determining a gas sensor response profile) comprises recording the data. In other aspects of the invention, sensor response data are plotted graphically. In still further aspects of the invention, sensor response data are analyzed by read out integrated circuits (ROIC) 512 and may be further analyzed with data analysis algorithms 513.

In certain embodiments of the invention, one or more determinations of gas sensor response profiles to the same gas sample 509 may be employed using testing regimen 501. In additional embodiments, one or more determinations of gas sensor response profile to the same gas species at different concentrations in a gas sample or a portion of a gas sample 510 may be employed. Similarly, one or more determinations of gas sensor response profiles to a different control gas sample 511 may be employed using testing regimen 501. There is no limit on the number of replicate and/or different gas samples that may be employed in testing regimen 501.

Similarly, in various embodiments of the invention, the duration of gas exposure may be varied. By way of example only, gas exposure duration times may be about 0.001 sec, 0.01 sec, 0.1 sec, 0.2 sec, 0.5 sec, 1 sec, 2 sec, 5 sec, 10 sec, 20 sec, 30 sec, 60 sec, 120 sec, 300 sec, 400 sec, 500 sec, 1,000 sec or any specific selected duration between about 0.001 sec and about 1,000 sec or more inclusive. Any gas exposure duration time may be used in combination with any number of replicates performed with the same or different gases.

In some embodiments of the invention, gas sensor response profiles can be determined at the same time for all gas sensors 101 that are present in array 102, using ROICs 512, such as for example, ROICs comprising silicon CMOS logic. Determination of sensor response profiles provides data for use with analysis algorithms 513 for comparing test sample sensor response profiles and control sample sensor response profiles, enabling gas species identification and quantification.

After data collection for sensor response profiles determined with one or more control gas sample 502, response profiles of sensors 101 on array 102 are determined for a test gas sample 514, which may include single or multiple unknown gas species analytes present in a variety of concentrations. Test sample sensor response profiles are determined as for control gas sensor response profiles as described above.

In some aspects of the invention, one or more control gas sensor response profiles and test sample sensor response profiles may be stored in a database, and comparing sensor response profiles comprises comparing one or more test sample response profiles to one or more control gas response profiles stored in the database. Comparisons of these stored gas sensor response profiles can be used to determine the identity and concentration of one or more gas analyte in a test sample. In additional aspects of the invention, deconvolution of gas sensor response data enables the identification and quantification of gases in a test sample.

Qualitative and quantitative differences and similarities among control gas sensor response profiles and test sample sensor response profiles can be determined by using ROIC 512 and data analysis algorithms 513 and comparing data from control sample 502 sensor response profiles with data from test sample 514 sensor response profiles. Numerous computational algorithms are available in the art that are useful for identifying differences in datasets. Such algorithms are applicable for determination of qualitative and quantitative differences between sensor response profiles. In addition, deconvolution algorithms can be used to identify and quantify individual gases using sensor response profile data acquired from control gas species and from a test gas sample. Methods for deconvolution are known in the art. Deconvolution comprises cross comparison of response profile data from all sensors 101 in sensor array 102 for each different control gas sample 502 and test gas sample 514 evaluated using testing regimen 501.

In embodiments of the invention, comparison of one or more control gas 502 sensor response profiles with one or more test sample 514 sensor response profiles is used to detect, identify, and/or quantify a gas species analyte present in a test sample. In some aspects of the invention, test sample and control gas sensor response profiles for comparison are determined under a variety of different conditions, such as for example, with different types of diffusion matrices, with different concentrations of gases in a gas phase or in a vapor phase of a liquid or solid, and/or with multiple different gas species. Comparisons of control and test sample gas sensor response profiles determined under a variety of conditions enable, contribute to, and enhance detection, identification, and/or quantification of a gas analyte in a test sample.

In other embodiments, control gas sensor response profiles are determined using various types and configurations of diffusion matrices on gas sensors or are determined using underivatized gas sensors.

In further embodiments of the invention, detecting, identifying, and/or quantifying a gas analyte in a test sample comprises comparing a test sample sensor response profile, determined using a specific type of diffusion matrix, with one or more control gas sensor response profiles determined using the same type of diffusion matrix. In specific embodiments of the invention, detection, identification, or quantification of a selected gas species in a test sample, comprises comparing a test sample sensor response profile, determined with a specific type of diffusion matrix, with a control gas sensor response profile determined using the same type of diffusion matrix with the selected gas species. In further aspects of the invention, identification of a plurality of selected gas species in a test sample comprises comparing a test sample sensor response profile determined with a specific type of diffusion matrix with a plurality of control gas sensor response profiles determined with the same type of diffusion matrix and with the selected gas species of interest.

In additional embodiments of the invention, a control gas sensor response profile may be determined using the same sensor as that used for a test sample sensor response profile, but prior to determining the sensor response profile with the test gas sample. In certain embodiments of the invention, multiple sensor response profiles are determined with a single test sample or a portion of the same test sample.

In embodiments of the invention, a gas sample, including a control sample and a test sample, may comprise a gas, a liquid, and/or a solid. In some embodiments, a test sample or control sample comprises individual gases or mixtures of gases. In other embodiments, a test sample comprises a liquid or solid having a corresponding vapor component in which a gas analyte is identified and/or quantified. In some aspects of the invention, a liquid sample may be a biological sample or an extract of a biological sample having a corresponding vapor component. In some aspects of the invention, a biological test sample may be from or may comprise blood, serum, plasma, tissue, organs, semen, saliva, breath, tears, sputum, feces, urine, other bodily fluid, hair follicles, skin, or any sample containing or constituting biological cells. Alternatively, the sample may not be a biological sample, but may be a chemical mixture. In other aspects of the invention, the sample may be an environmental sample, such as an air sample or other gaseous sample or a liquid sample. A sample may be, or may comprise, an extract of an environmental sample, such as for example a soil extract or an extract of a water sample. A water sample may comprise a gas species analyte that is a biological toxin or toxicant. In some aspects of the invention, a test sample comprises a synthetically prepared biological or chemical entity. A synthetically prepared biological or chemical entity may be a precursor or product of a biological, chemical or industrial manufacturing process.

In some aspects of the invention, a test sample is prepared using methods that isolate or purify a gas species analyte of interest, including gas species analytes present in a liquid or solid sample having a corresponding vapor component, in a form that will traverse a diffusion matrix on a sensor 101. Methods for extracting, isolating, or purifying biological molecules and chemicals from numerous types of samples, including biological, environmental and industrial or pharmaceutical manufacturing samples, are available in the art. In other aspects of the invention, a sample is not purified or extracted prior to contacting the sample with a gas sensor.

In some embodiments of the invention a biological test sample is from an organism. In certain aspects of the invention, the biological sample is from a patient. In other aspects, the biological sample is from a medical, pharmaceutical or biological manufacturing process. In one exemplary aspect of the invention, the sample can be a biological threat sample collected by military or first responders. In some embodiments, a sample is from a patient that has tested positive for a disease, a patient undergoing treatment, a patient with a tumor or known mutation that results in the production of a specific disease-associated analyte, or a patient suspected of having a disease or condition. A biological sample may also include one or more gas species analytes indicative of the presence of a pathogen, a virus, a prion, a fungus, a bacterium, or another organism. In other embodiments of the invention, a sample may be exhaled breath, such as for example from an individual (e.g., a patient or a soldier). In further embodiments, the sample may be collected by sampling ambient air around an object or a subject in order to determine or identify recent human activity. Further still, the sample may be collected by sampling ambient air for the presence of a human or other organism or for other potential identifying characteristic associated with a specific biological odor profile.

The presence of selected gas species analytes in a sample and/or the amounts of selected analytes in a sample may be indicative of a disease or condition, may correlate with the severity of a disease or condition, may be used to evaluate the response of a patient to a treatment, or may be used to optimize treatment of a patient. The presence or amount of analyte in a biological sample may also be examined to evaluate and correlate the analyte with pharmacokinetics and to adjust the treatment of a patient such as with a compound or a drug. In some aspects of the invention, a gas species analyte may be a metabolic by-product or breakdown product of a treatment compound or a drug.

Multiple analytes present in a single sample may be queried using methods of the invention. For example, selected individual gas nanosensors or groups of gas nanosensors may be derivatized with selected diffusion matrices through which selected analytes present in a sample diffuse differently. It is contemplated that many analytes can be queried at a single time, in a multiplexed assay format, by using arrays of multiple nanosensors that are derivatized with selected different types of diffusion matrices.

Figure 6:
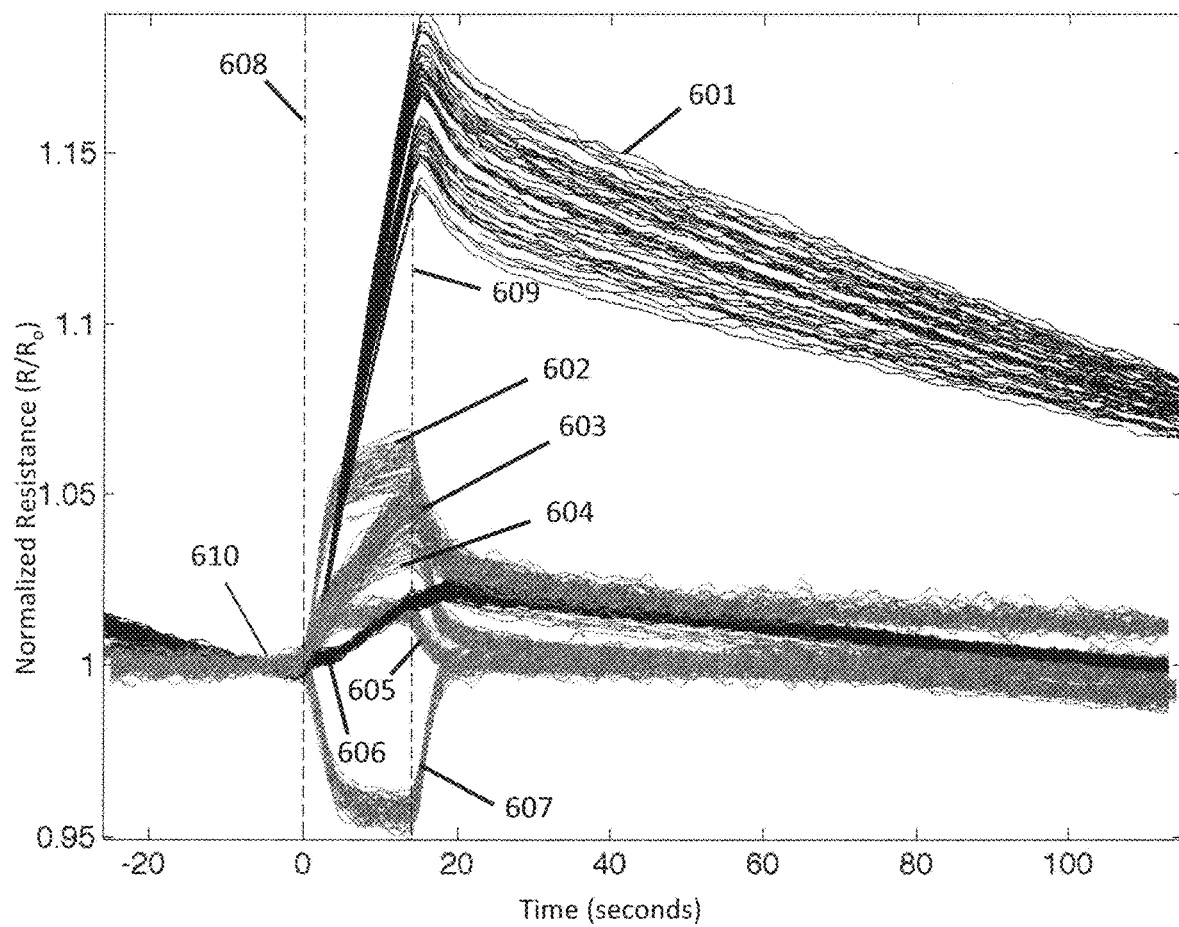
FIG. 6. shows multiple gas sensor response profiles determined for each of six different volatile organic compound gas analytes and for water, using a sensor derivatized with linker structures.

FIG. 6. shows multiple gas sensor response profiles determined for each of six different volatile organic compound gas analytes and for water, using a sensor derivatized with linker structures. For this experiment, the inventors used arrays of conductometric semiconducting tin oxide ($SnO_x$) nanotrace sensors, each nanotrace being 80 nm in width, prepared using nanoimprint lithography according to methods described in Savoy et al., U.S. Pat. No. 8,450,131. Gas sensor response profiles were determined for each of six different volatile organic compound (VOC) gases and for water 602. The VOC gases included 4-methylbenzaldehyde 601, 4-methyl valeric acid 603, benzaldehyde 604, 2,4-dimethylacetophenone 605, 2-ethyl hexanoic acid 606, and 2-ethylhexanol 607. Sensor response profiles for each gas were determined using 64 independently addressable nanotrace sensors (56 sample sensors shown in FIGS. 6 and 8 blank control sensors having no metal oxide that are not shown in the figure).

Gas sensor response profiles were determined according to methods described above (FIG. 5), by measuring the electrical current flowing through the sensor as a function of time, beginning at a selected time point prior to initiation of gas exposure and continuing through the length of the gas exposure and for a selected period of time after exposure of the sensor to the gas was stopped. Bias voltage was applied and the average value of baseline current 610 was measured in the 5 sec period prior to initiation of gas exposure. Linker-derivatized sensors were exposed to a gas analyte sample at time (t)=0 sec (represented as dashed line 608). Gas sample exposure was stopped at t=15 sec (represented as dashed line 609).

Sensor response data (i.e., current measurements) were converted to normalized resistance over time using Ohm's law (V=IR) and the applied bias, typically between 0.01 to 100 V. In this example, each gas sensor response profile, plotted as normalized resistance vs. time, was normalized by dividing the value of all data points on the gas sensor response profile with the average value of the baseline current 610. For the seven sets of 56 gas sensor response profiles for each gas in FIG. 6, current measurements were aligned at t=0 sec.

The inventors found that multiple determinations of gas sensor response profiles, using the same gas analyte exhibited the same pattern (FIG. 6), and gas sensor response profiles differed among different gas analytes. The sensor response profiles for water and each gas species 601-607 have characteristics also exhibited by sensor response profiles determined with sensors derivatized with other diffusion matrices. The response profiles display differences among the different gas species 601-607 in the rate of sensor response rise, the maximum change in sensor response, and the rate of response fall after stopping gas exposure. These characteristics of the sensor response profiles indicate different responses to each gas analyte. The gas sensor response profile represents a composite effect resulting from the sample gas diffusion rate, the rate of adsorption of the gas onto the sensor, the rate of desorption of the gas from the sensor, and the effect on charge carrier mobility and carrier concentration of the sensor when gas molecules are adsorbed on the sensor surface. In some aspects of the invention, exposure of a gas sensor to certain gas species may result in no sensor response changes, such as when a gas sensor is exposed to clean dry air. In these aspects, sensor response is unchanged until the exposure of sensor 101 to a gas sample is stopped 609.

Sensor response profiles may also be sensitive to temperature. In some aspects of the invention, test sample and control response profiles may be determined at a temperature that is approximately room temperature (~25 C) or at a temperature that is above or below room temperature.

Figure 7A:
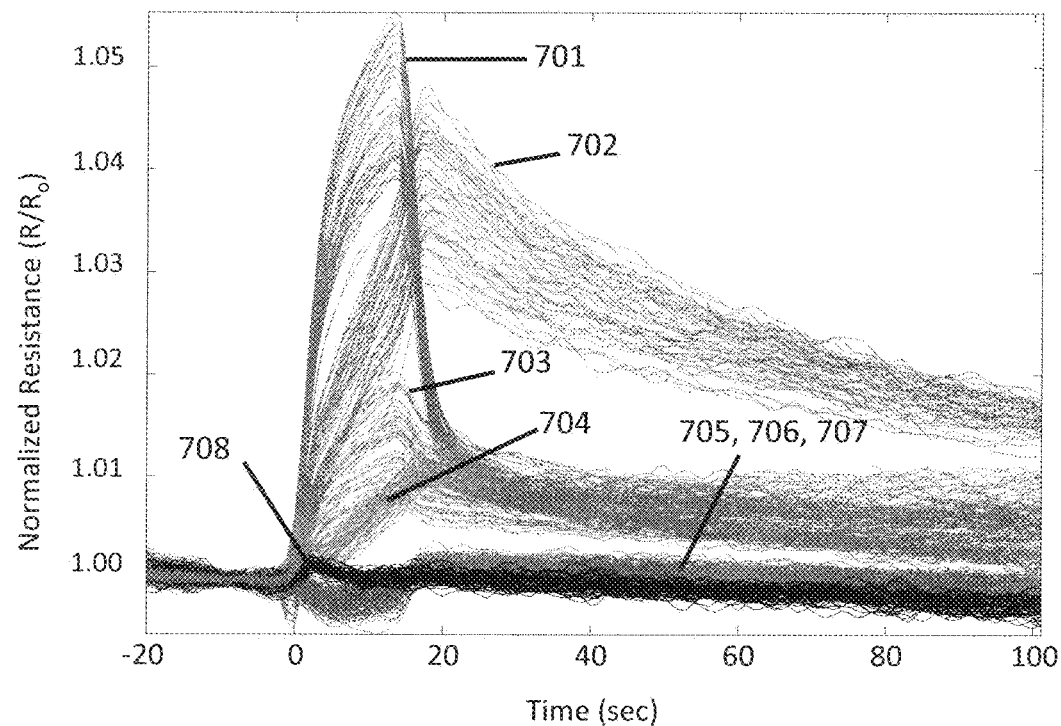
FIG. 7A-FIG. 7D.
Figure 7B:
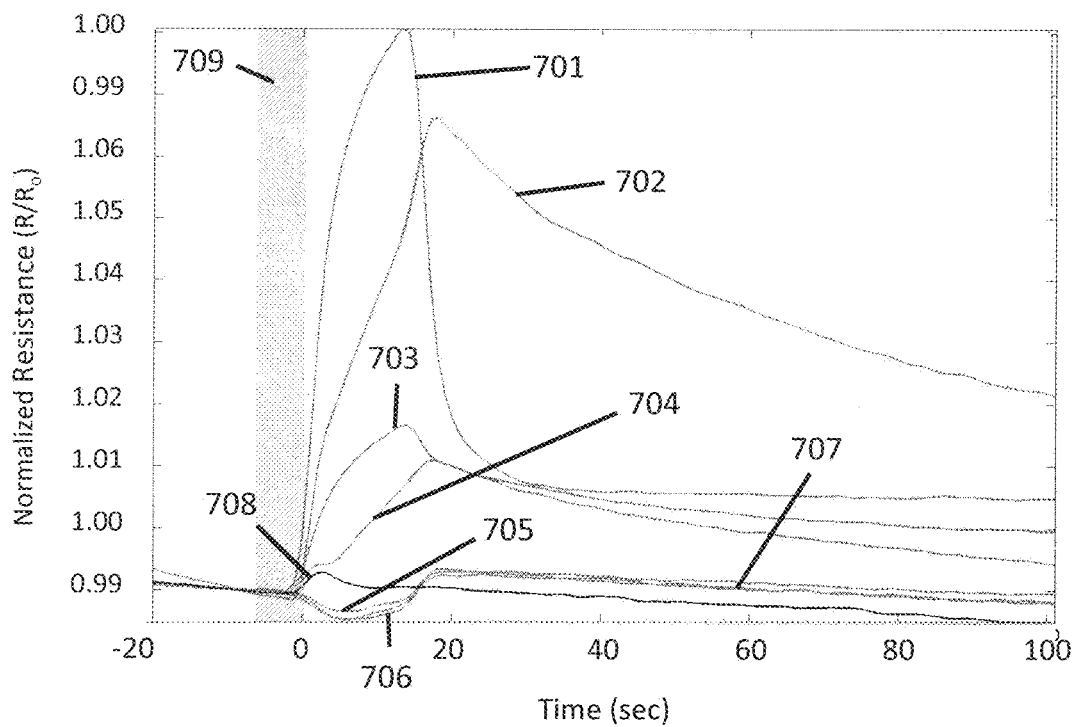
Figure 7C:
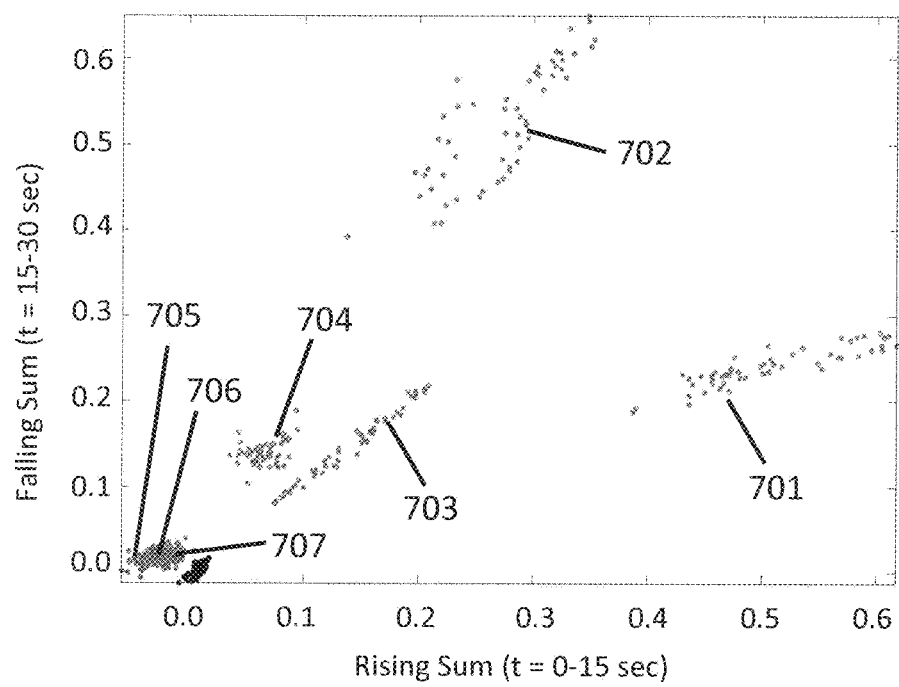
Figure 7D:
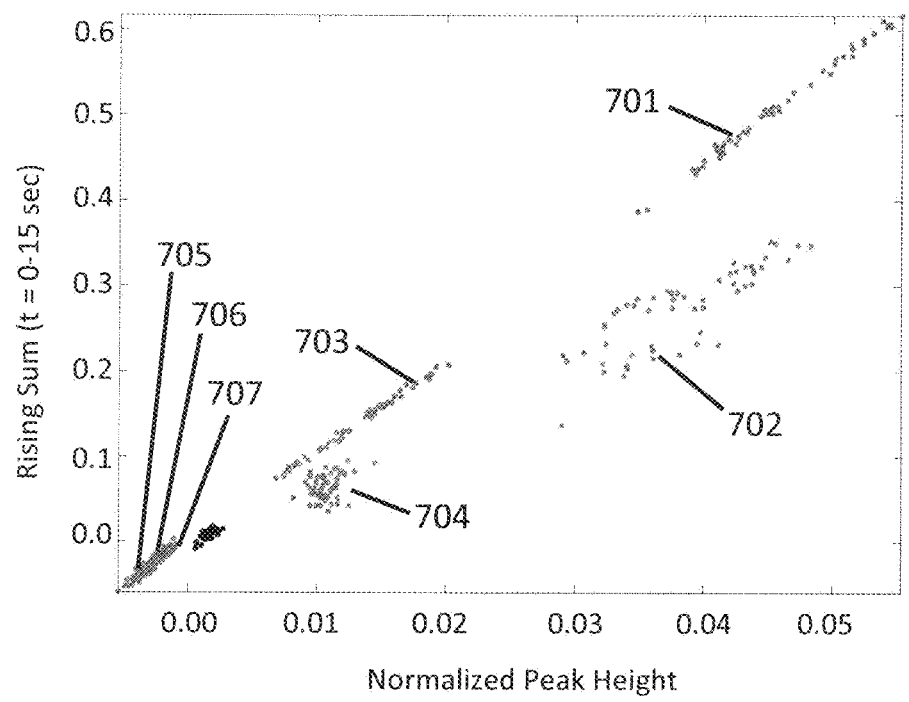

FIG. 7A-FIG. 7D. FIG. 7A shows multiple gas sensor response profiles determined using a sensor derivatized with linker structures, for each of seven different volatile organic gas analytes from common industrial solvents. FIG. 7B shows the averaged gas sensor response profile from all sensors for each gas. FIG. 7C and FIG. 7D show principal component analysis plots using data from the gas sensor response profiles. Gas sensor response profiles with similar characteristics were observed for multiple replicates of volatile organic compound gas samples such as common industrial solvents. Fifty-six (56) gas sensor response profiles determined for each sample gas are shown in FIG. 7A. The gases were methanol 701, diethylether 702, dichloromethane 703, acetone 704, hexanes 705, toluene 706, and xylene 707. Similar to the response profiles shown in FIG. 6, the sensor response profiles for each gas type 701-707 exhibited differences in the rate of sensor response rise, the maximum change in sensor response, and the rate of response fall after stopping gas exposure. These differences are more clearly apparent when the averaged gas sensor response profiles from all sensors for each gas are plotted (FIG. 7B). Switching noise can cause a false response such as that observed for sensor response profile 708, which was determined for clean dry air. Switching noise from the gate valve and other electronic interference artifacts can be removed by shielding. Sensor response profiles 701-708 were normalized to data collected during the time interval just before gas analyte exposure (represented by the shaded area 709 of FIG. 7B).

In this example, gas sensor response profiles were determined for all 56 sensors for each gas (FIG. 7A). Sensor response profiles differed among the gases. However, the response profile for each sensor in the array was found to be highly reproducible among the 56 replicate measurements for a single gas species. Replicate sensors showed high precision (S.D.<2%). Principal component comparison plots of the falling sum vs. the rising sum (FIG. 7C) and the rising sum vs. the normalized peak height (FIG. 7D) show the differences in the response profiles among the individual sensor responses. In addition, the plots illustrate that sample gases with similar chemical functional groups such as nonpolar aliphatic and aromatic hydrocarbons 705, 706, 707 behave similarly and display the least differences in the respective response profiles. In embodiments of the invention, improved separation of these gas species can be achieved by analyzing sensor response profiles determined with sensors that are derivatized with different types of diffusion matrices, resulting in enhanced detection and quantification of specific gas analyte species.

To determine the gas sensor response profiles illustrated in FIG. 6 and FIG. 7, a sample of solvent vapor at the full vapor pressure at room temperature was isolated in an impinger vessel or directly connected from a lecture bottle of the gas. Gas exposure was accomplished by directing a fixed flow rate of a carrier gas (measured as sccm) into the liquid impinger using a mass flow controller. Examples of carrier gases include clean dry air, argon, or other inert gases. This sample stream was recombined with the stream of carrier gas then directed over the gas sensor for fixed time intervals ranging from 1 sec-300 sec. The concentration of the gas analyte sample in the carrier gas is controlled using mass flow controllers. In some embodiments of the invention, test samples may be diluted with or directly combined with a background carrier gas that is directed over the surface of gas sensor 101.

In some experiments, responses were determined for each sensor as the ratio $R_s/R_0$ converted from the measured sample current ($I_s$) using the applied bias voltage V and Ohm's law and a normalization procedure. Current measurements were first determined at a fixed voltage, typically in the range of 0.1V-1V. Useful fixed voltages may be as low as 1 microVolt to as high as hundreds of Volts. In additional embodiments of the invention, normalization involves dividing each calculated resistance value of the response ($R_s$) with the measured resistance just prior to sample exposure ($R_0$).

Figure 8A:
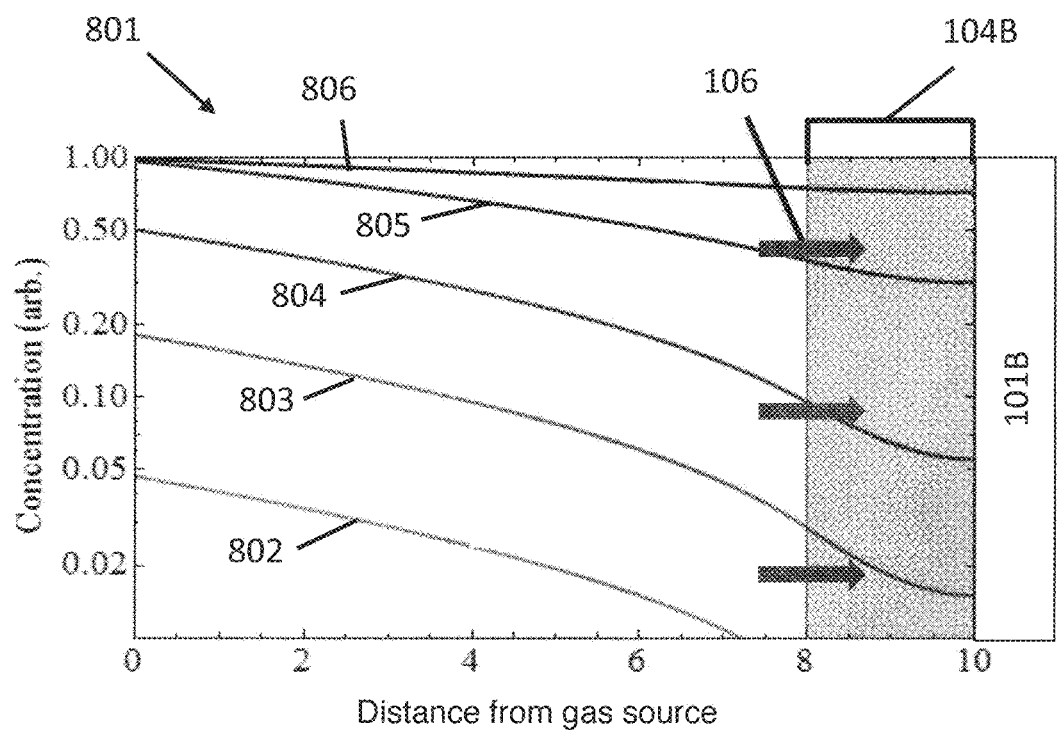
FIG. 8A-FIG. 8C.
Figure 8B:
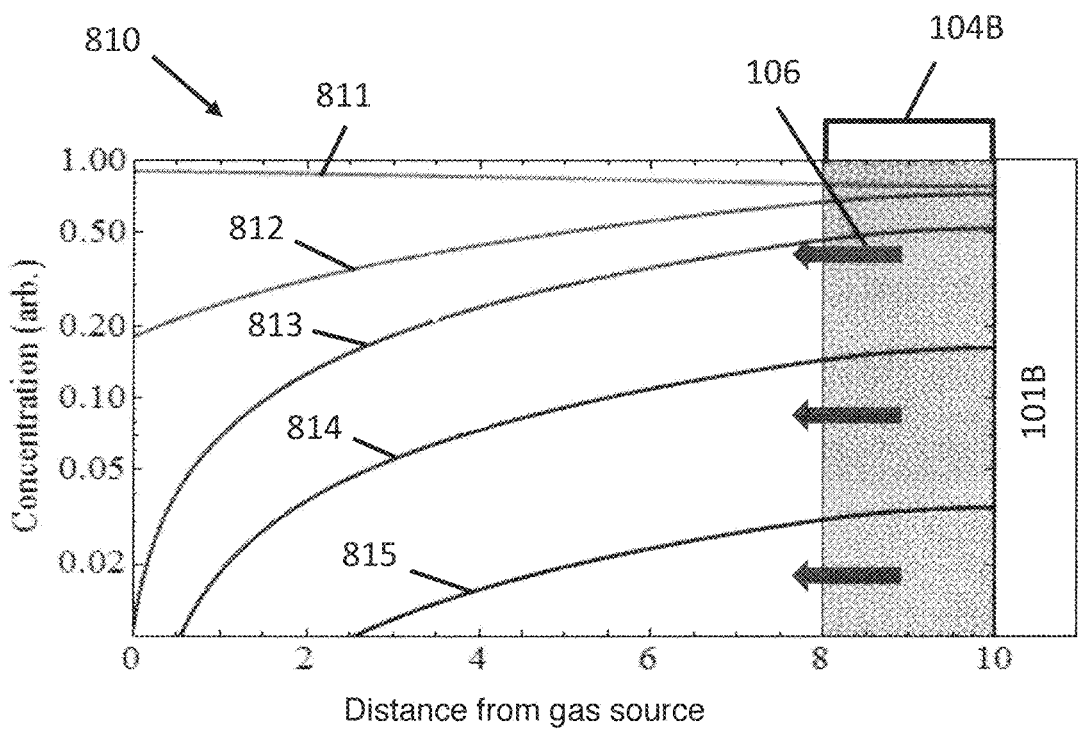
Figure 8C:
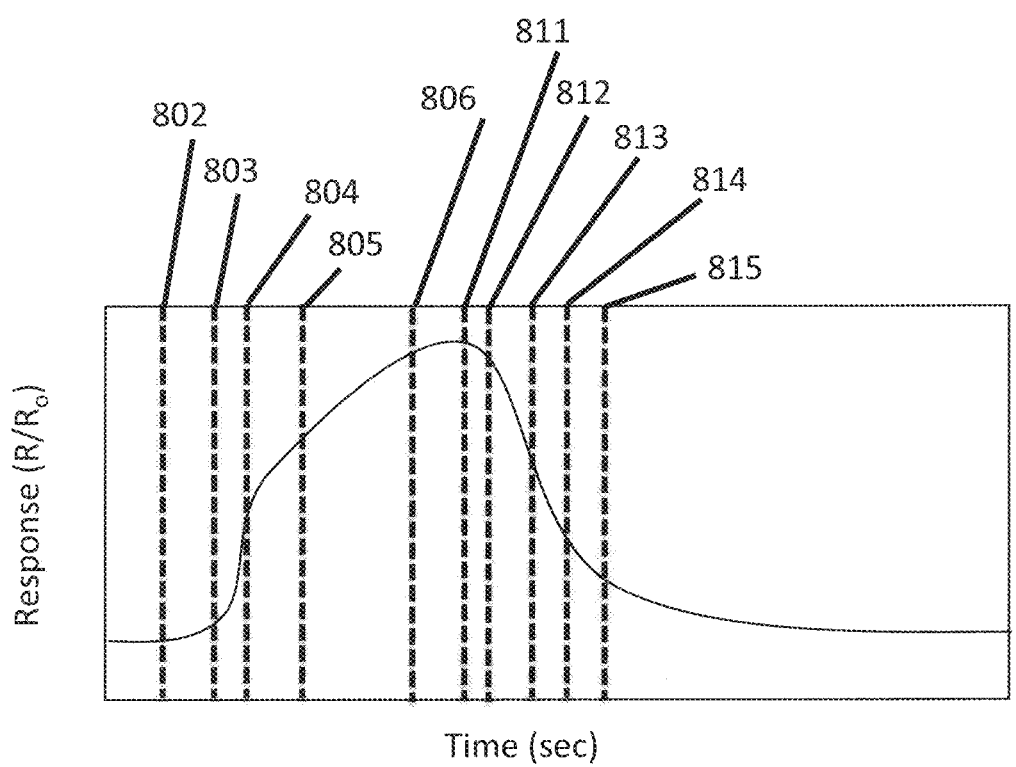

FIG. 8A-FIG. 8C. FIG. 8A and FIG. 8B illustrate concentration profile curves representing the concentration distribution of a gas analyte between a gas source and a sensor derivatized with an exemplary biomolecular diffusion matrix, during gas exposure and diffusion of gas analytes to the sensor (FIG. 8A) and after stopping gas exposure and during diffusion of gas analytes from the sensor (FIG. 8B). FIG. 8C shows the corresponding gas sensor response profile and the position in time corresponding to each concentration profile curve. In FIG. 8A and FIG. 8B, for ease of viewing, biomolecular diffusion matrix is represented with shaded rectangles, and the gas analyte is represented as horizontal arrows. Concentration (arb.) (y-axis) refers to concentration represented as arbitrary units. Distances from gas source (x-axis) are in arbitrary units.

FIG. 8A is a one-dimensional concentration profile simulation 801 for gas analyte 106, at different times during gas exposure and diffusion of gas analytes to the sensor. Concentrations are expressed as the log concentration of the gas analyte in arbitrary units (arb.) (y-axis) as a function of the distance from gas source in arbitrary units (x-axis). In FIG. 8A, each concentration profile curve (802, 803, 804, 805, 806) represents the concentration of the gas analyte at positions between the gas source and sensor 101B at a specific time during gas sample exposure when gas analyte molecules are diffusing through diffusion matrix 104B and becoming adsorbed to the surface of gas sensor 101B. An exemplary, sample exposure duration may be 30 sec, and the concentration profile curves 802-806 may represent gas concentration profiles determined at, for example, 1 sec, 5 sec, 10 sec, 15 sec, and 30 sec, respectively, following initiation of gas sample exposure. Gas analyte concentration at the sensor surface increases with increasing time of gas exposure, e.g., curve 806 representing the longest time after initiation of gas sample exposure. The simulation is primarily based on Fick's diffusion law, treating the biomolecular diffusion matrix with a diffusion coefficient distinct from the region between the outermost surface of biomolecular diffusion matrix 104B on sensor 101B and the gas analyte source (at position 0 on the x-axis). The simulation takes into account diffusion parameters and the adsorption and desorption rates of the gas analyte on the surface of the sensor.

FIG. 8B shows a one-dimensional concentration profile simulation 810 for gas analyte 106, at specific times after exposure to the gas sample is stopped, expressed as the log concentration of the gas analyte in arbitrary units (arb.) (y-axis) as a function of the distance from gas source (x-axis). In this period, the carrier gas flowing over sensor 101B does not contain gas analyte. As such, some gas analytes desorb from the surface of gas sensor 101B and diffuse away, with carrier gas, from the sensor through diffusion matrix 104B. The concentration profile curves (811, 812, 813, 814, 815) represent gas concentrations at progressively longer times, at positions between the gas source and the outermost surface of biomolecular diffusion matrix 104B, after gas analyte exposure is stopped. Gas concentration at sensor 101B is highest at the shortest time point after gas exposure has stopped, represented by curve 811, and is lowest at the longest time point after gas exposure has stopped, represented by curve 815.

FIG. 8C shows the corresponding gas sensor response profile and the position in time corresponding to each concentration profile curve 802, 803, 804, 805, 806, 811, 812, 813, 814, and 815 shown in FIGS. 8A and 8B. The intersection of a concentration profile curve with the gas sensor response profile curve correlates the amount of gas adsorbed on sensor 101B with the sensor response at that time, during diffusion of gas analyte to the sensor (FIG. 8A, 802-806) and during diffusion of gas analyte away from the sensor (FIG. 8B, 811-815). Sensor response is greatest at the time interval between 806 and 811 when the concentration of gas analyte at the sensor surface is near saturation (i.e., the maximum number of sensor surface sites are occupied by gas analyte 106.

Figure 9:
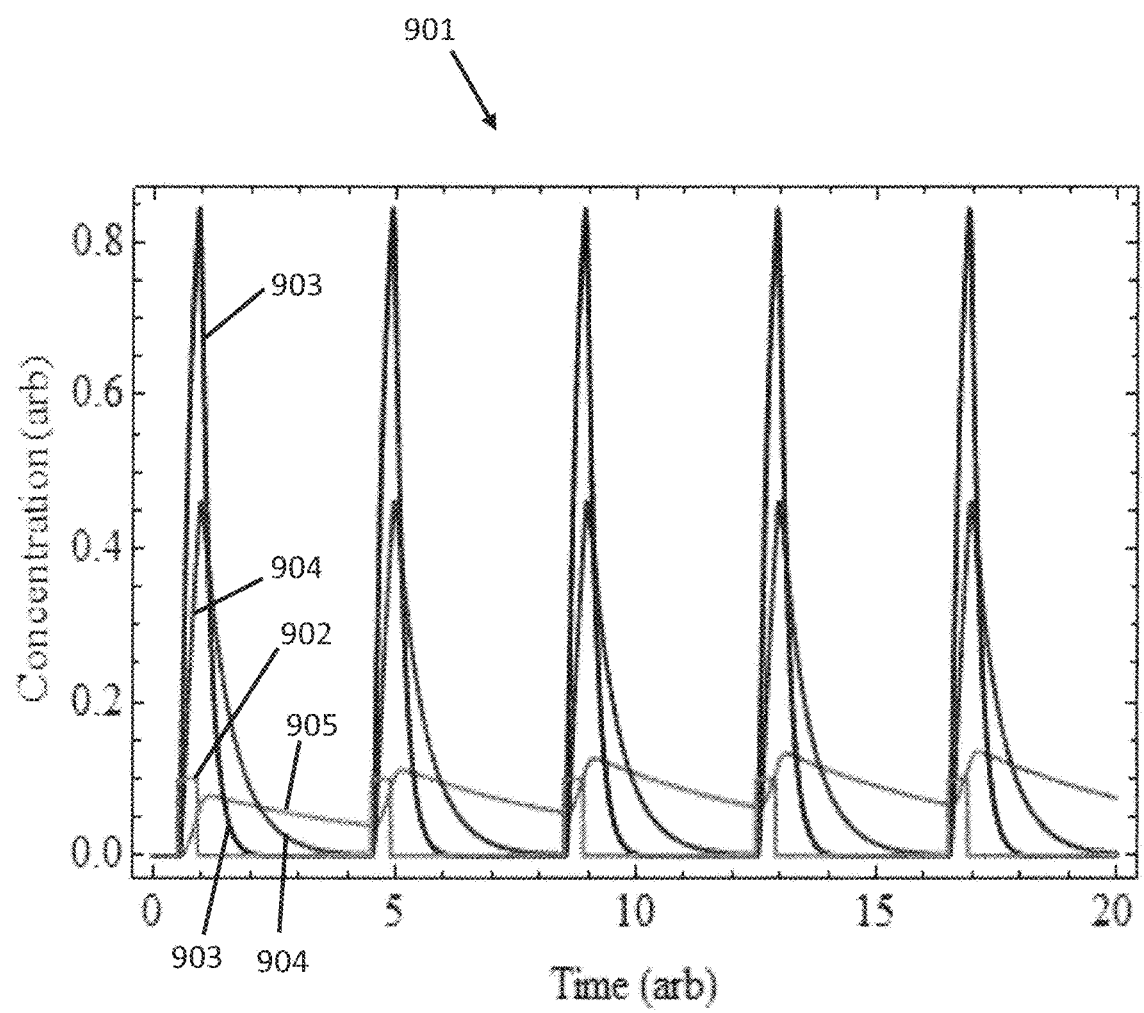
FIG. 9. shows a one-dimensional simulation of sensor-adsorbed concentration of a single gas analyte species with gas sensors having different exemplary biomolecular diffusion matrices, after a square pulse injection of a gas sample. Concentration (arb.) refers to concentration represented as arbitrary units. Time (x-axis) is in arbitrary units.

FIG. 9. shows a one-dimensional simulation of sensor-adsorbed concentration of a single gas analyte species with gas sensors having different exemplary biomolecular diffusion matrices, after a square pulse injection of a gas sample. Concentration (arb.) refers to concentration represented as arbitrary units. Time (x-axis) is in arbitrary units. FIG. 9 depicts the effect of different diffusion matrices on the concentration profile of a monotonic gas analyte adsorbed on the surface of a gas sensor. Simulated gas sensor concentration profiles 901 show gas concentration generated for five replicate exposures (square pulse) 902 of the same gas analyte. The simulations include concentration profiles representing three different biomolecular diffusion matrices that result in gas analyte diffusion coefficients of 200 cm$^2$/s 903; 20 cm$^2$/s 904; and 2 cm$^2$/s 905. Differences in the time for the gas analyte concentration at the sensor to increase and reach a maximum, in the peak magnitude of gas analyte concentration at the sensor surface, and in the time required for the gas analyte concentration at the sensor to fall after termination of gas sample exposure are observed for the different biomolecular diffusion matrices. For sensor concentration profiles determined when the gas analyte diffusion coefficient is relatively larger (e.g., 903) the change in the gas analyte concentration at the sensor is marked by a rapid rise, followed by a rapid decrease of gas analyte concentration at the sensor after stopping gas exposure. In contrast, a sensor having a biomolecular diffusion matrix that results in a relatively smaller gas analyte diffusion coefficient, displays a concentration profile as depicted by 905 with relatively slower increases in the gas analyte concentration at the sensor followed by a corollary slower return back to the pre-exposure concentration prior to gas exposure. Profiles 903 and 904 are labeled at two locations on each curve.

Figure 10A:
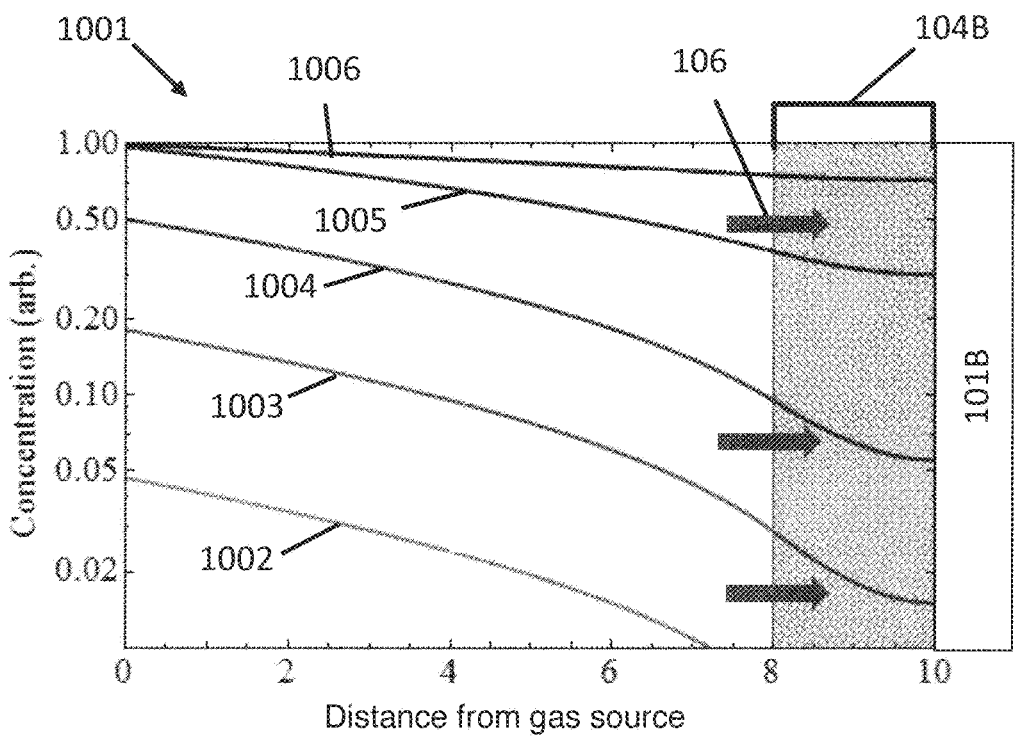
FIG. 10A-FIG. 10D.
Figure 10B:
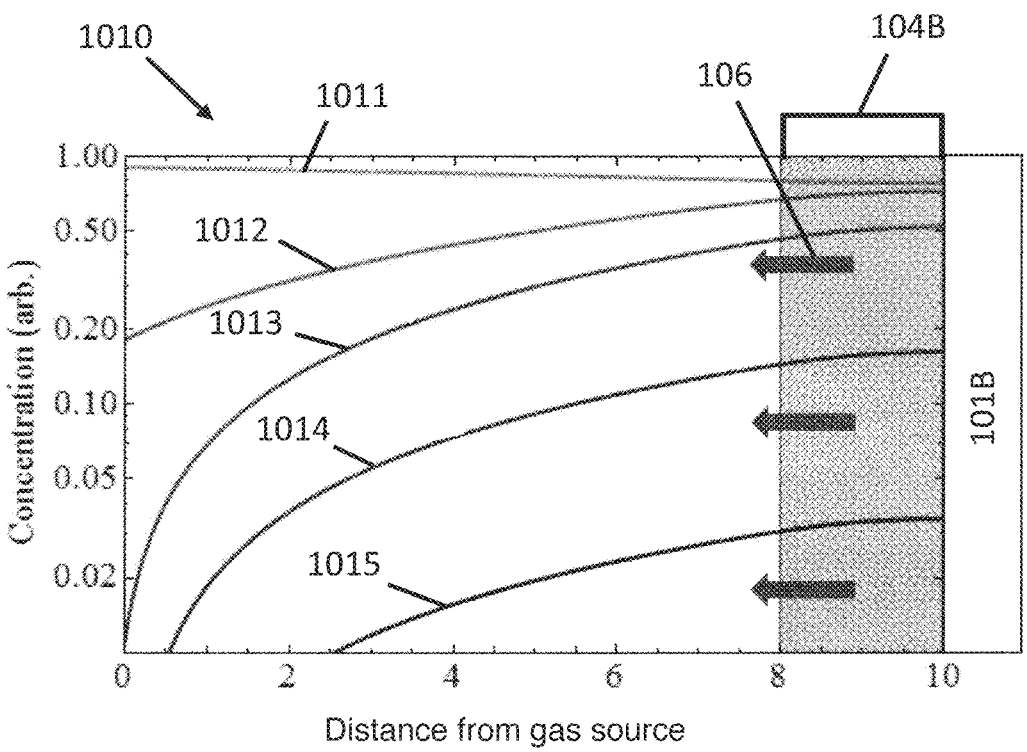
Figure 10C:
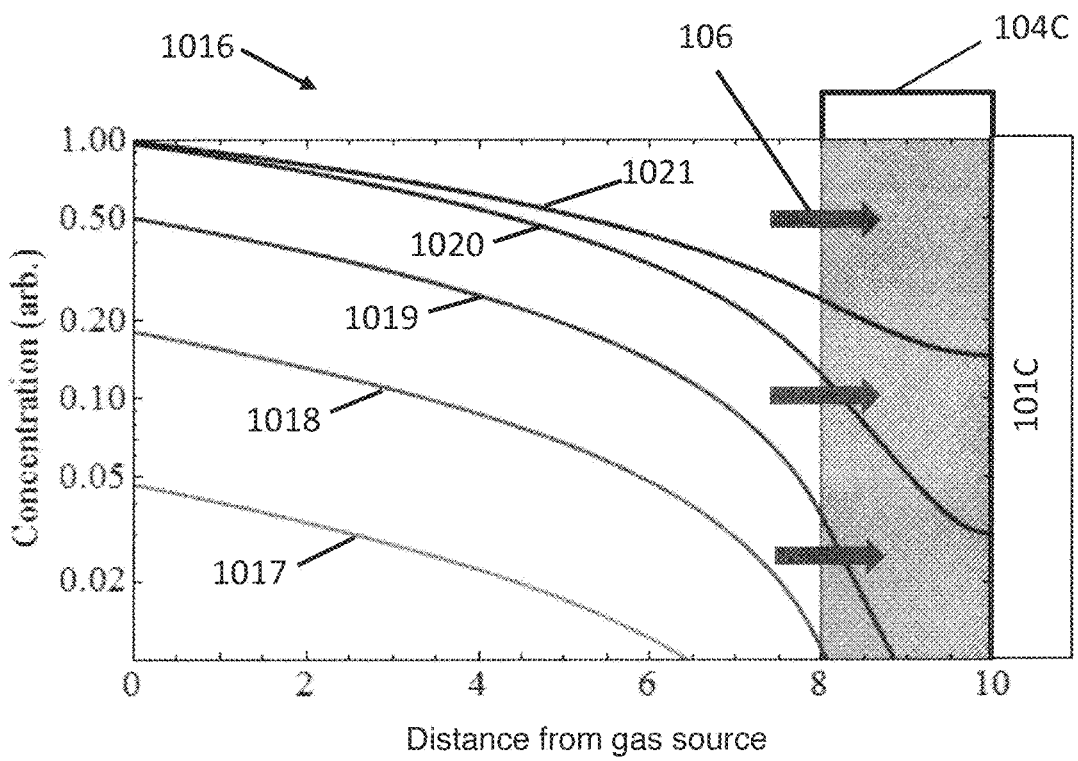
Figure 10D:
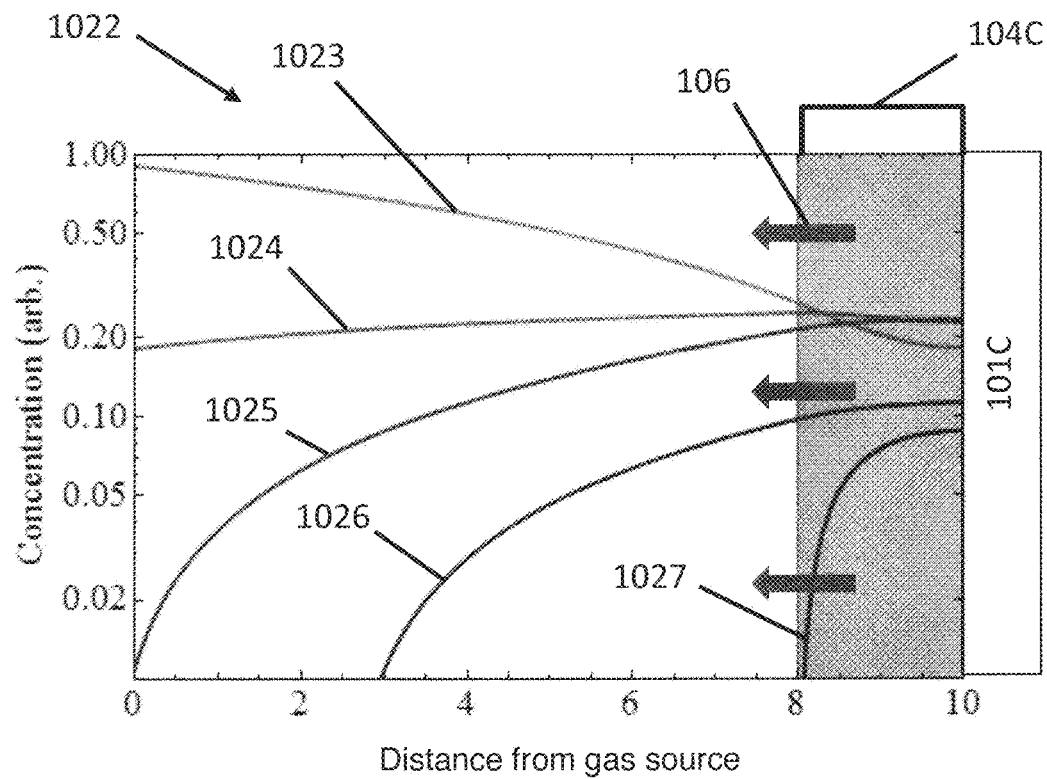

FIG. 10A-FIG. 10D. FIG. 10A and FIG. 10B illustrate concentration profile curve simulations representing the concentration distribution of a gas analyte between a gas source and a sensor derivatized with one type of exemplary biomolecular diffusion matrix. FIG. 10A shows concentration profile curves during gas exposure and diffusion of gas analytes to the sensor. FIG. 10B shows concentration profiles curves after stopping gas exposure and during diffusion of gas analytes from the sensor. FIG. 10C and FIG. 10D illustrate concentration profile curves representing the concentration distribution of the same gas analyte between a gas source and a sensor derivatized with a different type of exemplary biomolecular diffusion matrix. FIG. 10C shows concentration profile curves during gas exposure and diffusion of gas analytes to the sensor, and FIG. 10D shows concentration profiles curves after stopping gas exposure and during diffusion of gas analytes from the sensor. For ease of viewing, the biomolecular diffusion matrices are shown as shaded rectangles and the gas analyte is represented as horizontal arrows. Concentration (arb.) refers to concentration represented as arbitrary units. Distances from gas source (x-axis) are in arbitrary units.

The simulations illustrate that different types of diffusion matrices present on a gas sensor affect the diffusion of a gas analyte to and from the sensor, thereby affecting the gas sensor response profile. FIG. 10A shows concentration profile simulation 1001 during gas exposure and during diffusion of gas analyte 106 through biomolecular diffusion matrix 104B to sensor 101B. Concentration profile curves 1002, 1003, 1004, 1005, and 1006 represent gas concentration profiles determined at, for example, 1 sec, 5 sec, 10 sec, 15 sec, and 30 sec, respectively, after initiating gas exposure. FIG. 10B shows the concentration profile simulation 1010 after stopping gas exposure and during diffusion of gas analyte 106 away from sensor 101B and through biomolecular diffusion matrix 104B. Concentration profile curves 1011, 1012, 1013, 1014, and 1015 represent gas concentration profiles determined at, for example, 1 sec, 5 sec, 10 sec, 15 sec, and 30 sec, respectively, after stopping gas exposure.

FIG. 10C and FIG. 10D illustrate concentration profile simulations 1016 and 1022 for sensor 101C having a different biomolecular diffusion matrix 104C. Here, biomolecular diffusion matrix 104C has a different diffusion coefficient than biomolecular diffusion matrix 104B of FIG. 10A and FIG. 10B. FIG. 10C shows concentration profile simulation 1016 during gas exposure and during diffusion of gas analyte 106 through biomolecular diffusion matrix 104C to sensor 101C. Concentration profile curves 1017, 1018, 1019, 1020, and 1021 represent gas concentration profiles determined at, for example, 1 sec, 5 sec, 10 sec, 15 sec, and 30 sec, respectively, after initiating gas exposure. FIG. 10D illustrates the concentration profile simulation 1022 after stopping gas exposure and during diffusion of gas analyte 106 away from sensor 101C and through biomolecular diffusion matrix 104C. Concentration profile curves 1023, 1024, 1025, 1026, and 1027 represent gas concentration profiles determined at, for example, 1 sec, 5 sec, 10 sec, 15 sec, and 30 sec, respectively, after stopping gas exposure.

Figure 11:
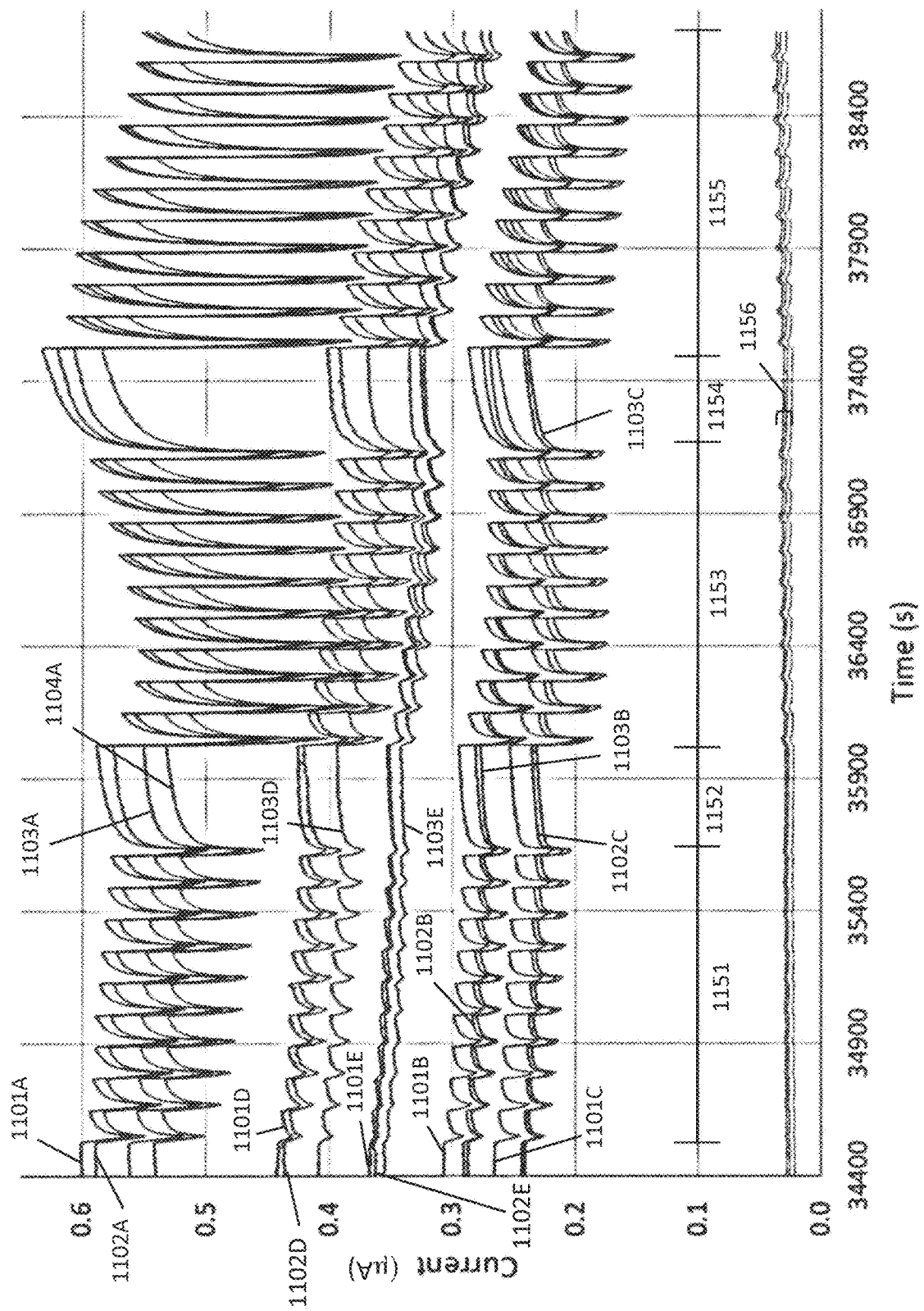
FIG. 11 shows gas sensor response profiles determined for exposure of gas sensors to the gas analyte N-methyl-2-pyrrolidone, at three different gas concentrations. The sensors were linker-derivatized or derivatized with one of four different biomolecular diffusion matrices covalently coupled to their surfaces. Raw current (µA) was measured for determining individual sensor responses, and data were plotted as a function of time (seconds). Time on the x-axis represents the total elapsed time during the recording of all sensor responses.

FIG. 11 shows gas sensor response profiles determined for exposure of gas sensors to the gas analyte N-methyl-2-pyrrolidone, at three different relative gas concentrations. The sensors were linker-derivatized or derivatized with one of four different biomolecular diffusion matrices covalently coupled to their surfaces. Raw current (μA) was measured for determining individual sensor responses, and data were plotted as a function of time (seconds). Time on the x-axis represents the total elapsed time during the recording of all sensor responses.

In this example, sensors were derivatized with linker structures or one of two different proteins or two different oligopeptides. Proteins and oligopeptides were spotted over selected regions that included multiple sensors on an array of semiconducting tin oxide nanotrace sensors. In this example, all sensors 101 were present on the same monolithic array 102. For derivatizing sensors, spotting was carried out by first silanizing the entire sensor array using dimethylepoxyoctylsilane (Gelest Inc.; Morrisville, Pa., USA). The silane couples to free —OH groups on the surface of the tin oxide. After ~1 min of exposure to silane, oligopeptide and protein molecules were spotted on the sensor array surface and left on the sensor surface for ~1 hr, after which excess fluid was rinsed from the surface. Each oligopeptide or protein spot covered between 7 and 10 sensors. Linker-derivatized nanotraces were modified only with silane were present between regions of the sensor array that comprised sensors having a biomolecular diffusion matrix. In addition, one row of sensors having no tin oxide was used as a control or open circuit sensor in which no current passes during determination of a response.

As described for some embodiments of testing regimen 501, ten consecutive gas sensor response profiles to the same gas species sample 509 were determined, and ten sensor response profiles were determined for the same gas species at different concentrations 510. Response profiles 1101A, 1102A, 1103A, and 1104A were determined using four different sensors 101A derivatized by linker silane treatment 103; sensor response profiles 1101B, 1102B, and 1103B were determined using three different sensors derivatized with a biomolecular diffusion matrix comprising a 7-mer peptide sequence, Fmoc-DLESFLD (MW~946 Da); sensor response profiles 1101C, 1102C, and 1103C were determined using three different sensors derivatized with a biomolecular diffusion matrix comprising an 8-mer peptide, Fmoc-RVNEWVID (MW~1,156 Da); sensor response profiles 1101D, 1102D, and 1103D were determined using three different sensors derivatized with a biomolecular diffusion matrix comprising BSA (MW~66,500 Da); and sensor response profiles 1101E, 1102E, and 1103E were determined using three different sensors derivatized with a biomolecular diffusion matrix comprising an anti-biotin antibody (MW~160,000 Da). For each set of sensor types, response profiles were determined using three different relative concentrations of N-methyl-2-pyrrolidone that were diluted from concentrations of 2%, 5%, and 7% of saturated vapor.

In this example, the sensor raw current (μA) was measured for determining individual sensor responses, and data were plotted as a function of time (seconds). Sensor responses were recorded throughout the entire time during the multiple exposures at the three different gas analyte concentrations 510 using testing regimen 501. Ten replicate gas exposures of the same gas 509 at the same concentration for all sensors and all derivatizations were performed using testing regimen 501. After gas exposure initiation 505, gas exposure lasted 30 sec and was followed by a gas exposure stop 506. The final (tenth) exposure of the same gas 509 was delayed for a longer period of time before data determination of the next set of ten replicate exposures 509 at the higher gas concentration 510 using testing regimen 501. The first ten gas exposures, at the lowest relative concentration, are represented by the ten sensor response profiles in regions 1151 followed by a delay period 1152 indicated on the horizontal line above the x-axis. The second ten gas exposures, at the middle relative concentration, are represented by the ten sensor response profiles in regions 1153 followed by delay period 1154, which preceded the third set of ten gas exposures, at the highest relative concentration, which is represented by the ten sensor response profiles in region 1155. The response profile 1156 for nanotraces without semiconducting metal oxide between electrodes shows a minimal response with much lower current magnitude at the same bias voltage relative to sensors with metal oxide semiconductor.

As was observed in other experimental examples, the data shown in FIG. 11 demonstrate that replicate sensors that are derivatized with the same type of diffusion matrix had similar response profile features in response to the same gas analyte, including sensor response rise time, peak magnitude of sensor response, and sensor response fall time. This was observed for all replicate gas exposures to sensors with the same type of biomolecular diffusion matrix, regardless of the gas analyte concentration. In FIG. 11, the five different types of sensors (four derivatized with different biomolecular diffusion matrices and one underivatized) each had different initial current values, which was a result of a change in the current carrying capacity of the nanotrace sensor in response to the different amount of diffusion matrix biomolecules being present on the sensor surface relative to the underivatized sensors and other factors such as the physical dimensions and intrinsic conductivity of the metal oxide sensing material.

Molecular diffusion matrix properties, e.g., molecular weight, chemical composition, and thickness, influence the rate of diffusion of a gas analyte to the sensor. Consequently, sensor response profiles for a given gas analyte are different depending on the type of diffusion matrix present on the sensor. The data for these different sensor response profiles, determined with one or more control and test gas samples are used with analysis algorithms 513 to enable the identification and quantification of each gas analyte in a test sample. Qualitative and quantitative differences between control and test sample gases can be determined by using ROIC 512 and data analysis algorithms 513 and comparing data recorded for control sample 502 sensor response profiles and test sample 514 sensor response profiles. Numerous computational algorithms are available in the art that are useful for identifying differences in datasets. By way of example, the replicate control gas sensor profiles and the associated data sets shown in FIG. 11, determined for the control gas N-methyl-2-pyrrolidone at different concentrations and with sensors having different types of biomolecular diffusion matrices, may be compared with sensor response profiles similarly determined for a test gas sample as part of an analysis to identify and quantify gas analytes in a test gas sample.

FIG. 12A-FIG. 12E show five series of gas sensor response profiles in response to the gas analyte acetone, each series determined with a gas sensor derivatized with a different type of diffusion matrix. All y-axes represent normalized response ($R/R_0$), and all x-axes represent time (seconds). The sensor response profiles were determined using four different concentrations of saturated acetone vapor pressure (0.07%, 1201; 0.05%, 1202; 0.02%, 1203; and 0.01%, 1204) with five different types of gas sensors. The concentration of acetone was controlled by the ratiometric mixing of a clean, dry air stream with a fraction of a stream that is redirected through an impinger vessel containing liquid acetone. The vapor that is carried from this stream is mixed with the clean, dry air using a mass flow controller to yield the desired concentration ratios. The concentrations were approximately a percentage of acetone-saturated vapor pressure at the temperature and pressure of the measurement system. For this experiment, sensor current was converted to resistance, which is calculated from Ohm's law (V=IR) where the applied bias voltage V is divided by the raw sample current $I_s$ for each point ($R=V/I_s$). After calculating the sample resistance, the normalized resistance ratio $R/R_0$ was determined by dividing each resistance value by the average of the first few resistance measurements ($R_0$) just prior to gas exposure.

Sensor response profiles plotted in each of FIG. 12A-FIG. 12E represent the averaged, normalized response profile of multiple sensors having the same type of derivatization, to each concentration of gas analyte. FIG. 12A shows the averaged, normalized sensor responses, for four gas concentrations (1201A, 1202A, 1203A, 1204A), for all sensors derivatized with silane treatment. FIG. 12B shows the averaged, normalized sensor responses for four gas concentrations (1201B, 1202B, 1203B, 1204B), for all sensors derivatized with the 7-mer peptide, Fmoc-DLESFLD (MW~946 Da). FIG. 12C shows the averaged, normalized sensor response for four gas concentrations (1201C, 1202C, 1203C, 1204C), for all sensors derivatized with the 8-mer peptide, Fmoc-RVNEWVID (MW~1,156 Da). FIG. 12D shows the averaged, normalized sensor responses for four gas concentrations (1201D, 1202D, 1203D, 1204D), for all sensors derivatized with BSA (MW~66,500 Da). FIG. 12E shows the averaged, normalized sensor responses for four gas concentrations (1201E, 1202E, 1203E, 1204E), for all sensors derivatized with anti-biotin antibody (MW~160,000 Da).

Like the raw current determinations illustrated in FIG. 11 for the gas analyte N-methyl-2-pyrrolidone, differences in the sensor response profile features were observed among the sensors with different types of derivatization (FIG. 12A-FIG. 12E) shown here for the gas analyte acetone. Differences were observed in the sensor response rise time, the peak magnitude of the sensor response, and the sensor response fall time. The differences in the response profiles are attributed to differences in the diffusion rate for acetone gas through the different types of diffusion matrices. The peak magnitude of the response is influenced by the molecular weight of the diffusion matrix molecules, and hence the thickness and density of the diffusion layer. For example, the high molecular weight anti-biotin antibody (FIG. 12E) shows the lowest peak magnitude of sensor response among the different biomolecular diffusion matrices examined. In the normalized, averaged response profiles of FIG. 12, the pressure required for check valve opening, caused a delay in the sensor response, which became more pronounced for lower gas analyte concentrations. In other invention embodiments, removing the requirement for pressure thresholds in the measurement system eliminated the pressure dependence of the diffusion rate from the gas source to the gas sensor.

FIG. 13A-FIG. 13E show five series of gas sensor response profiles in response to the gas analyte xylene, each series determined with a gas sensor derivatized with a different type of diffusion matrix. All y-axes represent normalized response ($R/R_0$), and all x-axes represent time (seconds).

The sensor response profiles were determined using four different dilution percentages of a vessel containing saturated xylene vapor (0.07%, 1301A, 1301B, 1301C, 1301D, 1301E; 0.05%, 1302A, 1302B, 1302C, 1302D, 1302E; 0.02%, 1303A, 1303B, 1303C, 1303D, 1303E; and 0.01%, 1304A, 1304B, 1304C, 1304D, 1304E) with gas sensors derivatized with five different types of diffusion matrices. The sensor derivatizations for the series in FIG. 13A-FIG. 13E were the same as those described for FIG. 12A-FIG. 12E. Experimental methods and data analyses were the same as described for FIG. 12. Sensor response profiles plotted in each of FIG. 13A-FIG. 13E represent the averaged, normalized response profile, to each concentration of gas analyte, for multiple sensors derivatized with the same type of diffusion matrix. As was observed for acetone in FIG. 12, differences among the gas sensor response profiles to xylene were also observed. The differences in the response profile for gas analyte acetone (FIG. 12A-FIG. 12E) and chemically-distinct gas analyte xylene (FIG. 13A-FIG. 13E) provide exemplary data that can be used with deconvolution algorithms 513 to numerically separate the sensor response of one gas species analyte from a different gas species analyte, resulting in a gas analyte signature for identifying and quantifying one or more gas analyte in a test sample.

FIG. 14A-FIG. 14F show six series of gas sensor response profiles, determined using silane-derivatized sensors in response to six different gas analytes, each analyte at three different concentrations of saturated gas vapor pressure (0.07%, 0.05%, and 0.02%). FIG. 14A, acetone; FIG. 14B, ammonia; FIG. 14C, dimethylacetophenone; FIG. 14D, N-methyl-2-pyrrolidone; FIG. 14E, toluene; FIG. 14F, xylene. Sensor response profiles plotted in each of FIG. 14A-FIG. 14F represent the average of multiple sensor response profiles for sensors with the same derivatization, and were determined for each gas concentration. All y-axes represent normalized response ($R/R_0$), and all x-axes represent time (seconds).

The sensor response profiles for 0.07%, 0.05%, and 0.02% concentrations of saturated gas vapor pressure are respectively; acetone—1401, 1402, 1403; ammonia—1404, 1405, 1406; dimethylacetophenone—1407, 1408, 1409; N-methyl-2-pyrrolidone—1410, 1411, 1412; toluene—1413, 1414, 1415; xylene—1416, 1417, 1418). Here, differences among response profiles of silane-derivatized sensors to six different gas analytes were observed.

FIG. 15A-FIG. 15F show six series of gas sensor response profiles, determined using sensors derivatized with the 8-mer peptide RVNEWVID as a diffusion matrix, in response to six different gas analytes, each analyte at three different concentrations of saturated gas vapor pressure (0.07%, 0.05%, and 0.02%). FIG. 15A, acetone; FIG. 15B, ammonia; FIG. 15C, dimethylacetophenone; FIG. 15D, N-methyl-2-pyrrolidone; FIG. 15E, toluene; FIG. 15F, xylene. Sensor response profiles plotted in each of FIG. 15A-FIG. 15F represent the average of multiple sensor response profiles determined for each gas concentration. All y-axes represent normalized response ($R/R_0$), and all x-axes represent time (seconds).

The sensor response profiles for 0.07%, 0.05%, and 0.02% concentrations of saturated gas vapor pressure are respectively; acetone—1501, 1502, 1503; ammonia—1504, 1505, 1506; dimethylacetophenone—1507, 1508, 1509; N-methyl-2-pyrrolidone —1510, 1511, 1512; toluene—1513, 1514, 1515; xylene—1516, 1517, 1518. In this example, sensor response profiles determined with this diffusion matrix were found to be different depending on the gas analyte being detected.

FIG. 16A-FIG. 16F show six series of gas sensor response profiles, determined using sensors derivatized with the relatively large protein anti-biotin antibody as a diffusion matrix, in response to six different gas analytes, each analyte at three different concentrations of saturated gas vapor pressure (0.07%, 0.05%, and 0.02%). FIG. 16A, acetone; FIG. 16B, ammonia; FIG. 16C, dimethylacetophenone; FIG. 16D, N-methyl-2-pyrrolidone; FIG. 16E, toluene; FIG. 16F, xylene. Sensor response profiles plotted in each of FIG. 16A-FIG. 16F represent the average of multiple sensor response profiles determined for each gas concentration. All y-axes represent normalized response ($R/R_0$), and all x-axes represent time (seconds).

The sensor response profiles for 0.07%, 0.05%, and 0.02% concentrations of saturated gas vapor pressure are respectively; acetone—1601, 1602, 1603; ammonia—1604, 1605, 1606; dimethylacetophenone—1607, 1608, 1609; N-methyl-2-pyrrolidone—1610, 1611, 1612; toluene—1613, 1614, 1615; xylene—1616, 1617, 1618). As observed in the experiment described in FIG. 15, for all sensors derivatized here with the biomolecular diffusion matrix, anti-biotin, gas sensor response profiles differed depending on the gas analyte being detected.

For the sensor response profiles shown in FIGS. 14-16, the y-axes for corresponding plots with the same gas (e.g., ammonia in FIG. 14B, FIG. 15B, and FIG. 16B) have the same scale, so as to effectively demonstrate the differences in sensor response profiles determined with the same gas but with different sensor derivatization (FIG. 14, silane-derivatized; FIG. 15, 8-mer peptide; FIG. 16, anti-biotin antibody). The sensor response profiles for the six gas analytes shown in (FIG. 14-FIG. 16) and the differences among them provide exemplary data that can be used to identify and quantify one or more gas analyte after implementing data analysis deconvolution algorithms 513 that can numerically separate the sensor response of one gas analyte from another.

In some embodiments of the invention, a ratiometric comparison of gas sensor response profiles (FIG. 17-FIG. 20) is another exemplary means for determining and illustrating differences among gas sensor response profiles and for identifying and quantifying different gas analytes in a gas mixture. A ratiometric comparison plot represents the ratio of a sensor response profile determined with a sensor derivatized with one type of diffusion matrix to a sensor response profile determined with a sensor derivatized with a different type of diffusion matrix. In some embodiments of the invention in which multiple sensors are used, the averaged, normalized sensor response profiles are used for ratiometric comparisons. Gas sensor response profile data obtained using various, selected control gas species, various gas concentrations, and various diffusion matrices on sensors provide data for deconvolution algorithms 513 that are used to identify and quantify gas analytes in a test gas sample. In some aspects of the invention, higher numbers of sensor response profiles with different types of diffusion matrices may be used to increase the accuracy of identifying and quantifying gas analytes in a test gas sample.

FIG. 17A-FIG. 17J show ten ratiometric comparison plots of sensor response profiles determined after exposure of sensors to the gas analyte xylene. Sensor response profile ratios include FIG. 17A, linker-derivatized sensor to sensor derivatized with peptide DLESFLD (1701); FIG. 17B, linker-derivatized sensor to sensor derivatized with peptide RVNEWVID (1702); FIG. 17C, linker-derivatized sensor to sensor derivatized with BSA (1703); FIG. 17D, linker-derivatized sensor to sensor derivatized with anti-biotin (1704); FIG. 17E, sensor derivatized with peptide DLESFLD to sensor derivatized with peptide RVNEWVID (1705); FIG. 17F, sensor derivatized with peptide DLESFLD to sensor derivatized with BSA (1706); FIG. 17G, sensor derivatized with peptide DLESFLD to sensor derivatized with anti-biotin (1707); FIG. 17H, sensor derivatized with peptide RVNEWVID to sensor derivatized with BSA (1708); FIG. 17I, sensor derivatized with peptide RVNEWVID to sensor derivatized with anti-biotin (1709); FIG. 17J, sensor derivatized with BSA to sensor derivatized with anti-biotin (1710). All y-axes represent normalized response ($R/R_0$), and all x-axes represent time (seconds).

The ratiometric comparison plots shown in FIG. 17A-FIG. 17J were used for comparing sensor response profiles determined with the gas analyte xylene, at 0.07% of saturated vapor near standard temperature and pressure, each response profile determined with a linker-derivatized sensor or with a sensor having a different biomolecular diffusion matrix. Ratiometric comparison illustrated that differences were present between all sensor response profiles compared (FIG. 17 A-FIG. 17J).

FIG. 18A-FIG. 18J show ten ratiometric comparison plots of sensor response profiles determined after exposure of sensors to the gas analyte xylene. All sensors used in these examples were underivatized bare sensors (i.e., no silane linker treatment). The same sensors as were described in the description for FIG. 17A-FIG. 17J were exposed to xylene, but here, gas exposure to the underivatized bare sensors occurred prior to the coupling of the biomolecular diffusion matrices to the sensors or prior to any silane treatment of sensors. All y-axes represent normalized response (R/R$_0$), and all x-axes represent time (seconds).

Sensor response profiles for the underivatized bare sensors were determined with the gas analyte xylene, at 0.07% of saturated vapor. Ratiometric comparison plots of these profiles are shown in FIG. 18A-FIG. 18J. The plots in FIG. 18 (1801, 1802, 1803, 1804, 1805, 1806, 1807, 1808, 1809, 1810) represent comparisons of sensor profiles determined with the exact same sensors described in the corresponding plots for FIG. 17A-FIG. 17J, but using response profiles determined before any derivatization or silane treatment of sensors. As expected, the ratiometric comparisons indicated extremely small differences among response profiles of underivatized/untreated sensors.

FIG. 19A-FIG. 19J show ten ratiometric comparison plots of sensor response profiles determined after exposure of sensors to the gas analyte toluene. Sensor response profile ratios include FIG. 19A, linker-derivatized sensor to sensor derivatized with peptide DLESFLD (1901); FIG. 19B, linker-derivatized sensor to sensor derivatized with peptide RVNEWVID (1902); FIG. 19C, linker-derivatized sensor to sensor derivatized with BSA (1903); FIG. 19D, linker-derivatized sensor to sensor derivatized with anti-biotin (1904); FIG. 19E, sensor derivatized with peptide DLESFLD to sensor derivatized with peptide RVNEWVID (1905); FIG. 19F, sensor derivatized with peptide DLESFLD to sensor derivatized with BSA (1906); FIG. 19G, sensor derivatized with peptide DLESFLD to sensor derivatized with anti-biotin (1907); FIG. 19H, sensor derivatized with peptide RVNEWVID to sensor derivatized with BSA (1908); FIG. 19I, sensor derivatized with peptide RVNEWVID to sensor derivatized with anti-biotin (1909); FIG. 19J, sensor derivatized with BSA to sensor derivatized with anti-biotin (1910). All y-axes represent normalized response (R/R$_0$), and all x-axes represent time (seconds).

The ratiometric comparison plots shown in FIG. 19A-FIG. 19J were used for comparing sensor response profiles determined with the gas analyte toluene, at 0.07% of saturated vapor near standard temperature and pressure, each response profile determined with a linker-derivatized sensor or with a sensor having a different biomolecular diffusion matrix. Ratiometric comparison illustrated that differences were present between all sensor response profiles compared (FIG. 19A-FIG. 19J).

FIG. 20A-FIG. 20J show ten ratiometric comparison plots of sensor response profiles determined after exposure of sensors to the gas analyte toluene. All sensors used in these examples were underivatized bare sensors (i.e., no silane linker treatment). The same sensors as were described in the description for FIG. 19A-FIG. 19J were exposed to toluene, but here, gas exposure to the underivatized bare sensors occurred prior to the coupling of the biomolecular diffusion matrices to the sensors or prior to any silane treatment of sensors. All y-axes represent normalized response (R/R$_0$), and all x-axes represent time (seconds).

Sensor response profiles for the underivatized and untreated bare sensors were determined with the same gas analyte toluene, at 0.07% of saturated vapor. Ratiometric comparison plots of these profiles are shown in FIG. 20A-FIG. 20J. The plots in FIG. 20 (2001, 2002, 2003, 2004, 2005, 2006, 2007, 2008, 2009, 2010) represent comparisons of sensor profiles determined with the exact same sensors described in the corresponding plots for FIG. 19A-FIG. 19J, but using profiles determined before any derivatization or silane treatment of sensors. As expected, the ratiometric comparisons indicated small differences among response profiles of underivatized/untreated sensors.

The corresponding ratiometric comparison plots in FIG. 17 and FIG. 19 (e.g., 1701 vs. 1901, 1702 vs. 1902, 1703 vs. 1903, 1704 vs. 1904, 1705 vs. 1905, 1706 vs. 1906, 1707 vs. 1907, 1708 vs. 1908, 1709 vs. 1909, 1710 vs. 1910) show differences that are attributable to the differential interaction of the two different gases with the specific type of diffusion matrix present on a sensor. These differences represent exemplary data that enable identification and quantification of gas analytes in test samples.

Figure 21:
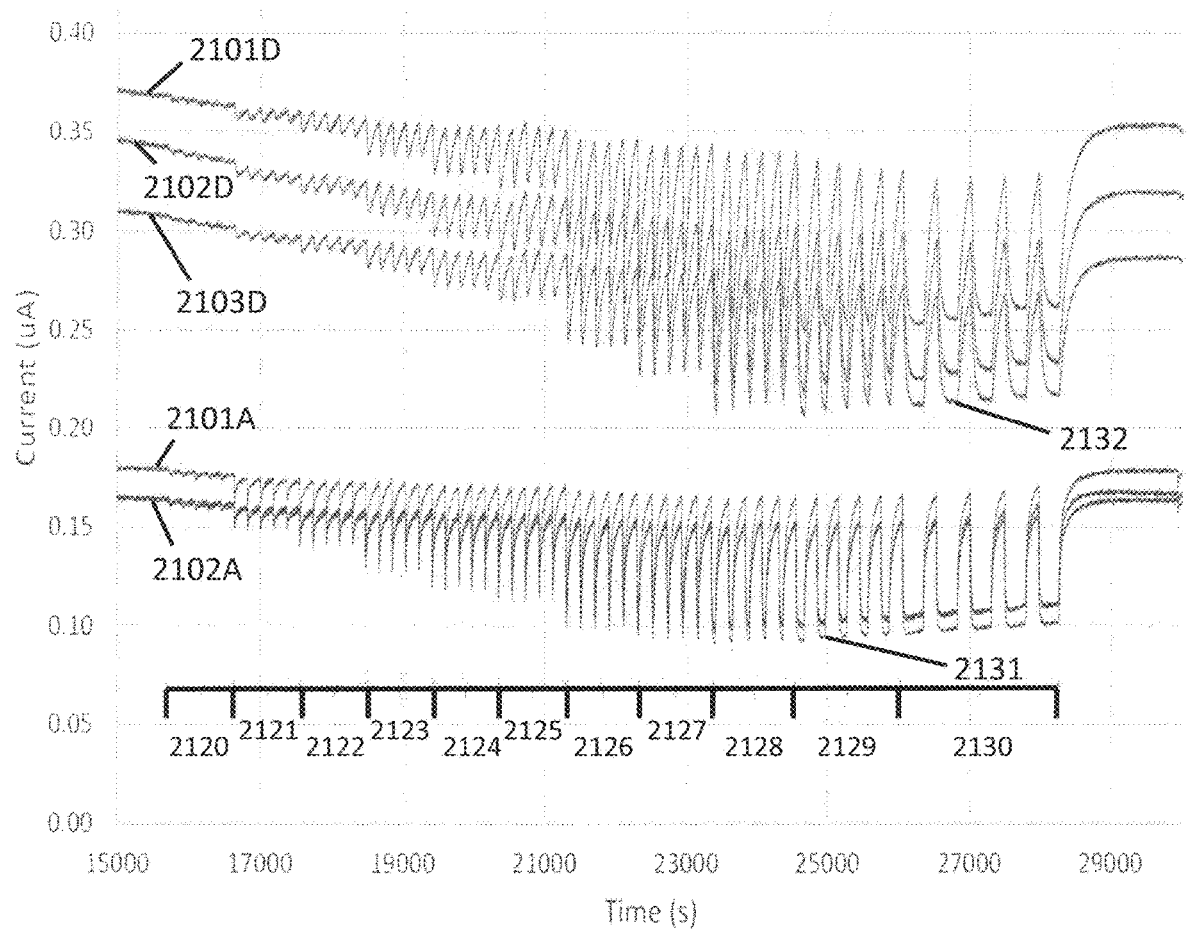
FIG. 21 shows five series of gas sensor response profiles determined with the gas analyte N-methyl-2-pyrrolidone using two different sensors derivatized with linkers 2101A, 2102A and three different sensors derivatized with an anti-biotin biomolecular diffusion matrix 2101D, 2102D, 2103D. Sensor response was plotted as raw current vs. time. Time on the x-axis represents the total elapsed time during the recording of all sensor responses using testing regimen 501.

FIG. 21 shows five series of gas sensor response profiles determined with the gas analyte N-methyl-2-pyrrolidone using two different sensors derivatized with linkers 2101A, 2102A and three different sensors derivatized with an anti-biotin biomolecular diffusion matrix 2101D, 2102D, 2103D. Sensor response was plotted as raw current vs. time. Time on the x-axis represents the total elapsed time during the recording of all sensor responses using testing regimen 501.

Each series of sensor response profiles includes six replicate response profiles 509 recorded for each of eleven different gas exposure time defined as the time interval between initiating gas sensor exposure 505 to stopping gas sensor exposure 506. Sensor responses were recorded throughout the entire time during the multiple gas exposures. Regions of the graph with different gas exposure times are indicated on the horizontal line above the x-axis and included 2 sec 2120, 3 sec 2121, 4 sec 2122, 5 sec 2123, 8 sec 2124, 10 sec 2125, 20 sec 2126, 30 sec 2127, 60 sec 2128, 120 sec 2129, and 300 sec 2130 exposure times. The data show that response profiles determined with multiple sensors having the same diffusion matrix are very similar and are highly reproducible. Additionally, sensor response data demonstrated that the gas exposure time required to reach sensor saturation was affected by the presence of the diffusion matrix. Sensor saturation occurs when all available reactive sites on the sensor surface are occupied and the rates of adsorption and desorption have reached equilibrium. The amplitude of the response displacement stops increasing or decreasing and levels off even though gas exposure continues, (i.e., after initiating gas exposure 505, but before stopping gas exposure 506). Linker-derivatized sensors 2101A, 2102A saturate between 60 sec and 120 sec (2131). In contrast, sensors derivatized with anti-biotin saturated between 120 sec and 300 sec as illustrated by the replicate responses 2132. The time required to reach saturation can be defined as an exemplary representation of the response profile data and may be used for identifying a specific gas analyte in a test sample using data analysis algorithms 513.

Figure 22:
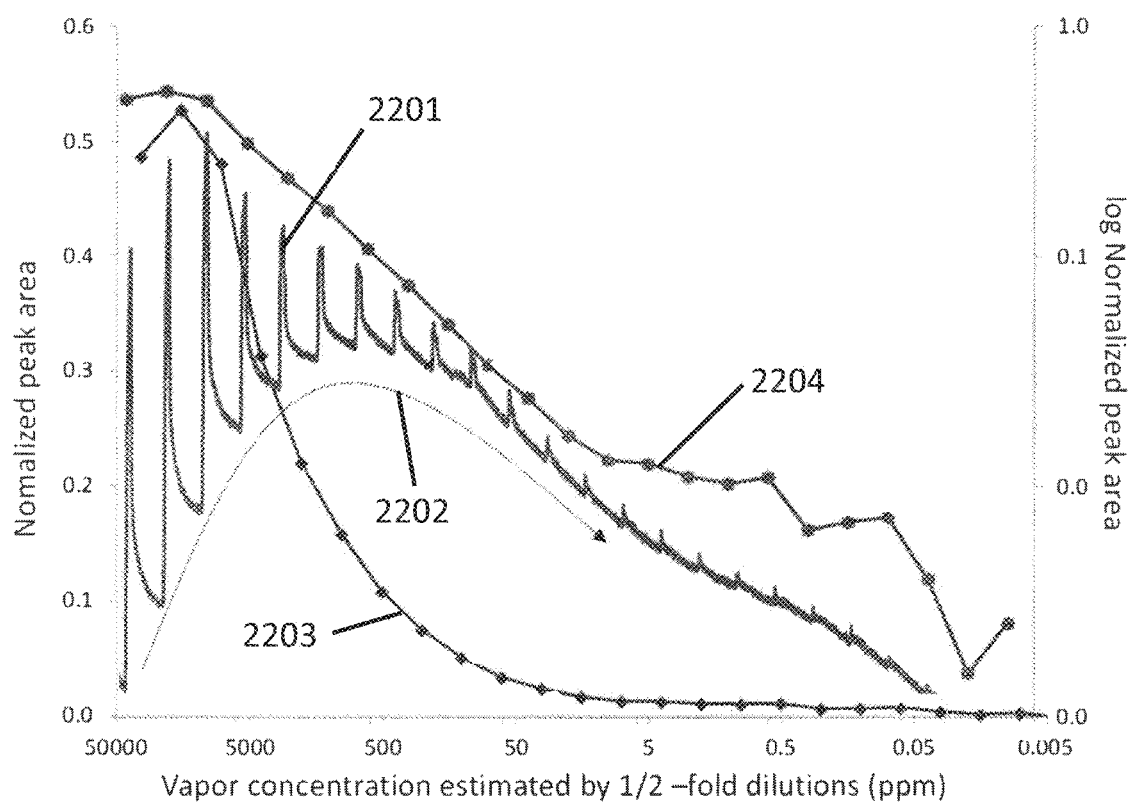
FIG. 22 shows a concentration dilution series of sensor response profiles determined for exposure of linker-derivatized sensors to methanol. The plot illustrates quantitative dependence of sensor response profiles on gas analyte concentration. The left side y-axis is normalized peak area, the right-side y-axis is log-normalized peak area, and x-axis is vapor concentration estimated by ½-fold dilutions (ppm).

FIG. 22 shows a concentration dilution series of sensor response profiles determined for exposure of linker-derivatized sensors to methanol. The plot illustrates quantitative dependence of sensor response profiles on gas analyte concentration. The left side y-axis is normalized peak area, the right side y-axis is log normalized peak area, and x-axis is vapor concentration estimated by ½-fold dilutions (ppm).

In embodiments of the invention, the sensitivity and detection limit of the gas nanosensor is dependent on the differences in the diffusion rate of the control gas species and the diffusion rate of the test sample gas analyte for a given diffusion matrix. FIG. 22 illustrates a concentration profile trend for one sensor 2201 in which profiles were determined for multiple exposures of methanol at different saturated vapor pressures of methanol (in parts per million, ppm). In this experiment the first concentration profile was determined using a low flow rate carrier gas stream at 50 sccm through an impinger that was initially filled with 100% saturated vapor of methanol ~167,000 ppm at standard temperature and pressure. The flow rate of 50 sccm and vessel volume of 60 ml were chosen such that the concentration of methanol gas would be diluted approximately in half during each gas exposure interval. Subsequent concentration profiles were also determined after a dilution of the gas concentration.

For sensor responses determined with high concentrations of gas, the length of the time interval between initiating gas exposure 505 and stopping gas exposure 506 was insufficient to reach sensor saturation with adsorbed gas analyte molecules. The increase in magnitude of the response in subsequent exposures illustrates that saturation was not been reached at the highest gas concentrations examined. Furthermore, the length of time between subsequent exposures was insufficient to permit gas molecules to diffuse from the sensor back through the diffusion matrix and back into the clean, dry air gas stream after stopping gas exposure 506. This is manifested as an increase in residual peak area value 2202 during consecutive gas exposures, when sensors are exposed to high concentrations of gas. This phenomenon was observed at concentrations above ~1,000 ppm (the maximum on curve 2202). At gas concentrations less than ~1,000 ppm, the time between exposures was sufficient for gas analytes to desorb from the sensor prior to the next gas exposure. However, the ultimate sensitivity in this exemplary data is obscured by the residual adsorbed gas during exposure of subsequent lower concentrations of gas. For all gas concentrations, the peak resistance value of the gas response profile decreased steadily as the gas analyte concentration was diluted to the lowest concentration recorded, ~0.05 ppm gas. Curve 2203 shows the normalized peak area (left vertical axis) for each consecutive concentration profile vs. gas analyte concentration, and the log of the normalized peak area 2204 (right vertical axis) is also plotted vs. gas analyte concentration. Exposure of sensors to high gas concentrations obscured the sensor baseline response. In some embodiments of the invention, sensors may be protected from high gas concentrations, for example by rapidly expelling adsorbed gas analyte through heating, chemical or optical desorption methods.

Figure 23A:
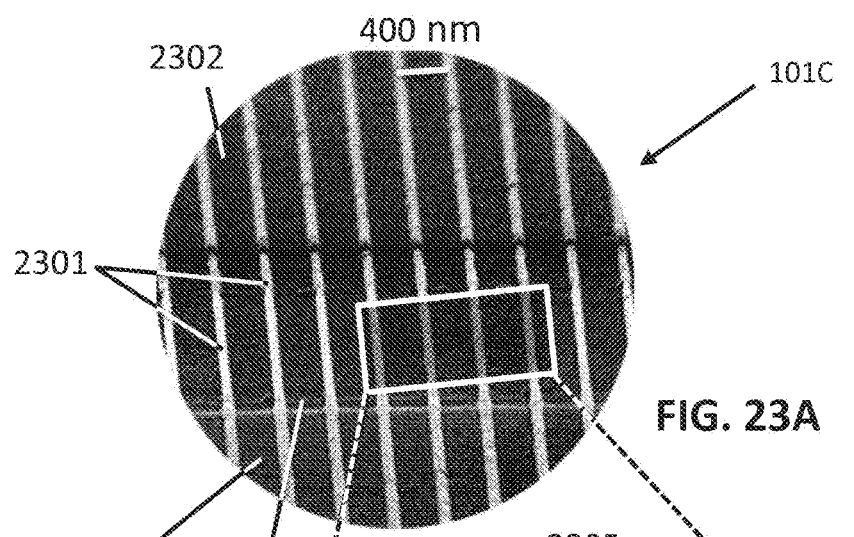
FIG. 23A-FIG. 23B.
Figure 23B:
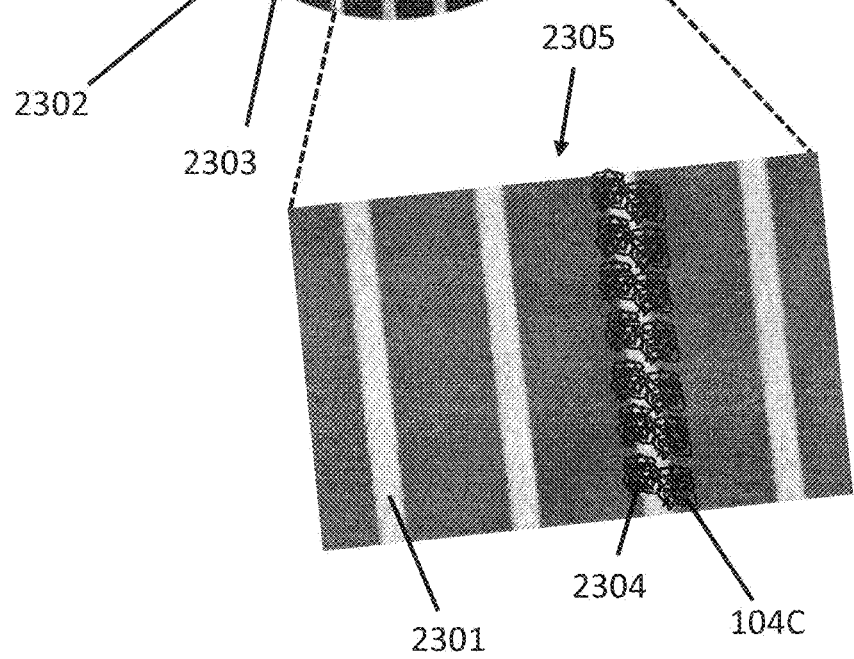

FIG. 23A-FIG. 23B. FIG. 23A shows an exemplary embodiment of a region of a gas analyte nanosensor fabricated using the method of nanoimprint lithography. FIG. 23B shows an enlargement of a section of the nanosensor having semiconducting metal oxide nanotraces with a schematic illustration of a diffusion matrix on one nanotrace of the sensor. Scale bar in FIG. 23A=400 nm.

FIG. 23A is a scanning electron microscope image of a region an exemplary nanosensor gas detector useful in embodiments of the invention. In this example, nanoimprint lithography followed by nanoimprint lift-off was employed to produce individual tin oxide nanotraces 2301 that make up the nanosensor. Here nanotraces have a width of 80 nm and were separated by a pitch of 400 nm (shown as the white bar connecting the centers of two nanotraces near the top of FIG. 23A). These dimensions were defined by the nanoimprint template that was produced by electron beam lithography according to methods known in the art. Each nanotrace has a high surface area to volume ratio for the span between consecutive electrodes 2302. In some embodiments of the invention, electrodes 2302 may be protected from the environment using masking layer 2303 which extends beyond the edges of electrodes 2302, while still allowing for contact of gas analytes with gas sensor nanotraces 2301.

Because all nanotraces 2301 are connected to the same electrode 2302, they respond in parallel when exposed to gas analytes. As such, each sensor 101C represented schematically in FIG. 1, may comprise 1, 2, 5, 10, 20, 50, 100, 250, 500, 1,000, 5,000, 50,000, 1,000,000 or any number therebetween of parallel nanotraces, inclusive of the smaller and larger numbers listed, responding in parallel and enabling the determination of gas sensor response profiles. In some embodiments of the invention, illustrated in the enlarged section 2305 of nanosensor 101C shown in FIG. 23B, a biomolecular diffusion matrix 104C is formed by anchoring biomolecules 2304 to individual nanotraces 2301 that collectively impact the overall sensor response profile. In FIG. 23B, for ease of viewing, biomolecular diffusion matrix 104C is illustrated only on one nanotrace present in the sensor 101C but could be present on any number of nanotraces in the sensor.

Figure 24:
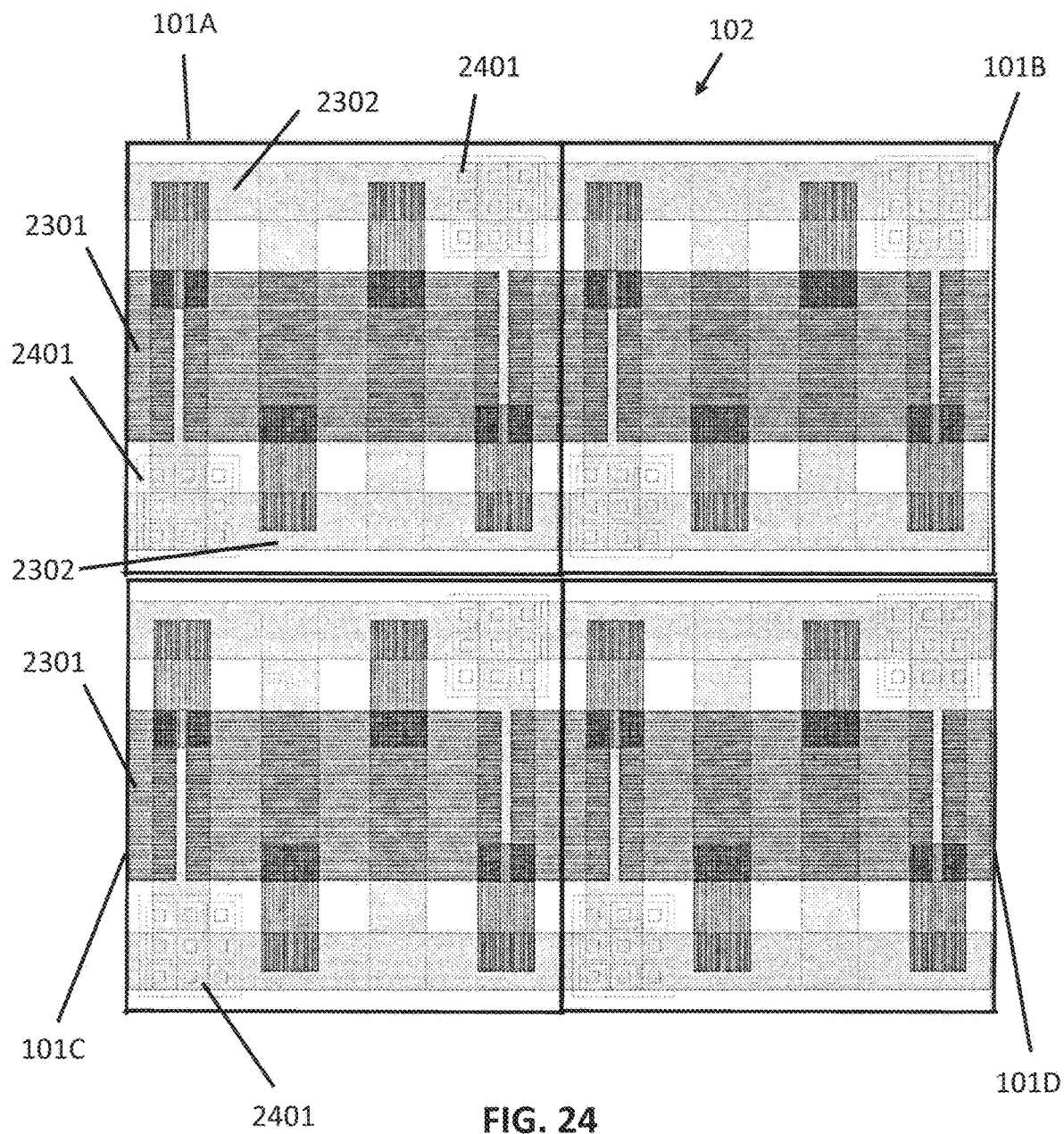
FIG. 24 shows an exemplary embodiment of a 2×2 array of nanosensors, each sensor comprising semiconductor metal oxide gas detection material fabricated on CMOS read-out integrated circuits.

FIG. 24 shows an exemplary embodiment of a 2×2 array of nanosensors, each sensor comprising semiconductor metal oxide gas detection material fabricated on CMOS read-out integrated circuits. Sensor array 102 comprises sensors 101A, 101B, 101C, 101D, each sensor comprising exemplary multiple conductometric nanotraces 2301 fabricated directly on a silicon CMOS read-out integrated circuit array. Each sensor 101 connects to individual circuits in the ROIC through electrode pads 2401 present in opposite corners of an independently electrically-addressable sensor 101. ROIC electrode pads 2401 are in contact with electrode 2302, which is connected to multiple conductometric semiconductor tin oxide nanotraces 2301. The number of sensors in array 102 can range from 1 to millions, with individual sensors having dimensions that range from about 100 nm to hundreds of microns. Numerous CMOS ROIC devices are described in the art. In some embodiments of the invention, the number of nanotraces and electrode interconnectivity with sensor array 102 can be coupled to include additional nanotraces with a larger sensor footprint and more current carrying capacity, which may improve sensitivity and detection limits.

In addition to sensors having nanotraces that are 80 nm in width and set on a 400 nm pitch, as illustrated in FIG. 23A, some sensors used in experimental examples had thin films or nanotraces with larger or smaller widths and were set on different pitches. The total surface area of gas sensor transducer material 2301 present on a given sensor 101 may affect the gas sensor response profile.

Figure 25:
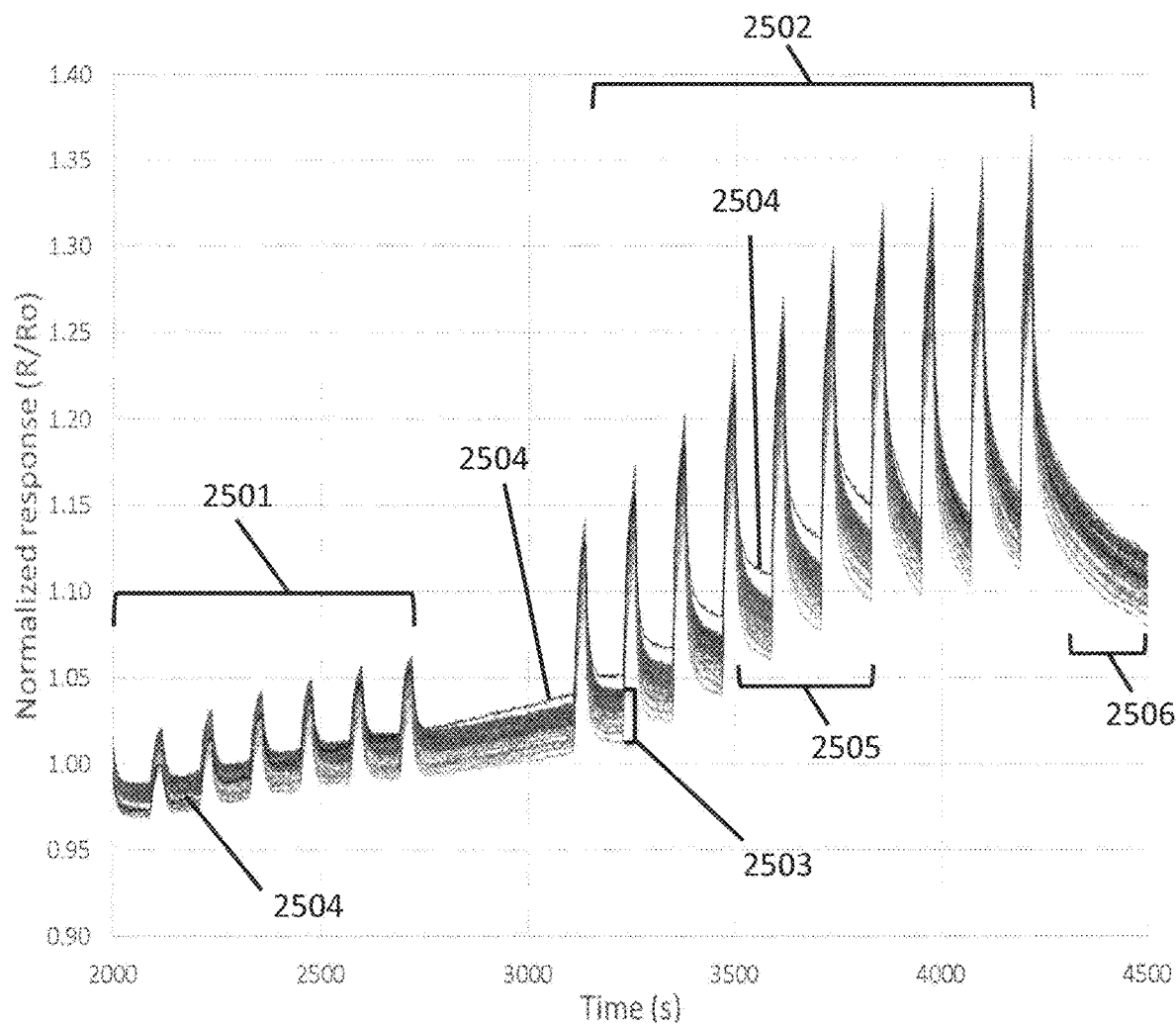
FIG. 25 shows a series of gas sensor response profiles determined using linker-derivatized semiconducting nanotrace sensors having a width of 80 nm and spacing of 400 nm for two different concentrations of N-methyl-2-pyrrolidone, and a sensor response profile for one sensor having a nanotrace width of 400 nm and spacing of 800 nm.

FIG. 25 shows a series of gas sensor response profiles determined using linker-derivatized semiconducting nanotrace sensors having a width of 80 nm and spacing of 400 nm for two different concentrations of N-methyl-2-pyrrolidone, and a sensor response profile for one sensor having a nanotrace width of 400 nm and spacing of 800 nm. The series of 55 replicate gas sensor response profiles includes response profiles that were determined with a lower concentration 2501 and a higher concentration 2502 of gas analyte N-methyl-2-pyrrolidone. Sensor response profiles 2503 for each of 55 gas sensors having a nanotrace width of 80 nm on a 400 nm pitch were similar for lower and higher concentrations of gas. The plotted sensor response profile 2504 for a single sensor, having a nanotrace width of 400 nm on an 800 nm pitch showed response profile characteristics different from those observed for the set of 55 gas sensor response profiles 2503. (In FIG. 25, sensor response profile 2504 is represented with a darker line than the 55 response profiles 2503 and is labeled at multiple locations.) Sensor response profile 2504 exhibited characteristics different from those of response profiles 2503 at lower gas analyte concentration 2501, at higher gas analyte concentration 2502, after the gas analyte saturated the sensor 2505 (post saturation), and after a replicate sensor saturation period 2506. These data indicate that the dimensions and pitch of sensor nanotraces can be selected and adjusted, just as the diffusion matrix and other experimental parameters can be varied, to enhance identification and quantification of individual gas species in a gas sample. Varying the size and pitch of nanotraces used in combination with different diffusion matrices can improve the detection and identification of gas analytes in a test sample.

What is claimed is:

1. A method of determining the presence of a selected gas species analyte in a test gas sample, the method comprising:
   exposing a plurality of gas sensors to the test gas sample wherein the plurality of gas sensors are the same type of gas sensor and comprise either (1) a sensor derivatized with a first type of diffusion matrix and a sensor derivatized with a second type of diffusion matrix or (2) a sensor derivatized with the first type of diffusion matrix and a sensor lacking a diffusion matrix, wherein the first type of diffusion matrix and the second type of diffusion matrix each comprise one or more than one of molecules, molecular compounds, and ionic compounds, selected to interact non- specifically with the selected gas species analyte during diffusion of the selected gas species analyte through the diffusion matrix and to and from the plurality of gas sensors;
   stopping exposure of the plurality of gas sensors to the test gas sample;
   determining a test sample sensor response profile of each of the plurality of gas sensors during diffusion of gas species in the test gas sample to and from each sensor, from a selected time prior to initiating sensor exposure to the test gas sample to a selected time after stopping sensor exposure to the test gas sample;
   comparing the determined test sample sensor response profiles;
   comparing each determined test sample sensor response profile with a corresponding control sample sensor response profile, each of the corresponding control sample sensor response profiles being determined with a control gas sample comprising the selected gas species analyte and with the same sensor or with a sensor of the same type and having the same derivatization state as the determined test sample sensor response profile with which it is compared; and,
   determining the presence of the selected gas species analyte in the test gas sample based on at least one of differences and similarities observed between one or more than one of (i) the compared test sample sensor response profiles and (ii) the compared each test sample sensor response profile and corresponding control sample sensor response profile.

2. The method of claim 1 wherein each of the corresponding control sample sensor response profiles were determined with a control gas sample comprising a plurality of selected different gas species analytes.

3. The method of claim 1 wherein the corresponding control sample sensor response profiles are stored in a database.

4. The method of claim 3 wherein comparing the determined test sample sensor response profiles and comparing each determined test sample sensor response profile with the corresponding control sample sensor response profile comprise using one or more than one of read-out integrated circuits and data analysis deconvolution algorithms.

5. The method of claim 4 further comprising determining a concentration of the selected gas species analyte in the test gas sample.

6. The method of claim 1 wherein comparing the determined test sample sensor response profiles and comparing each determined test sample sensor response profile with the corresponding control sample sensor response profile comprise performing a ratiometric comparison.

7. The method of claim 1 further comprising quantifying the selected gas species analyte.

8. The method of claim 1 wherein the corresponding control sample sensor response profiles are determined before the test sample sensor response profiles.

9. The method of claim 1 wherein one or both of the first type of diffusion matrix and the second type of diffusion matrix comprise biomolecules selected to interact non-specifically with the selected gas species analyte during diffusion of the selected gas species analyte through the one or both of the first type of diffusion matrix and the second type of diffusion matrix and to and from the plurality of gas sensors.

10. The method of claim 9 wherein the biomolecules are coupled to a porous support matrix.

11. The method of claim 9 wherein the biomolecules comprise one or more than one of a nucleic acid, a protein, and a peptide.

12. The method of claim 1 wherein the test gas sample further comprises a liquid.

13. The method of claim 1 wherein the test gas sample comprises a biological sample.

14. The method of claim 13 wherein the biological sample is from an organism.

15. The method of claim 1 wherein the test gas sample is an environmental sample.

16. The method of claim 1 wherein the plurality of gas sensors are in a sensor array.

17. The method of claim 1 wherein the plurality of gas sensors are conductometric semiconducting metal oxide sensors.

18. The method of claim 17 wherein the plurality of gas sensors are nanotraces made by nanoimprint lithography.

19. The method of claim 1 wherein the one or more than one of molecules, molecular compounds, and ionic compounds selected to interact non-specifically with the selected gas species analyte are selected to interact by one or both of chemical interaction and electrostatic interaction.

20. A method of determining the presence of a plurality of selected different gas species analytes in a test gas sample, the method comprising:
   exposing a plurality of gas sensors to a test gas sample wherein the plurality of gas sensors are the same type of gas sensor and comprise either (1) a sensor derivatized with a first type of diffusion matrix and a sensor derivatized with a second type of diffusion matrix or (2)

a sensor derivatized with the first type of diffusion matrix and a sensor lacking a diffusion matrix, wherein the first type of diffusion matrix and the second type of diffusion matrix each comprise one or more than one of molecules, molecular compounds, and ionic compounds, selected to interact non-specifically with the plurality of selected different gas species analytes during diffusion of the plurality of selected different gas species analytes through the diffusion matrix and to and from the plurality of gas sensors;

stopping exposure of the plurality of gas sensors to the test gas sample;

determining a test sample sensor response profile of each of the plurality of gas sensors during diffusion of gas species in the test gas sample to and from each sensor, from a selected time prior to initiating sensor exposure to the test gas sample to a selected time after stopping sensor exposure to the test gas sample;

comparing the determined test sample sensor response profiles;

comparing each determined test sample sensor response profile with a corresponding control sample sensor response profile, each of the corresponding control sample sensor response profiles being determined with a control gas sample comprising the plurality of selected different gas species analytes and with the same sensor or with a sensor of the same type and having the same derivatization state as the determined test sample sensor response profile with which it is compared; and, determining the presence of the plurality of selected different gas species analytes in the test gas sample based on at least one of differences and similarities observed between one more than one of (i) the compared test sample sensor response profiles and (ii) the compared each test sample sensor response profile and corresponding control sample sensor response profile.

21. The method of claim 20 wherein the corresponding control sample sensor response profiles are stored in a database and wherein comparing the determined test sample sensor response profiles and comparing each determined test sample sensor response profile with the corresponding control sample sensor response profile comprise using one or more than one of read-out integrated circuits and data analysis deconvolution algorithms.

* * * * *